(12) United States Patent
Kolling et al.

(10) Patent No.: US 11,746,361 B2
(45) Date of Patent: Sep. 5, 2023

(54) METABOLIC ENGINEERING FOR SIMULTANEOUS CONSUMPTION OF XYLOSE AND GLUCOSE FOR PRODUCTION OF CHEMICALS FROM SECOND GENERATION SUGARS

(71) Applicant: Braskem S.A., Camacari (BR)

(72) Inventors: Veronica Maria Rodege Gogola Kolling, Camacari (BR); Ane Fernanda Beraldi Zeidler, Camacari (BR); Lucas Pedersen Parizzi, Camacari (BR)

(73) Assignee: BRASKEM S.A., Camaçari (BR)

( * ) Notice: Subject to any disclaimer, the term of this patent is extended or adjusted under 35 U.S.C. 154(b) by 0 days.

(21) Appl. No.: 16/841,312

(22) Filed: Apr. 6, 2020

(65) Prior Publication Data

US 2020/0318146 A1 Oct. 8, 2020

Related U.S. Application Data

(60) Provisional application No. 62/829,398, filed on Apr. 4, 2019.

(51) Int. Cl.
| | | |
|---|---|---|
| *C12P 7/18* | (2006.01) | |
| *C12N 1/20* | (2006.01) | |
| *C12P 7/42* | (2006.01) | |
| *C12N 9/88* | (2006.01) | |
| *C12N 9/10* | (2006.01) | |
| *C12N 9/12* | (2006.01) | |
| *C12N 9/04* | (2006.01) | |
| *C12N 9/90* | (2006.01) | |
| *C12P 7/28* | (2006.01) | |
| *C12N 9/92* | (2006.01) | |
| *C12P 7/04* | (2006.01) | |
| *C12N 1/21* | (2006.01) | |

(52) U.S. Cl.
CPC .......... *C12P 7/18* (2013.01); *C12N 1/20* (2013.01); *C12N 9/0006* (2013.01); *C12N 9/1029* (2013.01); *C12N 9/1205* (2013.01); *C12N 9/13* (2013.01); *C12N 9/88* (2013.01); *C12N 9/90* (2013.01); *C12N 9/92* (2013.01); *C12P 7/04* (2013.01); *C12P 7/28* (2013.01); *C12P 7/42* (2013.01); *C12P 2203/00* (2013.01); *C12Y 503/01005* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 9,284,582 | B2 | 3/2016 | Lee et al. |
| 2005/0214913 | A1 | 9/2005 | Marchenko et al. |
| 2015/0050691 | A1* | 2/2015 | Lee ............... C12N 1/22 435/106 |
| 2015/0225745 | A1* | 8/2015 | Vroom ............. C12P 7/04 435/128 |
| 2017/0260551 | A1* | 9/2017 | Koch ............. C12N 9/13 |
| 2019/0010523 | A1* | 1/2019 | Walther ............. C12P 7/18 |

FOREIGN PATENT DOCUMENTS

| | | |
|---|---|---|
| WO | WO-2014025747 A1 | 2/2014 |
| WO | WO-2016162712 A1 | 10/2016 |
| WO | WO-2017156166 A1 | 9/2017 |

OTHER PUBLICATIONS

Alkim et al., Optimization of ethylene glycol production from (D) xylose via a synthetic pathway implemented in *Escherichia coli*, Microb. Cell. Fact. 14, 2015, 127. (Year: 2015).*

Zhu et al., The CRISPR/Cas9-facilitated multiplex pathway optimization (CFPO) technique and its application to improve the *Escherichia coli* xylose utilization pathway, Metabolic Eng. 43, 2017, 37-45. (Year: 2017).*

Desai et al., Regulation of arabinose and xylose metabolism in *Escherichia coli*, Appl. Environ. Microbiol. 76, 2010, 1534-32 (Year: 2010).*

Genbank, Accession No. LN832404.1, 2015, www.ncbi.nlm.gov. (Year: 2015).*

Alkim, C. et al., "Optimization of ethylene glycol production from (d)-xylose via a synthetic pathway implemented in *Escherichia coli*", Microbial Cell Factories, vol. 158, No. 1, Dec. 1, 2015 (Dec. 1, 2015), p. 9, XP055329509, DOI: 10.1186/s12934-015-0312-7, See Table 1; Fig. 1; p. 5.

Bai, W. et al., "Engineering nonphosphorylative metabolism to synthesize mesaconate from lignocellulosic sugars in *Escherichia coli*", Metabolic Engineering, vol. 38, Sep. 30, 2016 (Sep. 30, 2016), pp. 285-292, XP029805004, ISSN: 1096-7176, DOI: 10.1016/J.YMBEN.2016.09.007, Whole doc., in particular section 3.2.

International Search Report and Written Opinion for Application No. PCT/BR2020/050115, dated Aug. 17, 2020, 18 pages.

Kim, S.M., et al., "Simultaneous utilization of glucose and xylose via novel mechanisms in engineered *Escherichia coli*", Metabolic Engineering, 30, (2015), pp. 141-148.

Salusjärvi, L. et al., "Biotechnological production of glycolic acid and ethylene glycol: current state and perspectives", Applied Microbiology and Biotechnology, Springer Berlin Heidelberg, Berlin/Heidelberg, vol. 103, No. 6, Feb. 1, 2019 (Feb. 1, 2019), pp. 2525-2535, XP036746619, ISSN: 0175-7598, DOI: 10.1007/S00253-019-09640-2 [retrieved on Feb. 1, 2019] Whole doc., in particular Fig. 3-5; p. 2531.

(Continued)

*Primary Examiner* — Todd M Epstein

(74) *Attorney, Agent, or Firm* — Morgan, Lewis & Bockius LLP

(57) ABSTRACT

The present disclosure provides methods for genetically modifying microbes to produce a microbe capable of simultaneous consumption of xylose and glucose to increase the productivity output of desired chemical products. The disclosure further provides modified bacteria that are capable of simultaneous consumption of xylose and glucose, and compositions comprising the microbes.

20 Claims, 7 Drawing Sheets

Specification includes a Sequence Listing.

(56) References Cited

OTHER PUBLICATIONS

Sievert, C. et al., "Experimental evolution reveals an effective avenue to release catabolite repression via mutations in XylR", PNAS, vol. 114, No. 28, Jul. 11, 2017, pp. 7349-7354.

Utrilla, J. et al., "Production of D-lactate from sugarcane bagasse and corn stover hydrolysates using metabolic engineered *Escherichia coli* strains", Bioresource Technology, Elsevier, Amsterdam, NL, vol. 220, Aug. 20, 2016 (2-16-08-20), pp. 208-214, XP029734750, ISSN: 0960-8524, DOI: 10.1016/J. BIORTECH.2016.08.067, see introduction; section 2.1; Fig. 2.

Wang, X. et al., "Engineering *E. coli* for simultaneous glucose-xylose utilization during methyl ketone production", Microbial Cell Factories, 2018, 17(12), pp. 1-12.

* cited by examiner

SEQUENCE LISTING

<160> NUMBER OF SEQ ID NOS: 98

<210> SEQ ID NO 1
<211> LENGTH: 1164
<212> TYPE: DNA
<213> ORGANISM: Escherichia coli

<400> SEQUENCE: 1

```
atgaacaact ttaatctgca cacccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaaccccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg gcacattctg     360
caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
tacaccctgc cgccgcgtca ggtggctaac ggcgtagtgg acgcctttgt acacaccgtg     600
gaacagtatg ttaccaaacc ggttgatgcc aaaattcagg accgtttcgc agaaggcatt     660
ttgctgacgc taatcgaaga tggtccgaaa gccctgaaag agccagaaaa ctacgatgtg     720
cgcgccaacg tcatgtgggc ggcgactcag gcgctgaacg gtttgattgg cgctggcgta     780
ccgcaggact gggcaacgca tatgctgggc cacgaactga ctgcgatgca cggtctggat     840
cacgcgcaaa cactggctat cgtcctgcct gcactgtgga atgaaaaacg cgataccaag     900
cgcgctaagc tgctgcaata tgctgaacgc gtctggaaca tcactgaagg ttccgatgat     960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa aatcatgaca ttacgttgga tgtcagccgc    1140
cgtatatacg aagccgcccg ctaa                                           1164
```

<210> SEQ ID NO 2
<211> LENGTH: 387
<212> TYPE: PRT
<213> ORGANISM: Escherichia coli

<400> SEQUENCE: 2

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30
```

```
Leu Ile Thr Tyr Gly Gly Ser Val Lys Thr Gly Val Leu Asp
        35                  40                  45
Gln Val Leu Asp Ala Leu Lys Gly Met Asp Val Leu Glu Phe Gly Gly
 50                  55                  60
Ile Glu Pro Asn Pro Ala Tyr Glu Thr Leu Met Asn Ala Val Lys Leu
 65                  70                  75                  80
Val Arg Glu Gln Lys Val Thr Phe Leu Leu Ala Val Gly Gly Gly Ser
                85                  90                  95
Val Leu Asp Gly Thr Lys Phe Ile Ala Ala Ala Asn Tyr Pro Glu
                100                 105                 110
Asn Ile Asp Pro Trp His Ile Leu Gln Thr Gly Gly Lys Glu Ile Lys
            115                 120                 125
Ser Ala Ile Pro Met Gly Cys Val Leu Thr Leu Pro Ala Thr Gly Ser
130                 135                 140
Glu Ser Asn Ala Gly Ala Val Ile Ser Arg Lys Thr Thr Gly Asp Lys
145                 150                 155                 160
Gln Ala Phe His Ser Ala His Val Gln Pro Val Phe Ala Val Leu Asp
                165                 170                 175
Pro Val Tyr Thr Tyr Thr Leu Pro Pro Arg Gln Val Ala Asn Gly Val
            180                 185                 190
Val Asp Ala Phe Val His Thr Val Glu Gln Tyr Val Thr Lys Pro Val
        195                 200                 205
Asp Ala Lys Ile Gln Asp Arg Phe Ala Glu Gly Ile Leu Leu Thr Leu
210                 215                 220
Ile Glu Asp Gly Pro Lys Ala Leu Lys Glu Pro Glu Asn Tyr Asp Val
225                 230                 235                 240
Arg Ala Asn Val Met Trp Ala Ala Thr Gln Ala Leu Asn Gly Leu Ile
                245                 250                 255
Gly Ala Gly Val Pro Gln Asp Trp Ala Thr His Met Leu Gly His Glu
            260                 265                 270
Leu Thr Ala Met His Gly Leu Asp His Ala Gln Thr Leu Ala Ile Val
        275                 280                 285
Leu Pro Ala Leu Trp Asn Glu Lys Arg Asp Thr Lys Arg Ala Lys Leu
    290                 295                 300
Leu Gln Tyr Ala Glu Arg Val Trp Asn Ile Thr Glu Gly Ser Asp Asp
305                 310                 315                 320
Glu Arg Ile Asp Ala Ala Ile Ala Ala Thr Arg Asn Phe Phe Glu Gln
                325                 330                 335
Leu Gly Val Pro Thr His Leu Ser Asp Tyr Gly Leu Asp Gly Ser Ser
            340                 345                 350
Ile Pro Ala Leu Leu Lys Lys Leu Glu Glu His Gly Met Thr Gln Leu
        355                 360                 365
Gly Glu Asn His Asp Ile Thr Leu Asp Val Ser Arg Arg Ile Tyr Glu
370                 375                 380
Ala Ala Arg
385

<210> SEQ ID NO 3
<211> LENGTH: 1440
<212> TYPE: DNA
<213> ORGANISM: Escherichia coli

<400> SEQUENCE: 3
atgtcagtac ccgttcaaca tcctatgtat atcgatggac agtttgttac ctggcgtgga    60
```

```
gacgcatgga ttgatgtggt aaaccctgct acagaggctg tcatttcccg catacccgat    120
ggtcaggccg aggatgcccg taaggcaatc gatgcagcag aacgtgcaca accagaatgg    180
gaagcgttgc ctgctattga acgcgccagt tggttgcgca aaatctccgc cgggatccgc    240
gaacgcgcca gtgaaatcag tgcgctgatt gttgaagaag ggggcaagat ccagcagctg    300
gctgaagtcg aagtggcttt tactgccgac tatatcgatt acatggcgga gtgggcacgg    360
cgttacgagg gcgagattat tcaaagcgat cgtccaggag aaaatattct tttgtttaaa    420
cgtgcgcttg gtgtgactac cggcattctg ccgtggaact ccccgttctt cctcattgcc    480
cgcaaaatgg ctcccgctct tttgaccggt aataccatcg tcattaaacc tagtgaattt    540
acgccaaaca atgcgattgc attcgccaaa atcgtcgatg aaataggcct tccgcgcggc    600
gtgtttaacc ttgtactggg gcgtggtgaa accgttgggc aagaactggc gggtaaccca    660
aaggtcgcaa tggtcagtat gacaggcagc gtctctgcag gtgagaagat catggcgact    720
gcggcgaaaa acatcaccaa agtgtgtctg gaattggggg gtaaagcacc agctatcgta    780
atggacgatg ccgatcttga actggcagtc aaagccatcg ttgattcacg cgtcattaat    840
agtgggcaag tgtgtaactg tgcagaacgt gtttatgtac agaaaggcat ttatgatcag    900
ttcgtcaatc ggctgggtga agcgatgcag gcggttcaat ttggtaaccc cgctgaacgc    960
aacgacattg cgatggggcc gttgattaac gccgcggcgc tggaaagggt cgagcaaaaa   1020
gtggcgcgcg cagtagaaga aggggcgaga gtggcgttcg gtggcaaagc ggtagagggg   1080
aaaggatatt attatccgcc gacattgctg ctggatgttc gccaggaaat gtcgattatg   1140
catgaggaaa cctttggccc ggtgctgcca gttgtcgcat ttgacacgct ggaagatgct   1200
atctcaatgg ctaatgacag tgattacggc ctgacctcat caatctatac ccaaaatctg   1260
aacgtcgcga tgaaagccat taagggctga agtttggtg aaacttacat caaccgtgaa    1320
aacttcgaag ctatgcaagg cttccacgcc ggatggcgta atccggtat ggcggcgca     1380
gatggtaaac atggcttgca tgaatatctg cagacccagg tggtttattt acagtcttaa   1440
```

<210> SEQ ID NO 4
<211> LENGTH: 479
<212> TYPE: PRT
<213> ORGANISM: Escherichia coli

<400> SEQUENCE: 4

Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

| | | | | | | | | | | | |
|---|---|---|---|---|---|---|---|---|---|---|---|
|Ser|Asp|Arg|Pro|Gly|Glu|Asn|Ile|Leu|Leu|Phe|Lys|Arg|Ala|Leu|Gly|
|130| | | | |135| | | | |140| | | | | |

Ser Asp Arg Pro Gly Glu Asn Ile Leu Leu Phe Lys Arg Ala Leu Gly
130                 135                 140

Val Thr Thr Gly Ile Leu Pro Trp Asn Phe Pro Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
                180                 185                 190

Asp Glu Ile Gly Leu Pro Arg Gly Val Phe Asn Leu Val Leu Gly Arg
                195                 200                 205

Gly Glu Thr Val Gly Gln Glu Leu Ala Gly Asn Pro Lys Val Ala Met
210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
                260                 265                 270

Ile Val Asp Ser Arg Val Ile Asn Ser Gly Gln Val Cys Asn Cys Ala
                275                 280                 285

Glu Arg Val Tyr Val Gln Lys Gly Ile Tyr Asp Gln Phe Val Asn Arg
290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
                325                 330                 335

Val Glu Gln Lys Val Ala Arg Ala Val Glu Glu Gly Ala Arg Val Ala
                340                 345                 350

Phe Gly Gly Lys Ala Val Glu Gly Lys Gly Tyr Tyr Pro Pro Thr
                355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
                420                 425                 430

Gly Glu Thr Tyr Ile Asn Arg Glu Asn Phe Glu Ala Met Gln Gly Phe
                435                 440                 445

His Ala Gly Trp Arg Lys Ser Gly Ile Gly Gly Ala Asp Gly Lys His
450                 455                 460

Gly Leu His Glu Tyr Leu Gln Thr Gln Val Val Tyr Leu Gln Ser
465                 470                 475

<210> SEQ ID NO 5
<211> LENGTH: 1323
<212> TYPE: DNA
<213> ORGANISM: Escherichia coli

<400> SEQUENCE: 5
atgcaagcct attttgacca gctcgatcgc gttcgttatg aaggctcaaa atcctcaaac        60
ccgttagcat tccgtcacta caatcccgac gaactggtgt tgggtaagcg tatggaagag       120
cacttgcgtt ttgccgcctg ctactggcac accttctgct ggaacggggc ggatatgttt       180

-continued

```
ggtgtggggg cgtttaatcg tccgtggcag cagcctggtg aggcactggc gttggcgaag    240
cgtaaagcag atgtcgcatt tgagtttttc cacaagttac atgtgccatt ttattgcttc    300
cacgatgtgg atgtttcccc tgagggcgcg tcgttaaaag agtacatcaa taattttgcg    360
caaatggttg atgtcctggc aggcaagcaa gaagagagcg gcgtgaagct gctgtgggga    420
acggccaact gctttacaaa ccctcgctac ggcgcgggtg cggcgacgaa cccagatcct    480
gaagtcttca gctgggcggc aacgcaagtt gttacagcga tggaagcaac ccataaattg    540
ggcggtgaaa actatgtcct gtggggcggt cgtgaaggtt acgaaacgct gttaaatacc    600
gacttgcgtc aggagcgtga acaactgggc cgctttatgc agatggtggt tgagcataaa    660
cataaaatcg gtttccaggg cacgttgctt atcgaaccga accgcaaga accgaccaaa    720 catcaatatg attacgatgc cgcgacggtc tatggcttcc tgaaacagtt tggtctggaa    780
aaagagatta aactgaacat tgaagctaac cacgcgacgc tggcaggtca ctctttccat    840
catgaaatag ccaccgccat tgcgcttggc ctgttcggtt ctgtcgacgc caaccgtggc    900
gatgcgcaac tgggctggga caccgaccag ttcccgaaca gtgtggaaga gaatgcgctg    960
gtgatgtatg aaattctcaa agcaggcggt tcaccaccg tggtctgaa cttcgatgcc     1020 aaagtacgtc gtcaaagtac tgataaatat gatctgtttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat gggccagca atcctgaaa    1200 ggccaaatgt cactggcaga tttagccaaa tatgctcagg aacatcattt gtctccggtg    1260
catcagagtg gtcgccagga acaactggaa atctggtaa accattatct gttcgacaaa    1320
taa                                                                  1323
```

<210> SEQ ID NO 6
<211> LENGTH: 440
<212> TYPE: PRT
<213> ORGANISM: Escherichia coli

<400> SEQUENCE: 6

```
Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160
```

```
Glu Val Phe Ser Trp Ala Ala Thr Gln Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
    370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
                405                 410                 415

Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 7
<211> LENGTH: 1179
<212> TYPE: DNA
<213> ORGANISM: Escherichia coli

<400> SEQUENCE: 7
atgtttacta aacgtcaccg catcacatta ctgttcaatg ccaataaagc ctatgaccgg      60
caggtagtag aaggcgtagg ggaatattta caggcgtcac aatcggaatg ggatattttc    120
attgaagaag atttccgcgc cgcattgat aaaatcaagg actggttagg agatggcgtc    180
attgccgact tcgacgacaa acagatcgag caagcgctgg ctgatgtcga cgtccccatt    240
gttggggttg gcggctcgta tcaccttgca gaaagttacc cacccgttca ttacattgcc    300
accgataact atgcgctggt tgaaagcgca ttttgcatt taaaagagaa aggcgttaac    360
cgctttgctt tttatggtct tccggaatca agcggcaaac gttgggccac tgagcgcgaa    420
tatgcatttc gtcagcttgt cgccgaagaa agtatcgcg gagtggttta tcaggggtta    480
gaaaccgcgc cagagaactg gcaacacgcg caaaatcggc tggcagactg gctacaaacg    540
```

-continued

```
ctaccaccgc aaaccgggat tattgccgtt actgacgccc gagcgcggca tattctgcaa    600
gtatgtgaac atctacatat tcccgtaccg gaaaaattat gcgtgattgg catcgataac    660
gaagaactga cccgctatct gtcgcgtgtc gccctttctt cggtcgctca gggcgcgcgg    720
caaatgggct atcaggcggc aaaactgttg catcgattat tagataaaga agaaatgccg    780
ctacagcgaa ttttggtccc accagttcgc gtcattgaac ggcgctcaac agattatcgc    840
tcgctgaccg atcccgccgt tattcaggcc atgcattaca ttcgtaatca cgcctgtaaa    900
gggattaaag tggatcaggt actggatgcg gtcgggatct cgcgctccaa tcttgagaag    960
cgttttaaag aagaggtggg tgaaaccatc catgccatga ttcatgccga aagctggag    1020
aaagcgcgca gtctgctgat ttcaaccacc ttgtcgatca atgagatatc gcaaatgtgc    1080
ggttatccat cgctgcaata tttctactct gtttttaaaa aagcatatga cacgacgcca    1140
aaagagtatc gcgatgtaaa tagcgaggtc atgttgtag                          1179
```

<210> SEQ ID NO 8
<211> LENGTH: 392
<212> TYPE: PRT
<213> ORGANISM: Escherichia coli

<400> SEQUENCE: 8

```
Met Phe Thr Lys Arg His Arg Ile Thr Leu Leu Phe Asn Ala Asn Lys
1               5                   10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
    50                  55                  60

Asp Asp Lys Gln Ile Glu Gln Ala Leu Ala Asp Val Asp Val Pro Ile
65                  70                  75                  80

Val Gly Val Gly Gly Ser Tyr His Leu Ala Glu Ser Tyr Pro Pro Val
                85                  90                  95

His Tyr Ile Ala Thr Asp Asn Tyr Ala Leu Val Glu Ser Ala Phe Leu
            100                 105                 110

His Leu Lys Glu Lys Gly Val Asn Arg Phe Ala Phe Tyr Gly Leu Pro
        115                 120                 125

Glu Ser Ser Gly Lys Arg Trp Ala Thr Glu Arg Glu Tyr Ala Phe Arg
    130                 135                 140

Gln Leu Val Ala Glu Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

Ala Arg Ala Arg His Ile Leu Gln Val Cys Glu His Leu His Ile Pro
        195                 200                 205

Val Pro Glu Lys Leu Cys Val Ile Gly Ile Asp Asn Glu Glu Leu Thr
    210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
                245                 250                 255
```

```
Glu Glu Met Pro Leu Gln Arg Ile Leu Val Pro Val Arg Val Ile
            260                 265                 270

Glu Arg Arg Ser Thr Asp Tyr Arg Ser Leu Thr Asp Pro Ala Val Ile
        275                 280                 285

Gln Ala Met His Tyr Ile Arg Asn His Ala Cys Lys Gly Ile Lys Val
        290                 295                 300

Asp Gln Val Leu Asp Ala Val Gly Ile Ser Arg Ser Asn Leu Glu Lys
305                 310                 315                 320

Arg Phe Lys Glu Glu Val Gly Glu Thr Ile His Ala Met Ile His Ala
                325                 330                 335

Glu Lys Leu Glu Lys Ala Arg Ser Leu Leu Ile Ser Thr Thr Leu Ser
            340                 345                 350

Ile Asn Glu Ile Ser Gln Met Cys Gly Tyr Pro Ser Leu Gln Tyr Phe
            355                 360                 365

Tyr Ser Val Phe Lys Lys Ala Tyr Asp Thr Thr Pro Lys Glu Tyr Arg
        370                 375                 380

Asp Val Asn Ser Glu Val Met Leu
385                 390

<210> SEQ ID NO 9
<211> LENGTH: 633
<212> TYPE: DNA
<213> ORGANISM: Escherichia coli

<400> SEQUENCE: 9
atggtgcttg gcaaaccgca aacagacccg actctcgaat ggttcttgtc tcattgccac      60
attcataagt acccatccaa gagcacgctt attcaccagg gtgaaaaagc ggaaacgctg     120
tactacatcg ttaaaggctc tgtggcagtg ctgatcaaag acgaagaggg taaagaaatg     180
atcctctcct atctgaatca gggtgatttt attggcgaac tgggcctgtt tgaagagggc     240
caggaacgta gcgcatgggt acgtgcgaaa accgcctgtg aagtggctga aatttcgtac     300
aaaaaatttc gccaattgat tcaggtaaac ccggacattc tgatgcgttt gtctgcacag     360
atggcgcgtc gtctgcaagt cacttcagag aaagtgggca acctggcgtt cctcgacgtg     420
acgggccgca ttgcacagac tctgctgaat ctggcaaaac aaccagacgc tatgactcac     480
ccggacggta tgcaaatcaa aattacccgt caggaaattg gtcagattgt cggctgttct     540
cgtgaaaccg tgggacgcat tctgaagatg ctggaagatc agaacctgat ctccgcacac     600
ggtaaaacca tcgtcgttta cggcactcgt taa                                  633

<210> SEQ ID NO 10
<211> LENGTH: 210
<212> TYPE: PRT
<213> ORGANISM: Escherichia coli

<400> SEQUENCE: 10

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80
```

```
Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210
```

<210> SEQ ID NO 11
<211> LENGTH: 897
<212> TYPE: DNA
<213> ORGANISM: Homo sapiens

<400> SEQUENCE: 11

```
atggaggaaa agcaaattct gtgcgttggt ctggtggttc tggacgtgat tagcctggtt      60
gataagtacc cgaaagagga tagcgaaatc cgttgcctga ccagcgttg  gcaacgtggt     120
ggcaacgcga gcaatagctg caccgttctg agcctgctgg gtgcgccgtg cgcgttcatg     180
ggtagcatgg cgccgggtca tgttgcggac ttcctggtgg cggattttcg tcgtcgtggt     240
gtggacgtta gccaggttgc gtggcaaagc aagggcgata ccccgagctc ctgctgcatc     300
attaacaaca gcaacggtaa ccgtaccatt gtgctgcacg acaccagcct gccggatgtt     360
agcgcgaccg acttcgagaa ggtggatctg acccagtttt aatggattca cattgagggc     420
cgtaacgcga gcgaacaggt taaaatgctg caacgtattg atgcgcacaa cacccgtcag     480
ccgccggaac aaaagattcg tgtgagcgtt gaggtgaaaa accgcgtga ggaactgttc      540
caactgtttg gttacggcga cgtggttttc gttagcaagg atgtggcgaa cacctgggt      600
tttcaaagcg cggaggaagc gctgcgtggt ctgtatggcc gtgtgcgtaa aggcgcggtt     660
ctggtgtgcg cgtgggcgga ggaaggcgcg gatgcgctgg gtccggatgg caaactgctg     720
cacagcgatg cgttcccgcc gccgcgtgtg gttgacaccc tgggtgcggg cgataccttc     780
aacgcgagcg ttatctttag cctgagccag ggccgtagcg tgcaagaggc gctgcgtttc     840
ggctgccaag ttgcgggtaa aaaatgcggt ctgcaaggct ttgacggtat cgtgtaa       897
```

<210> SEQ ID NO 12
<211> LENGTH: 298
<212> TYPE: PRT
<213> ORGANISM: Homo sapiens

<400> SEQUENCE: 12

```
Met Glu Glu Lys Gln Ile Leu Cys Val Gly Leu Val Val Leu Asp Val
1               5                   10                  15

Ile Ser Leu Val Asp Lys Tyr Pro Lys Glu Asp Ser Glu Ile Arg Cys
            20                  25                  30
```

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
 50                  55                  60

Pro Gly His Val Ala Asp Phe Leu Val Ala Asp Phe Arg Arg Arg Gly
 65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
                100                 105                 110

His Asp Thr Ser Leu Pro Asp Val Ser Ala Thr Asp Phe Glu Lys Val
                115                 120                 125

Asp Leu Thr Gln Phe Lys Trp Ile His Ile Glu Gly Arg Asn Ala Ser
        130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
                180                 185                 190

Lys Asp Val Ala Lys His Leu Gly Phe Gln Ser Ala Glu Glu Ala Leu
                195                 200                 205

Arg Gly Leu Tyr Gly Arg Val Arg Lys Gly Ala Val Leu Val Cys Ala
        210                 215                 220

Trp Ala Glu Glu Gly Ala Asp Ala Leu Gly Pro Asp Gly Lys Leu Leu
225                 230                 235                 240

His Ser Asp Ala Phe Pro Pro Arg Val Val Asp Thr Leu Gly Ala
                245                 250                 255

Gly Asp Thr Phe Asn Ala Ser Val Ile Phe Ser Leu Ser Gln Gly Arg
                260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
        290                 295

<210> SEQ ID NO 13
<211> LENGTH: 1455
<212> TYPE: DNA
<213> ORGANISM: Escherichia coli

<400> SEQUENCE: 13
atgtatatcg gatagatct tggcacctcg ggcgtaaaag ttattttgct caacgagcag      60
ggtgaggtgg ttgctgcgca acggaaaag ctgaccgttt cgcgcccgca tccactctgg    120
tcggaacaag acccggaaca gtggtggcag gcaactgatc gcgcaatgaa agctctgggc    180
gatcagcatt ctctgcagga cgttaaagca ttgggtattg ccggccagat gcacggagca    240
accttgctgg atgctcagca acgggtgtta cgccctgcca ttttgtggaa cgacgggcgc    300
tgtgcgcaag agtgcacttt gctggaagcg cgagttccgc aatcgcgggt gattaccggc    360
aacctgatga tgcccggatt tactgcgcct aaattgctat gggttcagcg gcatgagccg    420
gagatattcc gtcaaatcga caaagtatta ttaccgaaag attacttgcg tctgcgtatg    480
acgggggagt tgccagcgca tatgtctgac gcagctggca ccatgtggct ggatgtcgca    540
aagcgtgact ggagtgacgt catgctgcag gcttgcgact tatctcgtga ccagatgccc    600

-continued

```
gcattatacg aaggcagcga aattactggt gctttgttac ctgaagttgc gaaagcgtgg      660
ggtatggcga cggtgccagt tgtcgcaggc ggtggcgaca atgcagctgg tgcagttggt      720
gtgggaatgg ttgatgctaa tcaggcaatg ttatcgctgg ggacgtcggg ggtctatttt      780
gctgtcagcg aagggttctt aagcaagcca gaaagcgccg tacatagctt ttgccatgcg      840
ctaccgcaac gttggcattt aatgtctgtg atgctgagtg cagcgtcgtg tctggattgg      900
gccgcgaaat taaccggcct gagcaatgtc ccagctttaa tcgctgcagc tcaacaggct      960
gatgaaagtg ccgagccagt ttggtttctg ccttatcttt ccggcgagcg tacgccacac     1020
aataatcccc aggcgaaggg ggttttcttt ggtttgactc atcaacatgg ccccaatgaa     1080
ctggcgcgag cagtgctgga aggcgtgggt tatgcgctgg cagatggcat ggatgtcgtg     1140
catgcctgcg gtattaaacc gcaaagtgtt acgttgattg ggggcggggc gcgtagtgag     1200
tactggcgtc agatgctggc ggatatcagc ggtcagcagc tcgattaccg tacgggggg      1260 gatgtggggc cagcactggg cgcagcaagg ctggcgcaga tcgcggcgaa tccagagaaa     1320
tcgctcattg aattgttgcc gcaactaccg ttagaacagt cgcatctacc agatgcgcag     1380
cgttatgccg cttatcagcc acgacgagaa acgttccgtc gcctctatca gcaacttctg     1440
ccattaatgg cgtaa                                                       1455
```

<210> SEQ ID NO 14
<211> LENGTH: 484
<212> TYPE: PRT
<213> ORGANISM: Escherichia coli

<400> SEQUENCE: 14

```
Met Tyr Ile Gly Ile Asp Leu Gly Thr Ser Gly Val Lys Val Ile Leu
1               5                   10                  15

Leu Asn Glu Gln Gly Glu Val Val Ala Ala Gln Thr Glu Lys Leu Thr
                20                  25                  30

Val Ser Arg Pro His Pro Leu Trp Ser Glu Gln Asp Pro Glu Gln Trp
            35                  40                  45

Trp Gln Ala Thr Asp Arg Ala Met Lys Ala Leu Gly Asp Gln His Ser
        50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
                100                 105                 110

Pro Gln Ser Arg Val Ile Thr Gly Asn Leu Met Met Pro Gly Phe Thr
            115                 120                 125

Ala Pro Lys Leu Leu Trp Val Gln Arg His Glu Pro Glu Ile Phe Arg
        130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
```

Val Pro Val Ala Gly Gly Asp Asn Ala Gly Ala Val Gly
225                 230                 235                 240

Val Gly Met Val Asp Ala Asn Gln Ala Met Leu Ser Leu Gly Thr Ser
            245                 250                 255

Gly Val Tyr Phe Ala Val Ser Glu Gly Phe Leu Ser Lys Pro Glu Ser
                260                 265                 270

Ala Val His Ser Phe Cys His Ala Leu Pro Gln Arg Trp His Leu Met
            275                 280                 285

Ser Val Met Leu Ser Ala Ser Cys Leu Asp Trp Ala Ala Lys Leu
        290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
                340                 345                 350

Thr His Gln His Gly Pro Asn Glu Leu Ala Arg Ala Val Leu Glu Gly
            355                 360                 365

Val Gly Tyr Ala Leu Ala Asp Gly Met Asp Val Val His Ala Cys Gly
370                 375                 380

Ile Lys Pro Gln Ser Val Thr Leu Ile Gly Gly Ala Arg Ser Glu
385                 390                 395                 400

Tyr Trp Arg Gln Met Leu Ala Asp Ile Ser Gly Gln Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
            435                 440                 445

Leu Pro Leu Glu Gln Ser His Leu Pro Asp Ala Gln Arg Tyr Ala Ala
        450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 15
<211> LENGTH: 747
<212> TYPE: DNA
<213> ORGANISM: Caulobacter crescentus

<400> SEQUENCE: 15
atgagcagcg cgatctaccc gagcctgaaa ggtaaacgtg tggtgattac cggcggcggc      60
agcggcattg gtgcgggcct gaccgcgggc ttcgcgcgtc agggtgcgga agtgatcttt     120
ctggacattg cggacgaaga tagccgtgcg ctggaggcgg aactggcggg cagcccgatc     180
ccgccggtgt acaagcgttg cgatctgatg aacctggagg cgatcaaagc ggttttcgcg     240
gaaattggcg acgtggatgt tctggtgaac aacgcgggta cgacgaccg tcacaagctg      300 gcggatgtga ccgtgcgta ttgggatgag cgtattaacg ttaacctgcg tcacatgctg     360
ttctgcaccc aggcggtggc gccgggtatg aagaaacgtg gtggcggtgc ggttatcaac     420
tttggcagca ttagctggca cctgggtctg gaggacctgg tgctgtacga aaccgcgaaa     480
gcgggcatca gggtatgac ccgtgcgctg gcgcgtgaac tgggtccgga cgatattcgt      540
gtgacctgcg tggttccggg taacgttaag accaaacgtc aagagaagtg gtatacccccg    600

```
gagggtgaag cgcagattgt tgcggcgcaa tgcctgaaag gtcgtattgt tccggaaaac    660
gtggcggcgc tggttctgtt tctggcgagc gatgatgcga gcctgtgcac cggccatgag    720
tattggattg atgcgggctg gcgttaa                                        747
```

<210> SEQ ID NO 16
<211> LENGTH: 248
<212> TYPE: PRT
<213> ORGANISM: Caulobacter crescentus

<400> SEQUENCE: 16

```
Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
        195                 200                 205

Ala Gln Cys Leu Lys Gly Arg Ile Val Pro Glu Asn Val Ala Ala Leu
    210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245
```

<210> SEQ ID NO 17
<211> LENGTH: 255
<212> TYPE: PRT
<213> ORGANISM: Burkholderia xenovorans

<400> SEQUENCE: 17

```
Met Ser Tyr Ala Ile Tyr Pro Ser Leu Ser Gly Lys Thr Val Val Ile
1               5                   10                  15

Thr Gly Gly Gly Ser Gly Ile Gly Ala Ala Met Val Glu Ala Phe Ala
            20                  25                  30

Arg Gln Gly Ala Arg Val Phe Leu Asp Val Ala Glu Asp Asp Ser
        35                  40                  45
```

```
Leu Ala Leu Gln Gln Ser Leu Ser Asp Ala Pro His Pro Pro Leu Phe
    50                  55                  60

Arg Arg Cys Asp Leu Arg Ser Val Asp Ala Ile His Ser Ala Phe Ala
65                  70                  75                  80

Gly Ile Val Glu Ile Ala Gly Pro Ile Glu Val Leu Val Asn Asn Ala
                85                  90                  95

Gly Asn Asp Asp Arg His Glu Val Asp Ala Ile Thr Pro Ala Tyr Trp
                100                 105                 110

Asp Glu Arg Met Ala Val Asn Leu Arg His Gln Phe Phe Cys Ala Gln
            115                 120                 125

Ala Ala Ala Ala Gly Met Arg Lys Ile Gly Arg Gly Val Ile Leu Asn
130                 135                 140

Leu Gly Ser Val Ser Trp His Leu Ala Leu Pro Asn Leu Ala Ile Tyr
145                 150                 155                 160

Met Ser Ala Lys Ala Gly Ile Glu Gly Leu Thr Arg Gly Leu Ala Arg
                165                 170                 175

Asp Leu Gly Ala Ala Gly Ile Arg Val Asn Cys Ile Ile Pro Gly Ala
                180                 185                 190

Val Arg Thr Pro Arg Gln Met Gln Leu Trp Gln Ser Pro Glu Ser Glu
            195                 200                 205

Ala Lys Leu Val Ala Ser Gln Cys Leu Arg Leu Arg Ile Glu Pro Glu
210                 215                 220

His Val Ala Arg Met Ala Leu Phe Leu Ala Ser Asp Ala Ser Arg
225                 230                 235                 240

Cys Ser Gly Arg Asp Tyr Phe Val Asp Ala Gly Trp Tyr Gly Glu
                245                 250                 255

<210> SEQ ID NO 18
<211> LENGTH: 1173
<212> TYPE: DNA
<213> ORGANISM: Haloferax volcanii

<400> SEQUENCE: 18
atgagccccg cccccaccga catcgtcgag gagttcacgc gccgcgactg gcagggagac     60
gacgtgacgg gcaccgtgcg ggtcgccatg atcggcctcg gctggtggac ccgcgacgag    120
gcgattcccg cggtcgaggc gtccgagttc tgcgagacga cggtcgtcgt cagcagttcg    180
aaggagaaag ccgagggcgc gacggcgttg accgagtcga taacccacgg cctcacctac    240
gacgagttcc acgaggggt cgccgccgac gcctacgacg cggtgtacgt cgtcacgccg    300
aacggtctgc atctcccgta cgtcgagacc gccgccgagt tggggaaggc ggtcctctgc    360
gagaaaccgc tggaagcgtc ggtcgagcgg gccgaaaagc tcgtcgccgc ctgcgaccgc    420
gccgacgtgc ccctgatggt cgcctatcgg atgcagaccg agccggccgt ccggcgcgcc    480
cgcgaactcg tcgaggccgg cgtcatcggc gagccggtgt cgtccacgg ccacatgtcc    540 cagcgcctgc tcgacgaggt cgtccccgac cccgaccagt ggcggctcga ccccgaactc    600
tccggcggcg cgaccgtcat ggacatcggg ctctacccgc tgaacaccgc ccggttcgtc    660
ctcgacgccg accccgtccg cgtcaggcg accgccgcg tcgacgacga ggcgttcgag    720
gccgtcggcg acgagcacgt cagtttcggc gtcgacttcg acgacggcac gctcgcggtc    780
tgcaccgcca ccagtcggc ttaccagttg agccacctcc gggtgaccgg caccgagggc    840
gaactcgaaa tcgagcccgc gttctacaac cgccaaaagc ggggattccg actgtcgtgg    900
ggggaccagt ccgccgacta cgacttcgag caggtaaacc agatgacgga ggagttcgac    960
```

```
tacttcgcgt cccggctcct gtcggattcc gaccccgcgc cgacggcga ccacgcgctc    1020 gtggacatgc gcgcgatgga cgcgatttac gccgcggcgg agcgcgggac cgatgtcgcc    1080
gtcgacgccg ccgactccga ttccgccgac tccgattccg ccgacgctgc cgccgccaac    1140
cacgacgccg accccgattc cgacgggacg tag                                 1173
```

<210> SEQ ID NO 19
<211> LENGTH: 390
<212> TYPE: PRT
<213> ORGANISM: Haloferax volcanii

<400> SEQUENCE: 19

```
Met Ser Pro Ala Pro Thr Asp Ile Val Glu Glu Phe Thr Arg Arg Asp
1               5                   10                  15

Trp Gln Gly Asp Asp Val Thr Gly Thr Val Arg Val Ala Met Ile Gly
            20                  25                  30

Leu Gly Trp Trp Thr Arg Asp Glu Ala Ile Pro Ala Val Glu Ala Ser
        35                  40                  45

Glu Phe Cys Glu Thr Thr Val Val Ser Ser Lys Glu Lys Ala
    50                  55                  60

Glu Gly Ala Thr Ala Leu Thr Glu Ser Ile Thr His Gly Leu Thr Tyr
65                  70                  75                  80

Asp Glu Phe His Glu Gly Val Ala Ala Asp Ala Tyr Asp Ala Val Tyr
                85                  90                  95

Val Val Thr Pro Asn Gly Leu His Leu Pro Tyr Val Glu Thr Ala Ala
            100                 105                 110

Glu Leu Gly Lys Ala Val Leu Cys Glu Lys Pro Leu Glu Ala Ser Val
        115                 120                 125

Glu Arg Ala Glu Lys Leu Val Ala Cys Asp Arg Ala Asp Val Pro
    130                 135                 140

Leu Met Val Ala Tyr Arg Met Gln Thr Glu Pro Ala Val Arg Arg Ala
145                 150                 155                 160

Arg Glu Leu Val Glu Ala Gly Val Ile Gly Glu Pro Val Phe Val His
                165                 170                 175

Gly His Met Ser Gln Arg Leu Leu Asp Glu Val Val Pro Asp Pro Asp
            180                 185                 190

Gln Trp Arg Leu Asp Pro Glu Leu Ser Gly Gly Ala Thr Val Met Asp
        195                 200                 205

Ile Gly Leu Tyr Pro Leu Asn Thr Ala Arg Phe Val Leu Asp Ala Asp
    210                 215                 220

Pro Val Arg Val Arg Ala Thr Ala Arg Val Asp Asp Glu Ala Phe Glu
225                 230                 235                 240

Ala Val Gly Asp Glu His Val Ser Phe Gly Val Asp Phe Asp Asp Gly
                245                 250                 255

Thr Leu Ala Val Cys Thr Ala Ser Gln Ser Ala Tyr Gln Leu Ser His
            260                 265                 270

Leu Arg Val Thr Gly Thr Glu Gly Glu Leu Glu Ile Glu Pro Ala Phe
        275                 280                 285

Tyr Asn Arg Gln Lys Arg Gly Phe Arg Leu Ser Trp Gly Asp Gln Ser
    290                 295                 300

Ala Asp Tyr Asp Phe Glu Gln Val Asn Gln Met Thr Glu Glu Phe Asp
305                 310                 315                 320

Tyr Phe Ala Ser Arg Leu Leu Ser Asp Ser Asp Pro Ala Pro Asp Gly
                325                 330                 335
```

Asp His Ala Leu Val Asp Met Arg Ala Met Asp Ala Ile Tyr Ala Ala
            340                 345                 350

Ala Glu Arg Gly Thr Asp Val Ala Val Asp Ala Ala Asp Ser Asp Ser
        355                 360                 365

Ala Asp Ser Asp Ser Ala Asp Ala Ala Ala Asn His Asp Ala Asp
    370                 375                 380

Pro Asp Ser Asp Gly Thr
385                 390

<210> SEQ ID NO 20
<211> LENGTH: 990
<212> TYPE: DNA
<213> ORGANISM: Escherichia coli

<400> SEQUENCE: 20

| | |
|---|---|
| atgcacaaat tactaaagc cctggcagcc attggtctgg cagccgttat gtcacaatcc | 60 |
| gctatggcgg agaacctgaa gctcggtttt ctggtgaagc aaccggaaga gccgtggttc | 120 |
| cagaccgaat ggaagtttgc cgataaagcc gggaaggatt tagggtttga ggttattaag | 180 |
| attgccgtgc cggatggcga aaaaacattg aacgcgatcg acagcctggc tgccagtggc | 240 |
| gcaaaaggtt tcgttatttg tactccggac cccaaactcg ctctgccat cgtcgcgaaa | 300 |
| gcgcgtggct acgatatgaa agtcattgcc gtggatgacc agtttgttaa cgccaaaggt | 360 |
| aagccaatgg ataccgttcc gctggtgatg atggcggcga ctaaaattgg cgaacgtcag | 420 |
| ggccaggaac tgtataaaga gatgcagaaa cgtggctggg atgtcaaaga aagcgcggtg | 480 |
| atggcgatta ccgccaacga actggatacc gcccgccgcc gtactacggg atctatggat | 540 |
| gcgctgaaag cggccggatt cccggaaaaa caatttatc aggtacctac caaatctaac | 600 |
| gacatcccgg gggcatttga cgctgccaac tcaatgctgg ttcaacatcc ggaagttaaa | 660 |
| cattggctga tcgtcggtat gaacgacagc accgtgctgg cggcgtacg cgcgacggaa | 720 |
| ggtcagggct ttaaagcggc cgatatcatc ggcattggca ttaacggtgt ggatgcggtg | 780 |
| agcgaactgt ctaaagcaca ggcaaccggc ttctacggtt ccctgctgcc aagcccggac | 840 |
| gtacatggct ataaatccag cgaaatgctt tacaactggg tagcaaaaga cgttgaaccg | 900 |
| ccaaaattta ccgaagttac cgacgtggta ctgatcacgc gtgacaactt taagaagaa | 960 |
| ctggagaaaa aaggtttagg cggtaagtaa | 990 |

<210> SEQ ID NO 21
<211> LENGTH: 1515
<212> TYPE: DNA
<213> ORGANISM: Escherichia coli

<400> SEQUENCE: 21

| | |
|---|---|
| atgcaacagt ctaccccgta tctctcattt cgcggcatcg gtaaaacgtt tccggcgtt | 60 |
| aaggcgctga cggatattag ttttgactgc tatgccggtc aggttcatgc gttgatgggt | 120 |
| gaaaatggcg caggaaaatc aactctctta aaaatcctca gcggcaacta tgcgccaacc | 180 |
| acgggttctg tagtgattaa tgggcaggaa atgtcctttt ccgacacgac cgcagcactt | 240 |
| aacgcgggcg tggcgattat ttaccaggaa ctgcatctcg tgccggaaat gaccgtcgcg | 300 |
| gaaacatctc atctcggcca gctgccgcat aaaggcggca ttgtgaatcg ctcattgctg | 360 |
| aattatgagg cgggtttaca acttaaacat cttggtatgg atattgaccc ggacacgccg | 420 |
| ctgaaatatc tctccattgg tcagtggcag atggttgaaa tcgccaaagc gctggcgcgt | 480 |

|  |  |
|---|---|
| aacgccaaaa ttatcgcctt tgatgagcca accagctccc tctctgcccg tgaaatcgac | 540 |
| aatcttttcc gcgttattcg tgaactgcga aagaggggc gggtaatctt atacgtttct | 600 |
| caccgtatgg aagaaatatt tgccctcagc gatgccatta ctgtctttaa agatggacgt | 660 |
| tatgtcaaaa cctttaccga tatgcagcag gttgaccacg acgcgctggt gcaggcgatg | 720 |
| gtcgggcgcg acattggcga tatctacggc tggcaaccgc gtagttatgg cgaggagcgc | 780 |
| ctacgtcttg atgctgtgaa agcaccaggc gtgcgtacgc caataagtct ggcggttcgc | 840 |
| agtggtgaaa ttgttgggct gtttggtctg gtaggggcgg ggcgtagcga attaatgaaa | 900 |
| ggcatgtttg gcgggacgca aatcaccgcc ggtcaggttt atatcgacca acagccgatc | 960 |
| gatattcgta aaccgagcca cgccattgcc gcaggcatga tgctctgccc ggaagatcgc | 1020 |
| aaagcggaag gcattattcc cgtgcactcc gttcgcgaca atatcaacat cagtgccaga | 1080 |
| cgtaaacatg tgctcggcgg ttgtgtaatc aacaacggtt gggaagaaaa caatgccgat | 1140 |
| caccacattc gttcgctcaa catcaaaacg ccgggcgcgg agcaactgat catgaatctc | 1200 |
| tcaggcggaa atcagcaaaa agccattctg gccgctggt tatcggaaga gatgaaggtc | 1260 |
| attttgctgg atgaacctac gcgcggcatt gatgttggcg ctaagcacga aatatataac | 1320 |
| gtaatttatg cgctggcggc gcagggcgtg gcggtgctgt ttgcctccag cgacttacct | 1380 |
| gaagtcctcg gcgttgccga ccggattgtg gtgatgcggg aaggtgaaat cgccggtgaa | 1440 |
| ttgttacacg agcaggcaga tgagcgtcag gcactgagcc ttgcgatgcc taaagtcagc | 1500 |
| caggctgttg cctga | 1515 |

<210> SEQ ID NO 22
<211> LENGTH: 987
<212> TYPE: DNA
<213> ORGANISM: Escherichia coli

<400> SEQUENCE: 22

|  |  |
|---|---|
| atgtcttctg tttctacatc ggggtctggc gcacctaagt cgtcattcag cttcgggcgt | 60 |
| atctgggatc agtacggcat gctggtggtg tttgcggtgc tctttatcgc ctgtgccatt | 120 |
| tttgtcccaa attttgccac cttcattaat atgaaagggt tgggcctggc aatttccatg | 180 |
| tcggggatgg tggcttgtgg catgttgttc tgcctcgctt ccggtgactt tgaccttct | 240 |
| gtcgcctccg taattgcctg tgcggtgtc accacggcgg tggttattaa cctgactgaa | 300 |
| agcctgtgga ttggcgtggc agcggggttg ttgctgggcg ttctctgtgg cctggtcaat | 360 |
| ggctttgtta tcgccaaact gaaaataaat gctctgatca cgacattggc aacgatgcag | 420 |
| attgttcgag gtctggcgta catcatttca gacggtaaag cggtcggtat cgaagatgaa | 480 |
| agcttctttg cccttggtta cgccaactgg ttcggtctgc ctgcgccaat ctggctcacc | 540 |
| gtcgcgtgtc tgattatctt tggtttgctg ctgaataaaa ccacctttgg tcgtaacacc | 600 |
| ctggcgattg gcgggaacga agaggccgcg cgtctggcgg tgtaccggt tgttcgcacc | 660 |
| aaaattatta tctttgttct ctcaggcctg gtatcagcga tagccggaat tatttctggct | 720 |
| tcacgtatga ccagtgggca gccaatgacg tcgattggtt atgagctgat tgttatctcc | 780 |
| gcctgcgttt aggtggcgt ttctctgaaa ggtggcatcg gaaaaatctc atatgtggtg | 840 |
| gcgggtatct taattttagg caccgtggaa aacgccatga acctgcttaa tatttctcct | 900 |
| ttcgcgcagt acgtggttcg cggcttaatc ctgctggcag cggtgatctt cgaccgttac | 960 |
| aagcaaaaag cgaaacgcac tgtctga | 987 |

<210> SEQ ID NO 23
<211> LENGTH: 329
<212> TYPE: PRT
<213> ORGANISM: Escherichia coli

<400> SEQUENCE: 23

Met His Lys Phe Thr Lys Ala Leu Ala Ala Ile Gly Leu Ala Ala Val
1               5                   10                  15

Met Ser Gln Ser Ala Met Ala Glu Asn Leu Lys Leu Gly Phe Leu Val
                20                  25                  30

Lys Gln Pro Glu Glu Pro Trp Phe Gln Thr Glu Trp Lys Phe Ala Asp
            35                  40                  45

Lys Ala Gly Lys Asp Leu Gly Phe Glu Val Ile Lys Ile Ala Val Pro
        50                  55                  60

Asp Gly Glu Lys Thr Leu Asn Ala Ile Asp Ser Leu Ala Ala Ser Gly
65                  70                  75                  80

Ala Lys Gly Phe Val Ile Cys Thr Pro Asp Pro Lys Leu Gly Ser Ala
                85                  90                  95

Ile Val Ala Lys Ala Arg Gly Tyr Asp Met Lys Val Ile Ala Val Asp
            100                 105                 110

Asp Gln Phe Val Asn Ala Lys Gly Lys Pro Met Asp Thr Val Pro Leu
        115                 120                 125

Val Met Met Ala Ala Thr Lys Ile Gly Glu Arg Gln Gly Gln Glu Leu
130                 135                 140

Tyr Lys Glu Met Gln Lys Arg Gly Trp Asp Val Lys Glu Ser Ala Val
145                 150                 155                 160

Met Ala Ile Thr Ala Asn Glu Leu Asp Thr Ala Arg Arg Arg Thr Thr
                165                 170                 175

Gly Ser Met Asp Ala Leu Lys Ala Ala Gly Phe Pro Glu Lys Gln Ile
            180                 185                 190

Tyr Gln Val Pro Thr Lys Ser Asn Asp Ile Pro Gly Ala Phe Asp Ala
        195                 200                 205

Ala Asn Ser Met Leu Val Gln His Pro Glu Val Lys His Trp Leu Ile
210                 215                 220

Val Gly Met Asn Asp Ser Thr Val Leu Gly Gly Val Arg Ala Thr Glu
225                 230                 235                 240

Gly Gln Gly Phe Lys Ala Ala Asp Ile Ile Gly Ile Gly Ile Asn Gly
                245                 250                 255

Val Asp Ala Val Ser Glu Leu Ser Lys Ala Gln Ala Thr Gly Phe Tyr
            260                 265                 270

Gly Ser Leu Leu Pro Ser Pro Asp Val His Gly Tyr Lys Ser Ser Glu
        275                 280                 285

Met Leu Tyr Asn Trp Val Ala Lys Asp Val Glu Pro Pro Lys Phe Thr
290                 295                 300

Glu Val Thr Asp Val Val Leu Ile Thr Arg Asp Asn Phe Lys Glu Glu
305                 310                 315                 320

Leu Glu Lys Lys Gly Leu Gly Gly Lys
                325

<210> SEQ ID NO 24
<211> LENGTH: 504
<212> TYPE: PRT
<213> ORGANISM: Escherichia coli

<400> SEQUENCE: 24

Met Gln Gln Ser Thr Pro Tyr Leu Ser Phe Arg Gly Ile Gly Lys Thr

-continued

```
  1               5                   10                  15
Phe Pro Gly Val Lys Ala Leu Thr Asp Ile Ser Phe Asp Cys Tyr Ala
             20                  25                  30
Gly Gln Val His Ala Leu Met Gly Glu Asn Gly Ala Gly Lys Ser Thr
             35                  40                  45
Leu Leu Lys Ile Leu Ser Gly Asn Tyr Ala Pro Thr Thr Gly Ser Val
 50                  55                  60
Val Ile Asn Gly Gln Glu Met Ser Phe Ser Asp Thr Thr Ala Ala Leu
 65                  70                  75                  80
Asn Ala Gly Val Ala Ile Ile Tyr Gln Glu Leu His Leu Val Pro Glu
                 85                  90                  95
Met Thr Val Ala Glu Asn Ile Tyr Leu Gly Gln Leu Pro His Lys Gly
                100                 105                 110
Gly Ile Val Asn Arg Ser Leu Leu Asn Tyr Glu Ala Gly Leu Gln Leu
                115                 120                 125
Lys His Leu Gly Met Asp Ile Asp Pro Asp Thr Pro Leu Lys Tyr Leu
130                 135                 140
Ser Ile Gly Gln Trp Gln Met Val Glu Ile Ala Lys Ala Leu Ala Arg
145                 150                 155                 160
Asn Ala Lys Ile Ile Ala Phe Asp Glu Pro Thr Ser Ser Leu Ser Ala
                165                 170                 175
Arg Glu Ile Asp Asn Leu Phe Arg Val Ile Arg Glu Leu Arg Lys Glu
                180                 185                 190
Gly Arg Val Ile Leu Tyr Val Ser His Arg Met Glu Glu Ile Phe Ala
            195                 200                 205
Leu Ser Asp Ala Ile Thr Val Phe Lys Asp Gly Arg Tyr Val Lys Thr
210                 215                 220
Phe Thr Asp Met Gln Gln Val Asp His Asp Ala Leu Val Gln Ala Met
225                 230                 235                 240
Val Gly Arg Asp Ile Gly Asp Ile Tyr Gly Trp Gln Pro Arg Ser Tyr
                245                 250                 255
Gly Glu Glu Arg Leu Arg Leu Asp Ala Val Lys Ala Pro Gly Val Arg
            260                 265                 270
Thr Pro Ile Ser Leu Ala Val Arg Ser Gly Glu Ile Val Gly Leu Phe
            275                 280                 285
Gly Leu Val Gly Ala Gly Arg Ser Glu Leu Met Lys Gly Met Phe Gly
            290                 295                 300
Gly Thr Gln Ile Thr Ala Gly Gln Val Tyr Ile Asp Gln Gln Pro Ile
305                 310                 315                 320
Asp Ile Arg Lys Pro Ser His Ala Ile Ala Ala Gly Met Met Leu Cys
                325                 330                 335
Pro Glu Asp Arg Lys Ala Glu Gly Ile Ile Pro Val His Ser Val Arg
                340                 345                 350
Asp Asn Ile Asn Ile Ser Ala Arg Arg Lys His Val Leu Gly Gly Cys
            355                 360                 365
Val Ile Asn Asn Gly Trp Glu Glu Asn Ala Asp His His Ile Arg
            370                 375                 380
Ser Leu Asn Ile Lys Thr Pro Gly Ala Glu Gln Leu Ile Met Asn Leu
385                 390                 395                 400
Ser Gly Gly Asn Gln Gln Lys Ala Ile Leu Gly Arg Trp Leu Ser Glu
                405                 410                 415
Glu Met Lys Val Ile Leu Leu Asp Glu Pro Thr Arg Gly Ile Asp Val
            420                 425                 430
```

Gly Ala Lys His Glu Ile Tyr Asn Val Ile Tyr Ala Leu Ala Ala Gln
            435                 440                 445

Gly Val Ala Val Leu Phe Ala Ser Ser Asp Leu Pro Glu Val Leu Gly
    450                 455                 460

Val Ala Asp Arg Ile Val Val Met Arg Glu Gly Glu Ile Ala Gly Glu
465                 470                 475                 480

Leu Leu His Glu Gln Ala Asp Glu Arg Gln Ala Leu Ser Leu Ala Met
                485                 490                 495

Pro Lys Val Ser Gln Ala Val Ala
            500

<210> SEQ ID NO 25
<211> LENGTH: 328
<212> TYPE: PRT
<213> ORGANISM: Escherichia coli

<400> SEQUENCE: 25

Met Ser Ser Val Ser Thr Ser Gly Ser Gly Ala Pro Lys Ser Ser Phe
1               5                   10                  15

Ser Phe Gly Arg Ile Trp Asp Gln Tyr Gly Met Leu Val Val Phe Ala
            20                  25                  30

Val Leu Phe Ile Ala Cys Ala Ile Phe Val Pro Asn Phe Ala Thr Phe
        35                  40                  45

Ile Asn Met Lys Gly Leu Gly Leu Ala Ile Ser Met Ser Gly Met Val
    50                  55                  60

Ala Cys Gly Met Leu Phe Cys Leu Ala Ser Gly Asp Phe Asp Leu Ser
65                  70                  75                  80

Val Ala Ser Val Ile Ala Cys Ala Gly Val Thr Thr Ala Val Val Ile
                85                  90                  95

Asn Leu Thr Glu Ser Leu Trp Ile Gly Val Ala Ala Gly Leu Leu Leu
            100                 105                 110

Gly Val Leu Cys Gly Leu Val Asn Gly Phe Val Ile Ala Lys Leu Lys
        115                 120                 125

Ile Asn Ala Leu Ile Thr Thr Leu Ala Thr Met Gln Ile Val Arg Gly
    130                 135                 140

Leu Ala Tyr Ile Ile Ser Asp Gly Lys Ala Val Gly Ile Glu Asp Glu
145                 150                 155                 160

Ser Phe Phe Ala Leu Gly Tyr Ala Asn Trp Phe Gly Leu Pro Ala Pro
                165                 170                 175

Ile Trp Leu Thr Val Ala Cys Leu Ile Ile Phe Gly Leu Leu Leu Asn
            180                 185                 190

Lys Thr Thr Phe Gly Arg Asn Thr Leu Ala Ile Gly Gly Asn Glu Glu
        195                 200                 205

Ala Ala Arg Leu Ala Gly Val Pro Val Val Arg Thr Lys Ile Ile Ile
    210                 215                 220

Phe Val Leu Ser Gly Leu Val Ser Ala Ile Ala Gly Ile Ile Leu Ala
225                 230                 235                 240

Ser Arg Met Thr Ser Gly Gln Pro Met Thr Ser Ile Gly Tyr Glu Leu
                245                 250                 255

Ile Val Ile Ser Ala Cys Val Leu Gly Gly Val Ser Leu Lys Gly Gly
            260                 265                 270

Ile Gly Lys Ile Ser Tyr Val Val Ala Gly Ile Leu Ile Leu Gly Thr
        275                 280                 285

Val Glu Asn Ala Met Asn Leu Leu Asn Ile Ser Pro Phe Ala Gln Tyr

```
                290               295               300
Val Val Arg Gly Leu Ile Leu Leu Ala Ala Val Ile Phe Asp Arg Tyr
305                 310               315               320

Lys Gln Lys Ala Lys Arg Thr Val
                325

<210> SEQ ID NO 26
<211> LENGTH: 993
<212> TYPE: DNA
<213> ORGANISM: Escherichia coli

<400> SEQUENCE: 26
atgaaaataa agaacattct actcacccctt tgcacctcac tcctgcttac caacgttgct    60
gcacacgcca agaagtcaa ataggtatg gcgattgatg atctccgtct tgaacgctgg      120
caaaaagatc gagatatctt tgtgaaaaag gcagaatctc tcggcgcgaa agtatttgta   180
cagtctgcaa atggcaatga agaaacacaa atgtcgcaga ttgaaaacat gataaaccgg   240
ggtgtcgatg ttcttgtcat tattccgtat aacggtcagg tattaagtaa cgttgtaaaa   300
gaagccaaac aagaaggcat taaagtatta gcttacgacc gtatgattaa cgatgcggat   360 atcgatttt atatttcttt cgataacgaa aaagtcggtg aactgcaggc aaaagccctg    420
gtcgatattg ttccgcaagg taattacttc ctgatgggcg gctcgccggt agataacaac   480
gccaagctgt tccgcgccgg acaaatgaaa gtgttaaaac cttacgttga ttccggaaaa   540
attaaagtcg ttggtgacca atgggttgat ggctggttac cggaaaacgc attgaaaatt   600
atggaaaacg cgctaaccgc caataataac aaaattgatg ctgtagttgc ctcaaacgat   660
gccaccgcag gtggggcaat tcaggcatta agcgcgcaag gtttatcagg aaagtagca   720 atctccggcc aggatgcgga tctcgcaggt attaaacgta ttgctgccgg tacgcaaact   780
atgacggtgt ataaacctat tacgttgttg gcaaatactg ccgcagaaat tgccgttgag   840
ttgggcaatg gtcaggaacc aaaagcagat accacactga ataatggcct gaaagatgtc   900
ccctcccgcc tcctgacacc gatcgatgtg aataaaaaca acatcaaaga tacggtaatt   960
aaagacggat tccacaaaga gagcgagctg taa                                993

<210> SEQ ID NO 27
<211> LENGTH: 1542
<212> TYPE: DNA
<213> ORGANISM: Escherichia coli

<400> SEQUENCE: 27
atgccttatc tacttgaaat gaagaacatt accaaaacct tcggcagtgt gaaggcgatt    60
gataacgtct gcttgcggtt gaatgctggc gaaatcgtct cactttgtgg ggaaaatggg   120
tctggtaaat caacgctgat gaaagtgctg tgtggtattt atcccatgg ctcctacgaa    180 ggcgaaatta ttttgcggg agaagagatt caggcgagtc acatccgcga taccgaacgc   240
aaaggtatcg ccatcattca tcaggaattg gccctggtga agaattgac cgtgctggaa   300 aatatcttcc tgggtaacga ataaccccac aatggcatta tggattatga cctgatgacg   360
ctacgctgtc agaagctgct cgcacaggtc agtttatcca tttcacctga tacccgcgtt   420
ggcgatttag ggcttgggca acaacaactg gttgaaattg ccaaggcact taataaacag   480
gtgcgcttgt taattctcga tgaaccgaca gcctcattaa ctgagcagga aacgtcgatt   540
ttactggata ttattcgcga tctacaacag cacggtatcg cctgtattta tatttcgcac   600
aaactcaacg aagtcaaagc gatttccgat acgatttgcg ttattcgcga cggacagcac   660
```

```
attggtacgc gtgatgctgc cggaatgagt gaagacgata ttatcaccat gatggtcggg    720
cgagagttaa ccgcgcttta ccctaatgaa ccacatacca ccggagatga aatattacgt    780
attgaacatc tgacggcatg gcatccggtt aatcgtcata ttaaacgagt taatgatgtc    840
tcgttttccc tgaaacgtgg cgaaatattg ggtattgccg gactcgttgg tgccggacgt    900
accgagacca ttcagtgcct gtttggtgtg tggcccggac aatgggaagg aaaaatttat    960
attgatggca aacaggtaga tattcgtaac tgtcagcaag ccatcgccca ggggattgcg   1020
atggtccccg aagacagaaa gcgcgacggc atcgttccgg taatggcggt tggtaaaaat   1080
attaccctcg ccgcactcaa taaatttacc ggtggcatta gccagcttga tgacgcggca   1140
gagcaaaaat gtattctgga atcaatccag caactcaaag ttaaaacgtc gtcccccgac   1200
cttgctattg gacgtttgag cggcggcaat cagcaaaaag cgatcctcgc tcgctgtctg   1260
ttacttaacc cgcgcattct cattcttgat gaacccacca ggggtatcga tattggcgcg   1320
aaatacgaga tctacaaatt aattaaccaa ctcgtccagc agggtattgc cgttattgtc   1380
atctcttccg aattacctga agtgctcggc cttagcgatc gtgtactggt gatgcatgaa   1440
gggaaactaa aagccaacct gataaatcat aacctgactc aggagcaggt gatggaagcc   1500
gcattgagga gcgaacatca tgtcgaaaag caatccgtct ga                      1542
```

<210> SEQ ID NO 28
<211> LENGTH: 1182
<212> TYPE: DNA
<213> ORGANISM: Escherichia coli

<400> SEQUENCE: 28

```
atgtcgaaaa gcaatccgtc tgaagtgaaa ttggccgtac cgacatccgg tggcttctcc     60
gggctgaaat cactgaattt gcaggtcttc gtgatgattg cagctatcat cgcaatcatg    120 ctgttctttta cctggaccac cgatggtgcc tacttaagcg cccgtaacgt ctccaacctg    180
ttacgccaga ccgcgattac cggcatcctc gcggtaggaa tggtgttcgt cataatttct    240
gctgaaatcg acctttccgt cggctcaatg atggggctgt taggtggcgt cgcggcgatt    300
tgtgacgtct ggttaggctg gccttttgcca cttaccatca ttgtgacgct ggttctggga    360
ctgcttctcg gtgcctggaa cggatggtgg gtcgcgtacc gtaaagtccc ttcatttatt    420
gtcaccctcg cgggcatgtt ggcatttcgc ggcatactca ttggcatcac caacggcacg    480
actgtatccc ccaccagcgc cgcgatgtca caaattgggc aaagctatct ccccgccagt    540
accggcttca tcattggcgc gcttggctta atggcttttg ttggttggca atggcgcgga    600
agaatgcgcc gtcaggcttt gggtttacag tctccggcct ctaccgcagt agtcggtcgc    660
caggctttaa ccgctatcat cgtattaggc gcaatctggc tgttgaatga ttaccgtggc    720
gttcccactc ctgttctgct gctgacgttg ctgttactcg gcggaatgtt tatggcaacg    780
cggacggcat ttgacgacg catttatgcc atcggcggca atctgaagc agcacgtctc    840 tccgggatta acgttgaacg caccaaactt gccgtgttcg cgattaacgg attaatggta    900
gccatcgccg gattaatcct tagttctcga cttggcgctg gttcaccttc tgcgggaaat    960
atcgccgaac tggacgcaat tgcagcatgc gtgattggcg gcaccagcct ggctggcggt   1020
gtgggaagcg ttgccggagc agtaatgggg gcatttatca tggcttcact ggataacggc   1080
atgagtatga tggatgtacc gaccttctgg cagtatatcg ttaaaggtgc gattctgttg   1140
ctggcagtat ggatggactc cgcaaccaaa cgccgttctt ga                      1182
```

```
<210> SEQ ID NO 29
<211> LENGTH: 330
<212> TYPE: PRT
<213> ORGANISM: Escherichia coli

<400> SEQUENCE: 29

Met Lys Ile Lys Asn Ile Leu Leu Thr Leu Cys Thr Ser Leu Leu Leu
1               5                   10                  15

Thr Asn Val Ala Ala His Ala Lys Glu Val Lys Ile Gly Met Ala Ile
            20                  25                  30

Asp Asp Leu Arg Leu Glu Arg Trp Gln Lys Asp Arg Asp Ile Phe Val
        35                  40                  45

Lys Lys Ala Glu Ser Leu Gly Ala Lys Val Phe Val Gln Ser Ala Asn
    50                  55                  60

Gly Asn Glu Glu Thr Gln Met Ser Gln Ile Glu Asn Met Ile Asn Arg
65                  70                  75                  80

Gly Val Asp Val Leu Val Ile Ile Pro Tyr Asn Gly Gln Val Leu Ser
                85                  90                  95

Asn Val Val Lys Glu Ala Lys Gln Glu Gly Ile Lys Val Leu Ala Tyr
            100                 105                 110

Asp Arg Met Ile Asn Asp Ala Asp Ile Asp Phe Tyr Ile Ser Phe Asp
        115                 120                 125

Asn Glu Lys Val Gly Glu Leu Gln Ala Lys Ala Leu Val Asp Ile Val
    130                 135                 140

Pro Gln Gly Asn Tyr Phe Leu Met Gly Gly Ser Pro Val Asp Asn Asn
145                 150                 155                 160

Ala Lys Leu Phe Arg Ala Gly Gln Met Lys Val Leu Lys Pro Tyr Val
                165                 170                 175

Asp Ser Gly Lys Ile Lys Val Val Gly Asp Gln Trp Val Asp Gly Trp
            180                 185                 190

Leu Pro Glu Asn Ala Leu Lys Ile Met Glu Asn Ala Leu Thr Ala Asn
        195                 200                 205

Asn Asn Lys Ile Asp Ala Val Val Ala Ser Asn Asp Ala Thr Ala Gly
    210                 215                 220

Gly Ala Ile Gln Ala Leu Ser Ala Gln Gly Leu Ser Gly Lys Val Ala
225                 230                 235                 240

Ile Ser Gly Gln Asp Ala Asp Leu Ala Gly Ile Lys Arg Ile Ala Ala
                245                 250                 255

Gly Thr Gln Thr Met Thr Val Tyr Lys Pro Ile Thr Leu Leu Ala Asn
            260                 265                 270

Thr Ala Ala Glu Ile Ala Val Glu Leu Gly Asn Gly Gln Glu Pro Lys
        275                 280                 285

Ala Asp Thr Thr Leu Asn Asn Gly Leu Lys Asp Val Pro Ser Arg Leu
    290                 295                 300

Leu Thr Pro Ile Asp Val Asn Lys Asn Ile Lys Asp Thr Val Ile
305                 310                 315                 320

Lys Asp Gly Phe His Lys Glu Ser Glu Leu
                325                 330

<210> SEQ ID NO 30
<211> LENGTH: 513
<212> TYPE: PRT
<213> ORGANISM: Escherichia coli

<400> SEQUENCE: 30
```

```
Met Pro Tyr Leu Leu Glu Met Lys Asn Ile Thr Lys Thr Phe Gly Ser
1               5                   10                  15

Val Lys Ala Ile Asp Asn Val Cys Leu Arg Leu Asn Ala Gly Glu Ile
            20                  25                  30

Val Ser Leu Cys Gly Glu Asn Gly Ser Gly Lys Ser Thr Leu Met Lys
        35                  40                  45

Val Leu Cys Gly Ile Tyr Pro His Gly Ser Tyr Glu Gly Glu Ile Ile
    50                  55                  60

Phe Ala Gly Glu Glu Ile Gln Ala Ser His Ile Arg Asp Thr Glu Arg
65                  70                  75                  80

Lys Gly Ile Ala Ile Ile His Gln Glu Leu Ala Leu Val Lys Glu Leu
                85                  90                  95

Thr Val Leu Glu Asn Ile Phe Leu Gly Asn Glu Ile Thr His Asn Gly
            100                 105                 110

Ile Met Asp Tyr Asp Leu Met Thr Leu Arg Cys Gln Lys Leu Leu Ala
            115                 120                 125

Gln Val Ser Leu Ser Ile Ser Pro Asp Thr Arg Val Gly Asp Leu Gly
        130                 135                 140

Leu Gly Gln Gln Gln Leu Val Glu Ile Ala Lys Ala Leu Asn Lys Gln
145                 150                 155                 160

Val Arg Leu Leu Ile Leu Asp Glu Pro Thr Ala Ser Leu Thr Glu Gln
                165                 170                 175

Glu Thr Ser Ile Leu Leu Asp Ile Ile Arg Asp Leu Gln Gln His Gly
            180                 185                 190

Ile Ala Cys Ile Tyr Ile Ser His Lys Leu Asn Glu Val Lys Ala Ile
            195                 200                 205

Ser Asp Thr Ile Cys Val Ile Arg Asp Gly Gln His Ile Gly Thr Arg
210                 215                 220

Asp Ala Ala Gly Met Ser Glu Asp Ile Ile Thr Met Met Val Gly
225                 230                 235                 240

Arg Glu Leu Thr Ala Leu Tyr Pro Asn Glu Pro His Thr Thr Gly Asp
                245                 250                 255

Glu Ile Leu Arg Ile Glu His Leu Thr Ala Trp His Pro Val Asn Arg
            260                 265                 270

His Ile Lys Arg Val Asn Asp Val Ser Phe Ser Leu Lys Arg Gly Glu
        275                 280                 285

Ile Leu Gly Ile Ala Gly Leu Val Gly Ala Gly Arg Thr Glu Thr Ile
    290                 295                 300

Gln Cys Leu Phe Gly Val Trp Pro Gly Gln Trp Glu Gly Lys Ile Tyr
305                 310                 315                 320

Ile Asp Gly Lys Gln Val Asp Ile Arg Asn Cys Gln Gln Ala Ile Ala
                325                 330                 335

Gln Gly Ile Ala Met Val Pro Glu Asp Arg Lys Arg Asp Gly Ile Val
            340                 345                 350

Pro Val Met Ala Val Gly Lys Asn Ile Thr Leu Ala Ala Leu Asn Lys
        355                 360                 365

Phe Thr Gly Gly Ile Ser Gln Leu Asp Asp Ala Ala Glu Gln Lys Cys
    370                 375                 380

Ile Leu Glu Ser Ile Gln Leu Lys Val Lys Thr Ser Ser Pro Asp
385                 390                 395                 400

Leu Ala Ile Gly Arg Leu Ser Gly Gly Asn Gln Gln Lys Ala Ile Leu
                405                 410                 415

Ala Arg Cys Leu Leu Leu Asn Pro Arg Ile Leu Ile Leu Asp Glu Pro
```

```
                420                 425                 430
Thr Arg Gly Ile Asp Ile Gly Ala Lys Tyr Glu Ile Tyr Lys Leu Ile
            435                 440                 445

Asn Gln Leu Val Gln Gln Gly Ile Ala Val Ile Val Ile Ser Ser Glu
        450                 455                 460

Leu Pro Glu Val Leu Gly Leu Ser Asp Arg Val Leu Val Met His Glu
465                 470                 475                 480

Gly Lys Leu Lys Ala Asn Leu Ile Asn His Asn Leu Thr Gln Glu Gln
                485                 490                 495

Val Met Glu Ala Ala Leu Arg Ser Glu His His Val Glu Lys Gln Ser
            500                 505                 510

Val

<210> SEQ ID NO 31
<211> LENGTH: 330
<212> TYPE: PRT
<213> ORGANISM: Escherichia coli

<400> SEQUENCE: 31

Met Lys Ile Lys Asn Ile Leu Leu Thr Leu Cys Thr Ser Leu Leu Leu
1               5                   10                  15

Thr Asn Val Ala Ala His Ala Lys Glu Val Lys Ile Gly Met Ala Ile
            20                  25                  30

Asp Asp Leu Arg Leu Glu Arg Trp Gln Lys Asp Arg Asp Ile Phe Val
        35                  40                  45

Lys Lys Ala Glu Ser Leu Gly Ala Lys Val Phe Val Gln Ser Ala Asn
    50                  55                  60

Gly Asn Glu Glu Thr Gln Met Ser Gln Ile Glu Asn Met Ile Asn Arg
65                  70                  75                  80

Gly Val Asp Val Leu Val Ile Ile Pro Tyr Asn Gly Gln Val Leu Ser
                85                  90                  95

Asn Val Val Lys Glu Ala Lys Gln Glu Gly Ile Lys Val Leu Ala Tyr
            100                 105                 110

Asp Arg Met Ile Asn Asp Ala Asp Ile Asp Phe Tyr Ile Ser Phe Asp
        115                 120                 125

Asn Glu Lys Val Gly Glu Leu Gln Ala Lys Ala Leu Val Asp Ile Val
    130                 135                 140

Pro Gln Gly Asn Tyr Phe Leu Met Gly Gly Ser Pro Val Asp Asn Asn
145                 150                 155                 160

Ala Lys Leu Phe Arg Ala Gly Gln Met Lys Val Leu Lys Pro Tyr Val
                165                 170                 175

Asp Ser Gly Lys Ile Lys Val Val Gly Asp Gln Trp Val Asp Gly Trp
            180                 185                 190

Leu Pro Glu Asn Ala Leu Lys Ile Met Glu Asn Ala Leu Thr Ala Asn
        195                 200                 205

Asn Asn Lys Ile Asp Ala Val Val Ala Ser Asn Asp Ala Thr Ala Gly
    210                 215                 220

Gly Ala Ile Gln Ala Leu Ser Ala Gln Gly Leu Ser Gly Lys Val Ala
225                 230                 235                 240

Ile Ser Gly Gln Asp Ala Asp Leu Ala Gly Ile Lys Arg Ile Ala Ala
                245                 250                 255

Gly Thr Gln Thr Met Thr Val Tyr Lys Pro Ile Thr Leu Leu Ala Asn
            260                 265                 270

Thr Ala Ala Glu Ile Ala Val Glu Leu Gly Asn Gly Gln Glu Pro Lys
```

Ala Asp Thr Thr Leu Asn Asn Gly Leu Lys Asp Val Pro Ser Arg Leu
    275                 280                 285

Leu Thr Pro Ile Asp Val Asn Lys Asn Asn Ile Lys Asp Thr Val Ile
290                 295                 300

Lys Asp Gly Phe His Lys Glu Ser Glu Leu
305                 310                 315                 320

325                 330

<210> SEQ ID NO 32
<211> LENGTH: 879
<212> TYPE: DNA
<213> ORGANISM: Escherichia coli

<400> SEQUENCE: 32
atggctgaag cgcaaaatga tcccctgctg ccgggatact cgtttaacgc ccatctggtg      60
gcgggtttaa cgccgattga ggccaacggt tatctcgatt tttttatcga ccgaccgctg     120
ggaatgaaag gttatattct caatctcacc attcgcggtc aggggtggt gaaaaatcag     180
ggacgagaat ttgtctgccg accgggtgat attttgctgt tcccgccagg agagattcat     240
cactacggtc gtcatccgga ggctcgcgaa tggtatcacc agtgggttta ctttcgtccg     300
cgcgcctact ggcatgaatg gcttaactgg ccgtcaatat ttgccaatac gggtttcttt     360
cgcccgatg aagcgcacca gccgcatttc agcgacctgt ttgggcaaat cattaacgcc     420
gggcaagggg aagggcgcta tcggagctg ctggcgataa atctgcttga gcaattgtta     480
ctgcggcgca tggaagcgat taacgagtcg ctccatccac cgatggataa tcgggtacgc     540
gaggcttgtc agtacatcag cgatcacctg gcagacagca ttttgatat cgccagcgtc     600
gcacagcatg tttgcttgtc gccgtcgcgt ctgtcacatc ttttccgcca gcagttaggg     660
attagcgtct taagctggcg cgaggaccaa cgcattagtc aggcgaagct gcttttgagc     720
actacccgga tgcctatcgc caccgtcggt cgcaatgttg gttttgacga tcaactctat     780
ttctcgcgag tatttaaaaa atgcaccggg gccagcccga gcgagtttcg tgccggttgt     840
gaagaaaaag tgaatgatgt agccgtcaag ttgtcataa                            879

<210> SEQ ID NO 33
<211> LENGTH: 292
<212> TYPE: PRT
<213> ORGANISM: Escherichia coli

<400> SEQUENCE: 33

Met Ala Glu Ala Gln Asn Asp Pro Leu Leu Pro Gly Tyr Ser Phe Asn
1               5                   10                  15

Ala His Leu Val Ala Gly Leu Thr Pro Ile Glu Ala Asn Gly Tyr Leu
                20                  25                  30

Asp Phe Phe Ile Asp Arg Pro Leu Gly Met Lys Gly Tyr Ile Leu Asn
            35                  40                  45

Leu Thr Ile Arg Gly Gln Gly Val Val Lys Asn Gln Gly Arg Glu Phe
        50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro

|  | 115 |  |  |  | 120 |  |  |  | 125 |  |  |
|---|---|---|---|---|---|---|---|---|---|---|---|

His Phe Ser Asp Leu Phe Gly Gln Ile Ile Asn Ala Gly Gln Gly Glu
            130                    135                140

Gly Arg Tyr Ser Glu Leu Leu Ala Ile Asn Leu Leu Glu Gln Leu Leu
145                    150                  155                160

Leu Arg Arg Met Glu Ala Ile Asn Glu Ser Leu His Pro Pro Met Asp
                  165                  170                175

Asn Arg Val Arg Glu Ala Cys Gln Tyr Ile Ser Asp His Leu Ala Asp
            180                  185                190

Ser Asn Phe Asp Ile Ala Ser Val Ala Gln His Val Cys Leu Ser Pro
                195                  200              205

Ser Arg Leu Ser His Leu Phe Arg Gln Gln Leu Gly Ile Ser Val Leu
210                    215                  220

Ser Trp Arg Glu Asp Gln Arg Ile Ser Gln Ala Lys Leu Leu Leu Ser
225                    230                  235                240

Thr Thr Arg Met Pro Ile Ala Thr Val Gly Arg Asn Val Gly Phe Asp
            245                  250                255

Asp Gln Leu Tyr Phe Ser Arg Val Phe Lys Lys Cys Thr Gly Ala Ser
                260                  265              270

Pro Ser Glu Phe Arg Ala Gly Cys Glu Glu Lys Val Asn Asp Val Ala
            275                  280                285

Val Lys Leu Ser
      290

<210> SEQ ID NO 34
<211> LENGTH: 1506
<212> TYPE: DNA
<213> ORGANISM: Escherichia coli

<400> SEQUENCE: 34

| | | | | | |
|---|---|---|---|---|---|
| atggaagcat | tacttcagct | taaaggcatc | gataaagcct | tcccgggcgt | aaaagccctc | 60 |
| tcgggcgcag | cgttaaatgt | ctatccgggc | gcgtgatggg | cgctggtggg | cgaaaacggc | 120 |
| gcgggtaaat | ccaccatgat | gaaagtgctt | actggcatct | atactcgcga | tgccggtacg | 180 |
| cttttatggc | tggggaaaga | aacgacattt | accgggccaa | atcttccca | ggaagccggg | 240 |
| attgggatta | tccatcagga | actgaacctg | atcccgcagt | tgaccattgc | gaaaacatt | 300 |
| ttcctcggtc | gtgagtttgt | taatcgcttt | ggcaaaattg | actggaaaac | catgtatgcc | 360 |
| gaagcggata | aattgctggc | taaacttaac | ctgcgcttta | aaagcgacaa | gctggtgggc | 420 |
| gatctttcca | tcggtgacca | gcaaatggtt | gaaatcgcca | aagtgctgag | ctttgagtcg | 480 |
| aaagtcatca | ttatggatga | accgaccgat | gcgctgaccg | ataccgaaac | cgaatccctg | 540 |
| ttccgcgtca | tccgcgagct | gaaatcgcaa | ggccgcggta | ttgtctatat | ctcccaccgc | 600 |
| atgaaagaaa | tcttcgagat | ttgcgatgac | gttaccgttt | ttcgtgatgg | gcaatttatt | 660 |
| gctgagcgcg | aagtggcatc | actgaccgaa | gattcgctga | ttgagatgat | ggtgggtcgc | 720 |
| aagctggaag | atcaatatcc | gcacctggac | aaagcgccgg | gagatatccg | cctgaaagtc | 780 |
| gataatctct | gcggacctgg | cgttaacgat | gtctctttta | ctttacgcaa | aggcgaaatt | 840 |
| cttggcgtct | ctggtttgat | gggcgcaggt | cgtaccgaac | tgatgaaagt | gctctacggc | 900 |
| gcactaccgc | gcaccagcgg | ttacgtcacc | ctggatgggc | atgaagtcgt | taccgttca | 960 |
| ccgcaggatg | cctggcaaa | cggcattgtg | tatatctccg | aagaccgtaa | acgtgacggt | 1020 |
| ttagtgttgg | gcatgtcagt | aaaagagaac | atgtcgctga | cagcgctgcg | ctacttcagc | 1080 |

```
cgcgctggcg gcagtttgaa gcatgccgat gaacagcagg ctgtgagtga tttcattcgt    1140
ctgtttaatg tgaaaactcc gtcgatggaa caggcaattg gtctgctttc cggtggcaat    1200
cagcaaaaag tggcgattgc cgcggtctg atgacacgcc ccaaagtgtt gatccttgat     1260
gaacctaccc gtggcgtaga tgtcggcgcg aaaaaagaga tctatcaact gattaaccag    1320
ttcaaagccg atggcttgag catcattctg gtgtcatcgg agatgccaga agtattaggc    1380
atgagcgatc gcatcatcgt catgcatgaa gggcatctca gcggggaatt tactcgtgag    1440
caggccaccc aggaagtgtt aatggctgcc gctgtgggca agcttaatcg cgtgaatcag    1500
gagtaa                                                               1506

<210> SEQ ID NO 35
<211> LENGTH: 891
<212> TYPE: DNA
<213> ORGANISM: Escherichia coli

<400> SEQUENCE: 35
atgaacatga aaaaactggc taccctggtt ccgctgttg cgctaagcgc caccgtcagt      60
gcgaatgcga tggcaaaaga caccatcgcg ctggtggtct ccacgcttaa caacccgttc    120
tttgtatcgc tgaaagatgg cgcgcagaaa gaggcggata acttggcta taacctggtg     180 gtgctggact cccagaacaa cccggcgaaa gagctggcga acgtgcagga cttaaccgtt    240
cgcggcacaa aaattctgct gattaacccg accgactccg acgcagtggg taatgctgtg    300
aagatggcta accaggcgaa catcccggtt atcactcttg accgccaggc aacgaaaggt    360
gaagtggtga gccacattgc ttctgataac gtactgggcg caaaatcgc tggtgattac     420 atcgcgaaga agcgggtga aggtgccaaa gttatcgagc tgcaaggcat tgctggtaca    480
tccgcagccc gtgaacgtgg cgaaggcttc agcaggccg ttgctgctca caagtttaat    540
gttcttgcca gccagccagc agattttgat cgcattaaag gtttgaacgt aatgcagaac    600
ctgttgaccg ctcatccgga tgttcaggct gtattcgcgc agaatgatga aatgcgctg     660 ggcgcgctgc gcgcactgca aactgccggt aaatcggatg tgatggtcgt cggatttgac    720
ggtacaccgg atggcgaaaa agcggtgaat gatggcaaac tagcagcgac tatcgctcag    780
ctacccgatc agattggcgc gaaaggcgtc gaaaccgcag ataaagtgct gaaaggcgag    840
aaagttcagg ctaagtatcc ggttgatctg aaactggttg ttaagcagta g             891

<210> SEQ ID NO 36
<211> LENGTH: 966
<212> TYPE: DNA
<213> ORGANISM: Escherichia coli

<400> SEQUENCE: 36
atgacaaccc agactgtctc tggtcgccgt tatttcacga aagcgtggct gatggagcag     60
aaatcgctta tcgctctgct ggtgctgatc gcgattgtct cgacgttaag cccgaacttt    120
ttcaccatca taacttatt caatattctc cagcaaacct cagtgaacgc cattatggcg     180
gtcgggatga cgctggtgat cctgacgtcg ggcatcgact tatcggtagg ttctctgttg    240
gcgctgaccg gcgcagttgc tgcatctatc gtcggcattg aagtcaatgc gctggtggct    300
gtcgctgctg ctctcgcgtt aggtgccgca attggtgcgg taaccggggt gattgtagcg    360
aaaggtcgcg tccaggcgtt tatcgctacg ctggttatga tgcttttact gcgcggcgtg    420
accatggttt ataccaacgg tagcccagtg aataccggct ttactgagaa cgccgatctg    480
tttggctggt ttggtattgg tcgtccgctg ggcgtaccga cgccagtctg gatcatgggg    540
```

```
attgtcttcc tcgcggcctg gtacatgctg catcacacgc gtctggggcg ttacatctac    600
gcgctgggcg gcaacgaagc ggcaacgcgt ctttctggta tcaacgtcaa taaaatcaaa    660
atcatcgtct attctctttg tggtctgctg gcatcgctgg ccgggatcat tgaagtggcg    720
cgtctctcct ccgcacaacc cacggcgggg actggctatg agctggatgc tattgctgcg    780
gtggttctgg gcggtacgag tctggcgggc ggaaaaggtc gcattgttgg gacgttgatc    840
ggcgcattaa ttcttggctt ccttaataat ggattgaatt tgttaggtgt ttcctccctat    900 taccagatga tcgtcaaagc ggtggtgatt ttgctggcgg tgctggtaga caacaaaaag    960
cagtaa                                                                966
```

<210> SEQ ID NO 37
<211> LENGTH: 501
<212> TYPE: PRT
<213> ORGANISM: Escherichia coli

<400> SEQUENCE: 37

```
Met Glu Ala Leu Leu Gln Leu Lys Gly Ile Asp Lys Ala Phe Pro Gly
1               5                   10                  15

Val Lys Ala Leu Ser Gly Ala Ala Leu Asn Val Tyr Pro Gly Arg Val
            20                  25                  30

Met Ala Leu Val Gly Glu Asn Gly Ala Gly Lys Ser Thr Met Met Lys
        35                  40                  45

Val Leu Thr Gly Ile Tyr Thr Arg Asp Ala Gly Thr Leu Leu Trp Leu
    50                  55                  60

Gly Lys Glu Thr Thr Phe Thr Gly Pro Lys Ser Gln Glu Ala Gly
65                  70                  75                  80

Ile Gly Ile Ile His Gln Glu Leu Asn Leu Ile Pro Gln Leu Thr Ile
                85                  90                  95

Ala Glu Asn Ile Phe Leu Gly Arg Glu Phe Val Asn Arg Phe Gly Lys
            100                 105                 110

Ile Asp Trp Lys Thr Met Tyr Ala Glu Ala Asp Lys Leu Leu Ala Lys
        115                 120                 125

Leu Asn Leu Arg Phe Lys Ser Asp Lys Leu Val Gly Asp Leu Ser Ile
    130                 135                 140

Gly Asp Gln Gln Met Val Glu Ile Ala Lys Val Leu Ser Phe Glu Ser
145                 150                 155                 160

Lys Val Ile Ile Met Asp Glu Pro Thr Asp Ala Leu Thr Asp Thr Glu
                165                 170                 175

Thr Glu Ser Leu Phe Arg Val Ile Arg Glu Leu Lys Ser Gln Gly Arg
            180                 185                 190

Gly Ile Val Tyr Ile Ser His Arg Met Lys Glu Ile Phe Glu Ile Cys
        195                 200                 205

Asp Asp Val Thr Val Phe Arg Asp Gly Gln Phe Ile Ala Glu Arg Glu
    210                 215                 220

Val Ala Ser Leu Thr Glu Asp Ser Leu Ile Glu Met Met Val Gly Arg
225                 230                 235                 240

Lys Leu Glu Asp Gln Tyr Pro His Leu Asp Lys Ala Pro Gly Asp Ile
                245                 250                 255

Arg Leu Lys Val Asp Asn Leu Cys Gly Pro Gly Val Asn Asp Val Ser
            260                 265                 270

Phe Thr Leu Arg Lys Gly Glu Ile Leu Gly Val Ser Gly Leu Met Gly
        275                 280                 285
```

```
Ala Gly Arg Thr Glu Leu Met Lys Val Leu Tyr Gly Ala Leu Pro Arg
    290                 295                 300

Thr Ser Gly Tyr Val Thr Leu Asp Gly His Glu Val Val Thr Arg Ser
305                 310                 315                 320

Pro Gln Asp Gly Leu Ala Asn Gly Ile Val Tyr Ile Ser Glu Asp Arg
                325                 330                 335

Lys Arg Asp Gly Leu Val Leu Gly Met Ser Val Lys Glu Asn Met Ser
            340                 345                 350

Leu Thr Ala Leu Arg Tyr Phe Ser Arg Ala Gly Gly Ser Leu Lys His
        355                 360                 365

Ala Asp Glu Gln Gln Ala Val Ser Asp Phe Ile Arg Leu Phe Asn Val
370                 375                 380

Lys Thr Pro Ser Met Glu Gln Ala Ile Gly Leu Leu Ser Gly Gly Asn
385                 390                 395                 400

Gln Gln Lys Val Ala Ile Ala Arg Gly Leu Met Thr Arg Pro Lys Val
                405                 410                 415

Leu Ile Leu Asp Glu Pro Thr Arg Gly Val Asp Val Gly Ala Lys Lys
            420                 425                 430

Glu Ile Tyr Gln Leu Ile Asn Gln Phe Lys Ala Asp Gly Leu Ser Ile
        435                 440                 445

Ile Leu Val Ser Ser Glu Met Pro Glu Val Leu Gly Met Ser Asp Arg
450                 455                 460

Ile Ile Val Met His Glu Gly His Leu Ser Gly Glu Phe Thr Arg Glu
465                 470                 475                 480

Gln Ala Thr Gln Glu Val Leu Met Ala Ala Val Gly Lys Leu Asn
                485                 490                 495

Arg Val Asn Gln Glu
            500

<210> SEQ ID NO 38
<211> LENGTH: 296
<212> TYPE: PRT
<213> ORGANISM: Escherichia coli

<400> SEQUENCE: 38

Met Asn Met Lys Lys Leu Ala Thr Leu Val Ser Ala Val Ala Leu Ser
1               5                   10                  15

Ala Thr Val Ser Ala Asn Ala Met Ala Lys Asp Thr Ile Ala Leu Val
            20                  25                  30

Val Ser Thr Leu Asn Asn Pro Phe Phe Val Ser Leu Lys Asp Gly Ala
        35                  40                  45

Gln Lys Glu Ala Asp Lys Leu Gly Tyr Asn Leu Val Val Leu Asp Ser
    50                  55                  60

Gln Asn Asn Pro Ala Lys Glu Leu Ala Asn Val Gln Asp Leu Thr Val
65                  70                  75                  80

Arg Gly Thr Lys Ile Leu Leu Ile Asn Pro Thr Asp Ser Asp Ala Val
                85                  90                  95

Gly Asn Ala Val Lys Met Ala Asn Gln Ala Asn Ile Pro Val Ile Thr
            100                 105                 110

Leu Asp Arg Gln Ala Thr Lys Gly Glu Val Val Ser His Ile Ala Ser
        115                 120                 125

Asp Asn Val Leu Gly Gly Lys Ile Ala Gly Asp Tyr Ile Ala Lys Lys
    130                 135                 140

Ala Gly Glu Gly Ala Lys Val Ile Glu Leu Gln Gly Ile Ala Gly Thr
145                 150                 155                 160
```

```
Ser Ala Ala Arg Glu Arg Gly Glu Gly Phe Gln Gln Ala Val Ala Ala
            165                 170                 175

His Lys Phe Asn Val Leu Ala Ser Gln Pro Ala Asp Phe Asp Arg Ile
        180                 185                 190

Lys Gly Leu Asn Val Met Gln Asn Leu Leu Thr Ala His Pro Asp Val
    195                 200                 205

Gln Ala Val Phe Ala Gln Asn Asp Glu Met Ala Leu Gly Ala Leu Arg
210                 215                 220

Ala Leu Gln Thr Ala Gly Lys Ser Asp Val Met Val Gly Phe Asp
225                 230                 235                 240

Gly Thr Pro Asp Gly Glu Lys Ala Val Asn Asp Gly Lys Leu Ala Ala
                245                 250                 255

Thr Ile Ala Gln Leu Pro Asp Gln Ile Gly Ala Lys Gly Val Glu Thr
                260                 265                 270

Ala Asp Lys Val Leu Lys Gly Glu Lys Val Gln Ala Lys Tyr Pro Val
            275                 280                 285

Asp Leu Lys Leu Val Val Lys Gln
290                 295

<210> SEQ ID NO 39
<211> LENGTH: 321
<212> TYPE: PRT
<213> ORGANISM: Escherichia coli

<400> SEQUENCE: 39

Met Thr Thr Gln Thr Val Ser Gly Arg Arg Tyr Phe Thr Lys Ala Trp
1               5                   10                  15

Leu Met Glu Gln Lys Ser Leu Ile Ala Leu Leu Val Leu Ile Ala Ile
                20                  25                  30

Val Ser Thr Leu Ser Pro Asn Phe Phe Thr Ile Asn Asn Leu Phe Asn
            35                  40                  45

Ile Leu Gln Gln Thr Ser Val Asn Ala Ile Met Ala Val Gly Met Thr
        50                  55                  60

Leu Val Ile Leu Thr Ser Gly Ile Asp Leu Ser Val Gly Ser Leu Leu
65                  70                  75                  80

Ala Leu Thr Gly Ala Val Ala Ala Ser Ile Val Gly Ile Glu Val Asn
                85                  90                  95

Ala Leu Val Ala Val Ala Ala Leu Ala Leu Gly Ala Ala Ile Gly
            100                 105                 110

Ala Val Thr Gly Val Ile Val Ala Lys Gly Arg Val Gln Ala Phe Ile
        115                 120                 125

Ala Thr Leu Val Met Met Leu Leu Leu Arg Gly Val Thr Met Val Tyr
    130                 135                 140

Thr Asn Gly Ser Pro Val Asn Thr Gly Phe Thr Glu Asn Ala Asp Leu
145                 150                 155                 160

Phe Gly Trp Phe Gly Ile Gly Arg Pro Leu Gly Val Pro Thr Pro Val
                165                 170                 175

Trp Ile Met Gly Ile Val Phe Leu Ala Ala Trp Tyr Met Leu His His
                180                 185                 190

Thr Arg Leu Gly Arg Tyr Ile Tyr Ala Leu Gly Gly Asn Glu Ala Ala
            195                 200                 205

Thr Arg Leu Ser Gly Ile Asn Val Asn Lys Ile Lys Ile Ile Val Tyr
        210                 215                 220

Ser Leu Cys Gly Leu Leu Ala Ser Leu Ala Gly Ile Ile Glu Val Ala
```

```
            225                 230                 235                 240
Arg Leu Ser Ser Ala Gln Pro Thr Ala Gly Thr Gly Tyr Glu Leu Asp
                245                 250                 255

Ala Ile Ala Ala Val Val Leu Gly Gly Thr Ser Leu Ala Gly Gly Lys
            260                 265                 270

Gly Arg Ile Val Gly Thr Leu Ile Gly Ala Leu Ile Leu Gly Phe Leu
        275                 280                 285

Asn Asn Gly Leu Asn Leu Leu Gly Val Ser Ser Tyr Tyr Gln Met Ile
    290                 295                 300

Val Lys Ala Val Val Ile Leu Leu Ala Val Leu Val Asp Asn Lys Lys
305                 310                 315                 320

Gln

<210> SEQ ID NO 40
<211> LENGTH: 1533
<212> TYPE: DNA
<213> ORGANISM: Escherichia coli

<400> SEQUENCE: 40
atggccacgc catatatatc gatggcgggg atcggcaagt cctttggtcc ggttcacgca     60
ttaaagtcgg ttaatttaac ggtttatcct ggtgaaatac atgcattact aggagaaaat    120
ggcgcgggta atccacgct aatgaaagtt ttatccggaa tacatgagcc gaccaaaggc     180
accattacca ttaataacat tagctataac aagctggatc ataaattagc ggcacaactc    240
ggtatcggga ttatttatca ggaactcagc gttattgatg aattaaccgt actggaaaat    300
ttatatattg gtcgtcatct gacgaaaaaa atctgtggcg tcaatattat cgactggcga    360
gaaatgcgtg tccgcgccgc catgatgtta ttacgcgtgg gcttgaaagt tgatctagat    420
gagaaagtgg cgaatttatc tatcagccac aagcagatgc tagaaattgc caaaacgctg    480
atgctcgatg ccaaagtcat catcatggat gaacccacct cctcactcac caataaagag    540
gtggactatc tgtttctgat catgaatcag ttgcgtaaag agggtacggc catcgtctat    600
atctcgcata gttggcgga aattcgccgt atttgcgacc gctatacggt gatgaaagac    660
ggcagcagcg tttgcagcgg catagtaagc gatgtgtcaa atgacgatat cgtccgtctg    720
atggtaggcc gcgaactgca aaaccgtttt aacgcgatga aggagaatgt cagcaacctt    780
gcgcacgaaa cggttttttga ggtgcggaac gtcaccagtc gtgacagaaa aaaggtccgg    840
gatatctcat ttagcgtctg ccggggagaa atattaggct tgccggact ggtcggttcc    900 ggacgtactg aactgatgaa ttgtctgttt ggcgtgata acgcgctgg cggagaaatc    960 cgtcttaatg gcaaagatat ctctccacgt tcacccctgg atgccgtgaa aaagggatg   1020 gcttacatca ctgaaagccg ccgggataac ggtttttcc ccaactttc catcgctcag   1080 aacatggcga tcagccgcag tctgaaagac ggcggctata aggcgcgat gggcttgttt   1140 catgaagttg acgagcaacg taccgctgaa atcaacgcg aactgctggc gctgaaatgt   1200
cattcggtaa accagaatat caccgaactc tccggggaa atcagcagaa agtcctgatc   1260
tccaaatggc tgtgctgttg cccggaagtg attatttcg atgaacctac ccgcggcatc   1320
gacgttggcg cgaaagccga aatttacaaa gtgatgcgcc aactggcgga cgacggaaaa   1380
gtcatcctga tggtgtcatc tgaactacct gaaattatca ccgtctgcga ccgcatcgcc   1440
gtgttctgcg aaggacgact gacgcaaatc ctgacgaatc gcgatgacat gagcgaagag   1500
gagattatgg catgggcttt accacaagag taa                                1533
```

<210> SEQ ID NO 41
<211> LENGTH: 936
<212> TYPE: DNA
<213> ORGANISM: Escherichia coli

<400> SEQUENCE: 41

| | | | | | | |
|---|---|---|---|---|---|---|
| atgaataaat | atctgaaata | tttcagcggc | acactcgtgg | gcttaatgtt | gtcaaccagc | 60 |
| gcttttgctg | ccgccgaata | tgctgtcgta | ttgaaaaccc | tctccaaccc | attttgggta | 120 |
| gatatgaaaa | aaggcattga | agatgaagca | aaaacactgg | gcgtcagcgt | tgatattttt | 180 |
| gcctctcctt | cagaaggcga | ttttcaatct | caattgcagt | tatttgaaga | tctcagtaat | 240 |
| aaaaattaca | aaggtatcgc | cttcgctcca | ttatcctcag | tgaatctggt | catgcctgtc | 300 |
| gcccgcgcat | ggaaaaaagg | catttatctg | gttaatctcg | atgaaaaaat | cgacatggat | 360 |
| aatctgaaaa | aagctggcgg | caatgtggaa | gcttttgtca | ccaccgataa | cgttgctgtc | 420 |
| ggggcgaaag | gcgcgtcgtt | cattattgac | aaattgggcg | ctgaaggtgg | tgaagtcgca | 480 |
| atcattgagg | gtaaagccgg | taacgcctcc | ggtgaagcgc | gtcgtaatgg | tgccaccgaa | 540 |
| gccttcaaaa | aagcaagcca | gatcaagctt | gtcgccagcc | agcctgccga | ctgggaccgc | 600 |
| attaaagcac | tggatgtcgc | cactaacgtg | ttgcaacgta | tccgaatat | aaagcgatc | 660 |
| tattgcgcga | atgacacgat | ggcaatgggt | gttgctcagg | cagtcgcaaa | cgccggaaaa | 720 |
| acgggaaaag | tgctggtcgt | cggtacagat | ggcattccgg | aagcccgcaa | aatggtggaa | 780 |
| gccggacaaa | tgaccgcgac | ggttgcccag | aacccggcgg | atatcggcgc | aacgggtctg | 840 |
| aagctgatgt | tgacgctga | aaatccggc | aaggttatcc | cgctggataa | agcaccggaa | 900 |
| tttaaactgg | tcgattcaat | cctggtcact | caataa | | | 936 |

<210> SEQ ID NO 42
<211> LENGTH: 981
<212> TYPE: DNA
<213> ORGANISM: Escherichia coli

<400> SEQUENCE: 42

| | | | | | | |
|---|---|---|---|---|---|---|
| atgggcttta | ccacaagagt | aaaaagcgaa | gcgagcgaga | agaaaccgtt | caactttgcg | 60 |
| ctgttctggg | ataaatacgg | caccttttt | atcctggcga | tcatcgtcgc | catctttggt | 120 |
| tcgctgtcac | cagaatattt | tctgaccacc | aataatatta | cccagatttt | tgttcaaagc | 180 |
| tccgtgacgg | tattgatcgg | catgggcgag | ttttcgcta | tcctggtcgc | tggtatcgac | 240 |
| ctctcggttg | gcgcgattct | ggcgcttcc | ggtatggtga | ccgccaaact | gatgttggca | 300 |
| ggtgttgacc | cgtttctcgc | agcgatgatt | ggcggtgtac | tggttggcgg | cgcactgggg | 360 |
| gcgatcaacg | gctgcctggt | caactggacg | gggctacacc | cgttcatcat | cacccttggc | 420 |
| accaacgcga | ttttccgtgg | gatcacgctg | gtgatctccg | atgccaactc | ggtatacggc | 480 |
| ttctcatttg | acttcgtgaa | cttctttgcc | gccagcgtaa | ttgggatacc | tgtccccgtt | 540 |
| atcttctcac | taattgtcgc | gctcatcctt | tggtttctga | caacgcgtat | gcggctcggg | 600 |
| cgcaacatct | acgcactggg | cggcaacaaa | aattcggcgt | tctattccgg | gattgacgtg | 660 |
| aaattccaca | tcctggtggt | gtttatcatc | tccggtgttt | gtgcaggtct | ggcaggcgtc | 720 |
| gtctcaactg | cacgactcgg | tgccgcagaa | ccgcttgccg | gtatgggttt | tgaaacctat | 780 |
| gccattgcca | cgcgccatcat | tggcggcacc | agtttcttcg | gcggcaaggg | gcgcattttc | 840 |
| tctgtggtga | ttggcgggtt | gatcatcggc | accatcaaca | acggtctgaa | tattttgcag | 900 |
| gtacaaacct | attccaact | ggtggtgatg | ggcggattaa | ttatcgcggc | tgtcgcccctt | 960 | gaccgtctta tcagtaagta a        981

<210> SEQ ID NO 43
<211> LENGTH: 510
<212> TYPE: PRT
<213> ORGANISM: Escherichia coli

<400> SEQUENCE: 43

```
Met Ala Thr Pro Tyr Ile Ser Met Ala Gly Ile Gly Lys Ser Phe Gly
1               5                   10                  15

Pro Val His Ala Leu Lys Ser Val Asn Leu Thr Val Tyr Pro Gly Glu
            20                  25                  30

Ile His Ala Leu Leu Gly Glu Asn Gly Ala Gly Lys Ser Thr Leu Met
        35                  40                  45

Lys Val Leu Ser Gly Ile His Glu Pro Thr Lys Gly Thr Ile Thr Ile
    50                  55                  60

Asn Asn Ile Ser Tyr Asn Lys Leu Asp His Lys Leu Ala Ala Gln Leu
65                  70                  75                  80

Gly Ile Gly Ile Ile Tyr Gln Glu Leu Ser Val Ile Asp Glu Leu Thr
                85                  90                  95

Val Leu Glu Asn Leu Tyr Ile Gly Arg His Leu Thr Lys Lys Ile Cys
            100                 105                 110

Gly Val Asn Ile Ile Asp Trp Arg Glu Met Arg Val Arg Ala Ala Met
        115                 120                 125

Met Leu Leu Arg Val Gly Leu Lys Val Asp Leu Asp Glu Lys Val Ala
    130                 135                 140

Asn Leu Ser Ile Ser His Lys Gln Met Leu Glu Ile Ala Lys Thr Leu
145                 150                 155                 160

Met Leu Asp Ala Lys Val Ile Ile Met Asp Glu Pro Thr Ser Ser Leu
                165                 170                 175

Thr Asn Lys Glu Val Asp Tyr Leu Phe Leu Ile Met Asn Gln Leu Arg
            180                 185                 190

Lys Glu Gly Thr Ala Ile Val Tyr Ile Ser His Lys Leu Ala Glu Ile
        195                 200                 205

Arg Arg Ile Cys Asp Arg Tyr Thr Val Met Lys Asp Gly Ser Ser Val
    210                 215                 220

Cys Ser Gly Ile Val Ser Asp Val Ser Asn Asp Ile Val Arg Leu
225                 230                 235                 240

Met Val Gly Arg Glu Leu Gln Asn Arg Phe Asn Ala Met Lys Glu Asn
                245                 250                 255

Val Ser Asn Leu Ala His Glu Thr Val Phe Glu Val Arg Asn Val Thr
            260                 265                 270

Ser Arg Asp Arg Lys Lys Val Arg Asp Ile Ser Phe Ser Val Cys Arg
        275                 280                 285

Gly Glu Ile Leu Gly Phe Ala Gly Leu Val Gly Ser Gly Arg Thr Glu
    290                 295                 300

Leu Met Asn Cys Leu Phe Gly Val Asp Lys Arg Ala Gly Gly Glu Ile
305                 310                 315                 320

Arg Leu Asn Gly Lys Asp Ile Ser Pro Arg Ser Pro Leu Asp Ala Val
                325                 330                 335

Lys Lys Gly Met Ala Tyr Ile Thr Glu Ser Arg Arg Asp Asn Gly Phe
            340                 345                 350

Phe Pro Asn Phe Ser Ile Ala Gln Asn Met Ala Ile Ser Arg Ser Leu
        355                 360                 365
```

```
Lys Asp Gly Gly Tyr Lys Gly Ala Met Gly Leu Phe His Glu Val Asp
        370                 375                 380

Glu Gln Arg Thr Ala Glu Asn Gln Arg Glu Leu Ala Leu Lys Cys
385                 390                 395                 400

His Ser Val Asn Gln Asn Ile Thr Glu Leu Ser Gly Gly Asn Gln Gln
                405                 410                 415

Lys Val Leu Ile Ser Lys Trp Leu Cys Cys Cys Pro Glu Val Ile Ile
            420                 425                 430

Phe Asp Glu Pro Thr Arg Gly Ile Asp Val Gly Ala Lys Ala Glu Ile
        435                 440                 445

Tyr Lys Val Met Arg Gln Leu Ala Asp Asp Gly Lys Val Ile Leu Met
    450                 455                 460

Val Ser Ser Glu Leu Pro Glu Ile Ile Thr Val Cys Asp Arg Ile Ala
465                 470                 475                 480

Val Phe Cys Glu Gly Arg Leu Thr Gln Ile Leu Thr Asn Arg Asp Asp
                485                 490                 495

Met Ser Glu Glu Glu Ile Met Ala Trp Ala Leu Pro Gln Glu
                500                 505                 510

<210> SEQ ID NO 44
<211> LENGTH: 311
<212> TYPE: PRT
<213> ORGANISM: Escherichia coli

<400> SEQUENCE: 44

Met Asn Lys Tyr Leu Lys Tyr Phe Ser Gly Thr Leu Val Gly Leu Met
1               5                   10                  15

Leu Ser Thr Ser Ala Phe Ala Ala Glu Tyr Ala Val Val Leu Lys
            20                  25                  30

Thr Leu Ser Asn Pro Phe Trp Val Asp Met Lys Lys Gly Ile Glu Asp
            35                  40                  45

Glu Ala Lys Thr Leu Gly Val Ser Val Asp Ile Phe Ala Ser Pro Ser
    50                  55                  60

Glu Gly Asp Phe Gln Ser Gln Leu Gln Leu Phe Glu Asp Leu Ser Asn
65                  70                  75                  80

Lys Asn Tyr Lys Gly Ile Ala Phe Ala Pro Leu Ser Ser Val Asn Leu
                85                  90                  95

Val Met Pro Val Ala Arg Ala Trp Lys Lys Gly Ile Tyr Leu Val Asn
            100                 105                 110

Leu Asp Glu Lys Ile Asp Met Asp Asn Leu Lys Lys Ala Gly Gly Asn
        115                 120                 125

Val Glu Ala Phe Val Thr Thr Asp Asn Val Ala Val Gly Ala Lys Gly
    130                 135                 140

Ala Ser Phe Ile Ile Asp Lys Leu Gly Ala Glu Gly Gly Glu Val Ala
145                 150                 155                 160

Ile Ile Glu Gly Lys Ala Gly Asn Ala Ser Gly Glu Ala Arg Arg Asn
                165                 170                 175

Gly Ala Thr Glu Ala Phe Lys Lys Ala Ser Gln Ile Lys Leu Val Ala
            180                 185                 190

Ser Gln Pro Ala Asp Trp Asp Arg Ile Lys Ala Leu Asp Val Ala Thr
        195                 200                 205

Asn Val Leu Gln Arg Asn Pro Asn Ile Lys Ala Ile Tyr Cys Ala Asn
    210                 215                 220

Asp Thr Met Ala Met Gly Val Ala Gln Ala Val Ala Asn Ala Gly Lys
```

```
                225                 230                 235                 240

Thr Gly Lys Val Leu Val Val Gly Thr Asp Gly Ile Pro Glu Ala Arg
                        245                 250                 255

Lys Met Val Glu Ala Gly Gln Met Thr Ala Thr Val Ala Gln Asn Pro
                        260                 265                 270

Ala Asp Ile Gly Ala Thr Gly Leu Lys Leu Met Val Asp Ala Glu Lys
                        275                 280                 285

Ser Gly Lys Val Ile Pro Leu Asp Lys Ala Pro Glu Phe Lys Leu Val
                        290                 295                 300

Asp Ser Ile Leu Val Thr Gln
        305                 310

<210> SEQ ID NO 45
<211> LENGTH: 326
<212> TYPE: PRT
<213> ORGANISM: Escherichia coli

<400> SEQUENCE: 45

Met Gly Phe Thr Thr Arg Val Lys Ser Glu Ala Ser Glu Lys Lys Pro
1               5                   10                  15

Phe Asn Phe Ala Leu Phe Trp Asp Lys Tyr Gly Thr Phe Phe Ile Leu
            20                  25                  30

Ala Ile Ile Val Ala Ile Phe Gly Ser Leu Ser Pro Glu Tyr Phe Leu
        35                  40                  45

Thr Thr Asn Asn Ile Thr Gln Ile Phe Val Gln Ser Ser Val Thr Val
    50                  55                  60

Leu Ile Gly Met Gly Glu Phe Phe Ala Ile Leu Val Ala Gly Ile Asp
65                  70                  75                  80

Leu Ser Val Gly Ala Ile Leu Ala Leu Ser Gly Met Val Thr Ala Lys
                85                  90                  95

Leu Met Leu Ala Gly Val Asp Pro Phe Leu Ala Ala Met Ile Gly Gly
            100                 105                 110

Val Leu Val Gly Gly Ala Leu Gly Ala Ile Asn Gly Cys Leu Val Asn
        115                 120                 125

Trp Thr Gly Leu His Pro Phe Ile Ile Thr Leu Gly Thr Asn Ala Ile
    130                 135                 140

Phe Arg Gly Ile Thr Leu Val Ile Ser Asp Ala Asn Ser Val Tyr Gly
145                 150                 155                 160

Phe Ser Phe Asp Phe Val Asn Phe Phe Ala Ala Ser Val Ile Gly Ile
                165                 170                 175

Pro Val Pro Val Ile Phe Ser Leu Ile Val Ala Leu Ile Leu Trp Phe
            180                 185                 190

Leu Thr Thr Arg Met Arg Leu Gly Arg Asn Ile Tyr Ala Leu Gly Gly
        195                 200                 205

Asn Lys Asn Ser Ala Phe Tyr Ser Gly Ile Asp Val Lys Phe His Ile
    210                 215                 220

Leu Val Val Phe Ile Ile Ser Gly Val Cys Ala Gly Leu Ala Gly Val
225                 230                 235                 240

Val Ser Thr Ala Arg Leu Gly Ala Ala Glu Pro Leu Ala Gly Met Gly
                245                 250                 255

Phe Glu Thr Tyr Ala Ile Ala Ser Ala Ile Ile Gly Gly Thr Ser Phe
            260                 265                 270

Phe Gly Gly Lys Gly Arg Ile Phe Ser Val Val Ile Gly Gly Leu Ile
        275                 280                 285
```

Ile Gly Thr Ile Asn Asn Gly Leu Asn Ile Leu Gln Val Gln Thr Tyr
            290                 295                 300

Tyr Gln Leu Val Val Met Gly Gly Leu Ile Ile Ala Ala Val Ala Leu
305                 310                 315                 320

Asp Arg Leu Ile Ser Lys
            325

<210> SEQ ID NO 46
<211> LENGTH: 1419
<212> TYPE: DNA
<213> ORGANISM: Escherichia coli

<400> SEQUENCE: 46

| | | |
|---|---|---|
| atggttacta tcaatacgga atctgcttta acgccacgtt ctttgcggga tacgcggcgt | 60 |
| atgaatatgt tgtttcggt agctgctgcg gtcgcaggat tgttatttgg tcttgatatc | 120 |
| ggcgtaatcg ccggagcgtt gccgttcatt accgatcact ttgtgctgac cagtcgtttg | 180 |
| caggaatggg tggttagtag catgatgctc ggtgcagcaa ttggtgcgct gtttaatggt | 240 |
| tggctgtcgt tccgcctggg gcgtaaatac agcctgatgg cggggccat cctgtttgta | 300 |
| ctcggttcta tagggtccgc ttttgcgacc agcgtagaga tgttaatcgc cgtcgtgtg | 360 |
| gtgctgggca ttgctgtcgg gatcgcgtct acaccgctc ctctgtatct ttctgaaatg | 420 |
| gcaagtgaaa acgttcgcgg taagatgatc agtatgtacc agttgatggt cacactcggc | 480 |
| atcgtgctgg cgttttatc cgatacagcg ttcagttata gcggtaactg gcgcgcaatg | 540 |
| ttggggttc ttgctttacc agcagttctg ctgattattc tggtagtctt cctgccaaat | 600 |
| agcccgcgct ggctggcgga aaaggggcgt catattgagg cggaagaagt attgcgtatg | 660 |
| ctgcgcgata cgtcggaaaa agcgcgagaa gaactcaacg aaattcgtga agcctgaag | 720 |
| ttaaaacagg gcggttgggc actgtttaag atcaaccgta acgtccgtcg tgctgtgttt | 780 |
| ctcggtatgt tgttgcaggc gatgcagcag tttaccggta tgaacatcat catgtactac | 840 |
| gcgccgcgta tcttcaaaat ggcgggcttt acgaccacag aacaacagat gattgcgact | 900 |
| ctggtcgtag gctgaccctt tatgttcgcc acctttattg cggtgtttac ggtagataaa | 960 |
| gcagggcgta accggctctc gaaaattggt ttcagcgtga tggcgttagg cactctggtg | 1020 |
| ctgggctatt gcctgatgca gtttgataac ggtacggctt ccagtggctt gtcctggctc | 1080 |
| tctgttggca tgacgatgat gtgtattgcc ggttatgcga tgagcgccgc gccagtggtg | 1140 |
| tggatcctgt gctctgaaat tcagccgctg aaatgccgcg atttcggtat acctgttcg | 1200 |
| accaccacga actgggtgtc gaatatgatt atcggcgcga ccttcctgac actgcttgat | 1260 |
| agcattggcg ctgccggtac gttctggctc tacactgcgc tgaacattgc gtttgtgggc | 1320 |
| attactttct ggctcattcc ggaaaccaaa aatgtcacgc tggaacatat cgaacgcaaa | 1380 |
| ctgatggcag gcgagaagtt gagaaatatc ggcgtctga | 1419 |

<210> SEQ ID NO 47
<211> LENGTH: 472
<212> TYPE: PRT
<213> ORGANISM: Escherichia coli

<400> SEQUENCE: 47

Met Val Thr Ile Asn Thr Glu Ser Ala Leu Thr Pro Arg Ser Leu Arg
1               5                   10                  15

Asp Thr Arg Arg Met Asn Met Phe Val Ser Val Ala Ala Ala Val Ala
            20                  25                  30

```
Gly Leu Leu Phe Gly Leu Asp Ile Gly Val Ile Ala Gly Ala Leu Pro
             35                  40                  45

Phe Ile Thr Asp His Phe Val Leu Thr Ser Arg Leu Gln Glu Trp Val
 50                  55                  60

Val Ser Ser Met Met Leu Gly Ala Ala Ile Gly Ala Leu Phe Asn Gly
 65                  70                  75                  80

Trp Leu Ser Phe Arg Leu Gly Arg Lys Tyr Ser Leu Met Ala Gly Ala
                 85                  90                  95

Ile Leu Phe Val Leu Gly Ser Ile Gly Ser Ala Phe Ala Thr Ser Val
                100                 105                 110

Glu Met Leu Ile Ala Ala Arg Val Val Leu Gly Ile Ala Val Gly Ile
             115                 120                 125

Ala Ser Tyr Thr Ala Pro Leu Tyr Leu Ser Glu Met Ala Ser Glu Asn
     130                 135                 140

Val Arg Gly Lys Met Ile Ser Met Tyr Gln Leu Met Val Thr Leu Gly
145                 150                 155                 160

Ile Val Leu Ala Phe Leu Ser Asp Thr Ala Phe Ser Tyr Ser Gly Asn
                165                 170                 175

Trp Arg Ala Met Leu Gly Val Leu Ala Leu Pro Ala Val Leu Leu Ile
             180                 185                 190

Ile Leu Val Val Phe Leu Pro Asn Ser Pro Arg Trp Leu Ala Glu Lys
         195                 200                 205

Gly Arg His Ile Glu Ala Glu Val Leu Arg Met Leu Arg Asp Thr
     210                 215                 220

Ser Glu Lys Ala Arg Glu Glu Leu Asn Glu Ile Arg Glu Ser Leu Lys
225                 230                 235                 240

Leu Lys Gln Gly Gly Trp Ala Leu Phe Lys Ile Asn Arg Asn Val Arg
                245                 250                 255

Arg Ala Val Phe Leu Gly Met Leu Leu Gln Ala Met Gln Gln Phe Thr
             260                 265                 270

Gly Met Asn Ile Ile Met Tyr Tyr Ala Pro Arg Ile Phe Lys Met Ala
     275                 280                 285

Gly Phe Thr Thr Thr Glu Gln Gln Met Ile Ala Thr Leu Val Val Gly
     290                 295                 300

Leu Thr Phe Met Phe Ala Thr Phe Ile Ala Val Phe Thr Val Asp Lys
305                 310                 315                 320

Ala Gly Arg Lys Pro Ala Leu Lys Ile Gly Phe Ser Val Met Ala Leu
                325                 330                 335

Gly Thr Leu Val Leu Gly Tyr Cys Leu Met Gln Phe Asp Asn Gly Thr
             340                 345                 350

Ala Ser Ser Gly Leu Ser Trp Leu Ser Val Gly Met Thr Met Met Cys
     355                 360                 365

Ile Ala Gly Tyr Ala Met Ser Ala Ala Pro Val Val Trp Ile Leu Cys
     370                 375                 380

Ser Glu Ile Gln Pro Leu Lys Cys Arg Asp Phe Gly Ile Thr Cys Ser
385                 390                 395                 400

Thr Thr Thr Asn Trp Val Ser Asn Met Ile Ile Gly Ala Thr Phe Leu
                405                 410                 415

Thr Leu Leu Asp Ser Ile Gly Ala Ala Gly Thr Phe Trp Leu Tyr Thr
             420                 425                 430

Ala Leu Asn Ile Ala Phe Val Gly Ile Thr Phe Trp Leu Ile Pro Glu
     435                 440                 445

Thr Lys Asn Val Thr Leu Glu His Ile Glu Arg Lys Leu Met Ala Gly
```

```
            450                 455                 460
Glu Lys Leu Arg Asn Ile Gly Val
465                 470

<210> SEQ ID NO 48
<211> LENGTH: 1476
<212> TYPE: DNA
<213> ORGANISM: Escherichia coli

<400> SEQUENCE: 48
atgaataccc agtataattc cagttatata ttttcgatta ccttagtcgc tacattaggt      60
ggtttattat ttggctacga caccgccgtt atttccggta ctgttgagtc actcaatacc    120
gtctttgttg ctccacaaaa cttaagtgaa tccgctgcca actccctgtt agggttttgc    180
gtggccagcg ctctgattgg ttgcatcatc ggcggtgccc tcggtggtta ttgcagtaac    240
cgcttcggtc gtcgtgattc acttaagatt gctgctgtcc tgttttttat ttctggtgta    300
ggttctgcct ggccagaact tggttttacc tctataaacc cggacaacac tgtgcctgtt    360
tatctggcag gttatgtccc ggaatttgtt atttatcgca ttattggcgg tattggcgtt    420
ggtttagcct caatgctctc gccaatgtat attgcggaac tggctccagc tcatattcgc    480
gggaaactgg tctcttttaa ccagtttgcg attattttcg gcaacttttt agtttactgc    540
gtaaactatt ttattgcccg ttccggtgat gccagctggc tgaatactga cggctggcgt    600
tatatgtttg cctcggaatg tatccctgca ctgctgttct aatgctgct gtataccgtg    660 ccagaaagtc ctcgctggct gatgtcgcgc ggcaagcaag aacaggcgga aggtatcctg    720
cgcaaaatta tgggcaacac gcttgcaact caggcagtac aggaaattaa acactccctg    780
gatcatggcc gcaaaaccgg tggtcgtctg ctgatgtttg cgtgggcgt gattgtaatc    840 ggcgtaatgc tctccatctt ccagcaattt gtcggcatca atgtggtgct gtactacgcg    900
ccggaagtgt tcaaaacgct gggggccagc acggatatcg cgctgttgca gaccattatt    960
gtcggagtta tcaacctcac cttcaccgtt ctggcaatta tgacggtgga taaatttggt   1020
cgtaagccac tgcaaattat cggcgcactc ggaatggcaa tcggtatgtt tagcctcggt   1080
accgcgtttt acactcaggc accgggtatt gtggcgctac tgtcgatgct gttctatgtt   1140
gccgcctttg ccatgtcctg ggtccggta tgctgggtac tgctgtcgga atcttcccg    1200 aatgctattc gtggtaaagc gctggcaatc gcggtggcgg cccagtggct ggcgaactac   1260
ttcgtctcct ggaccttccc gatgatggac aaaaactcct ggctggtggc ccatttccac   1320
aacggtttct cctactggat ttacggttgt atgggcgttc tggcagcact gtttatgtgg   1380
aaatttgtcc cggaaaccaa aggtaaaacc cttgaggagc tggaagcgct ctgggaaccg   1440
gaaacgaaga aaacacaaca aactgctacg ctgtaa                            1476

<210> SEQ ID NO 49
<211> LENGTH: 491
<212> TYPE: PRT
<213> ORGANISM: Escherichia coli

<400> SEQUENCE: 49

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
                20                  25                  30

Gly Thr Val Glu Ser Leu Asn Thr Val Phe Val Ala Pro Gln Asn Leu
        35                  40                  45
```

```
Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Gly Tyr Cys Ser Asn
 65                  70                  75                  80

Arg Phe Gly Arg Arg Asp Ser Leu Lys Ile Ala Ala Val Leu Phe Phe
                 85                  90                  95

Ile Ser Gly Val Gly Ser Ala Trp Pro Glu Leu Gly Phe Thr Ser Ile
                100                 105                 110

Asn Pro Asp Asn Thr Val Pro Val Tyr Leu Ala Gly Tyr Val Pro Glu
                115                 120                 125

Phe Val Ile Tyr Arg Ile Ile Gly Gly Ile Gly Val Gly Leu Ala Ser
130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
                180                 185                 190

Trp Leu Asn Thr Asp Gly Trp Arg Tyr Met Phe Ala Ser Glu Cys Ile
                195                 200                 205

Pro Ala Leu Leu Phe Leu Met Leu Leu Tyr Thr Val Pro Glu Ser Pro
210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
                260                 265                 270

Phe Gly Val Gly Val Ile Val Ile Gly Val Met Leu Ser Ile Phe Gln
                275                 280                 285

Gln Phe Val Gly Ile Asn Val Val Leu Tyr Tyr Ala Pro Glu Val Phe
                290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335

Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Pro
                355                 360                 365

Gly Ile Val Ala Leu Leu Ser Met Leu Phe Tyr Val Ala Ala Phe Ala
                370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
                420                 425                 430

Ser Trp Leu Val Ala His Phe His Asn Gly Phe Ser Tyr Trp Ile Tyr
                435                 440                 445

Gly Cys Met Gly Val Leu Ala Ala Leu Phe Met Trp Lys Phe Val Pro
450                 455                 460
```

```
Glu Thr Lys Gly Lys Thr Leu Glu Glu Leu Glu Ala Leu Trp Glu Pro
465                 470                 475                 480

Glu Thr Lys Lys Thr Gln Gln Thr Ala Thr Leu
            485                 490
```

<210> SEQ ID NO 50
<211> LENGTH: 1095
<212> TYPE: DNA
<213> ORGANISM: Homo sapiens

<400> SEQUENCE: 50

```
atggcgcacc gttttccggc gctgacccaa gagcagaaga aggagctgag cgagattgcg    60
cagagcatcg tggcgaatgg taaaggtatt ctggcggcgg atgagagcgt tggtaccatg   120
ggcaaccgtc tgcagcgtat taaggtggag aacaccgagg aaaaccgtcg tcaattccgt   180
gaaatcctgt ttagcgttga tagcagcatc aaccagagca ttggtggcgt gatcctgttc   240
cacgaaaccc tgtaccagaa ggacagccaa ggtaaactgt ttcgtaacat tctgaaggaa   300
aaaggtattg tggttggcat caagctggat caaggtggcg cgccgctggc gggcaccaac   360
aaggaaacca ccatccaggg tctggacggc ctgagcgaac gttgcgcgca atataagaaa   420
gatggtgttg acttcggcaa gtggcgtgcg gtgctgcgta ttgcggacca gtgcccgagc   480
agcctggcga tccaagaaaa cgcgaacgcg ctggcgcgtt acgcgagcat ctgccagcaa   540
aacggtctgg tgccgattgt tgagccggaa gttatcccgg acggcgatca cgacctggag   600
cactgccagt atgtgaccga aaaggttctg gcggcggtgt acaaagcgct gaacgatcac   660
cacgtttatc tggagggtac cctgctgaaa ccgaacatgg tgaccgcggg ccatgcgtgc   720
accaagaaat acaccccgga acaggtggcg atggcgaccg tgaccgcgct gcaccgtacc   780
gttccggcgg cggtgccggg tatttgcttt ctgagcggtg gcatgagcga agaggacgcg   840
accctgaacc tgaacgcgat caacctgtgc ccgctgccga agccgtggaa actgagcttc   900
agctacggcc gtgcgctgca ggcgagcgcg ctggcgcgt ggggtggcaa ggcggcgaac   960
aaagaggcga cccaagaagc gtttatgaag cgtgcgatgg cgaactgcca ggcggcgaaa  1020
ggtcaatatg tgcataccgg cagcagcggt gcggcgagca cccagagcct gtttaccgcg  1080
tgctatacct attaa                                                   1095
```

<210> SEQ ID NO 51
<211> LENGTH: 364
<212> TYPE: PRT
<213> ORGANISM: Homo sapiens

<400> SEQUENCE: 51

```
Met Ala His Arg Phe Pro Ala Leu Thr Gln Glu Gln Lys Lys Glu Leu
1               5                   10                  15

Ser Glu Ile Ala Gln Ser Ile Val Ala Asn Gly Lys Gly Ile Leu Ala
            20                  25                  30

Ala Asp Glu Ser Val Gly Thr Met Gly Asn Arg Leu Gln Arg Ile Lys
        35                  40                  45

Val Glu Asn Thr Glu Glu Asn Arg Arg Gln Phe Arg Glu Ile Leu Phe
    50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
```

```
            100                 105                 110
Gly Ala Pro Leu Ala Gly Thr Asn Lys Glu Thr Thr Ile Gln Gly Leu
            115                 120                 125

Asp Gly Leu Ser Glu Arg Cys Ala Gln Tyr Lys Lys Asp Gly Val Asp
            130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
            165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
            195                 200                 205

Val Leu Ala Ala Val Tyr Lys Ala Leu Asn Asp His His Val Tyr Leu
            210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
            245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
            275                 280                 285

Leu Cys Pro Leu Pro Lys Pro Trp Lys Leu Ser Phe Ser Tyr Gly Arg
            290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
            325                 330                 335

Gln Ala Ala Lys Gly Gln Tyr Val His Thr Gly Ser Ser Gly Ala Ala
            340                 345                 350

Ser Thr Gln Ser Leu Phe Thr Ala Cys Tyr Thr Tyr
            355                 360

<210> SEQ ID NO 52
<211> LENGTH: 1149
<212> TYPE: DNA
<213> ORGANISM: Escherichia coli

<400> SEQUENCE: 52
atggctaaca gaatgattct gaacgaaacg gcatggtttg gtcggggtgc tgttggggct    60
ttaaccgatg aggtgaaacg ccgtggttat cagaaggcgc tgatcgtcac cgataaaacg   120
ctggtgcaat gcggcgtggt ggcgaaagtg accgataaga tggatgctgc agggctggca   180
tgggcgattt acgacggcgt agtgcccaac ccaacaatta ctgtcgtcaa gaagggctc    240 ggtgtattcc agaatagcgg cgcggattac ctgatcgcta ttggtggtgg ttctccacag   300
gatacttgta aagcgattgg cattatcagc aacaacccgg agtttgccga tgtgcgtagc   360
ctggaagggc tttcccccgac caataaaccc agtgtaccga ttctggcaat tcctaccaca   420
gcaggtactg cggcagaagt gaccattaac tacgtgatca ctgacgaaga gaacggcgc    480 aagtttgttt gcgttgatcc gcatgatatc ccgcaggtgg cgtttattga cgctgacatg   540
atggatggta tgcctccagc gctgaaagct gcgacgggtg tcgatgcgct cactcatgct   600
attgaggggt atattacccg tggcgcgtgg gcgctaaccg atgcactgca cattaaagcg   660
```

```
attgaaatca ttgctggggc gctgcgagga tcggttgctg gtgataagga tgccggagaa      720
gaaatggcgc tcgggcagta tgttgcgggt atgggcttct cgaatgttgg gttaggttg       780 gtgcatggta tggcgcatcc actgggcgcg ttttataaca ctccacacgg tgttgcgaac      840
gccatcctgt taccgcatgt catgcgttat aacgctgact ttaccggtga agtaccgc        900 gatatcgcgc gcgttatggg cgtgaaagtg aaggtatga gcctggaaga ggcgcgtaat       960
gccgctgttg aagcggtgtt tgctctcaac cgtgatgtcg gtattccgcc acatttgcgt     1020
gatgttggtg tacgcaagga agacattccg gcactggcgc aggcggcact ggatgatgtt    1080
tgtaccggtg caacccgcg tgaagcaacg cttgaggata ttgtagagct ttaccatacc     1140
gcctggtaa                                                             1149
```

<210> SEQ ID NO 53  
<211> LENGTH: 144  
<212> TYPE: DNA  
<213> ORGANISM: Artificial Sequence  
<220> FEATURE:  
<223> OTHER INFORMATION: proD promoter

<400> SEQUENCE: 53

```
cacagctaac accacgtcgt ccctatctgc tgccctaggt ctatgagtgg ttgctggata       60
actttacggg catgcataag gctcgtataa tatattcagg gagtccacaa cggtttccct     120
ctacaaataa ttttgtttaa cttt                                            144
```

<210> SEQ ID NO 54  
<211> LENGTH: 870  
<212> TYPE: DNA  
<213> ORGANISM: Caulobacter crescentus

<400> SEQUENCE: 54

```
atgacggcgc aagttacttg tgtgtgggac ctgaaagcca cattaggaga aggcccgatc       60
tggcatggtg atacattatg gtttgtcgat attaaacagc gtaaaatcca taactaccat     120
ccggccactg gggagcgctt cagcttcgac gcaccggacc aggtgacgtt ccttgcgccc     180
atcgtcggtg cgactggatt tgtcgtagga ttaaagacgg gcatccaccg tttccatcca     240
gcaacaggtt tttccctgtt gcttgaggta gaggacgccg cttttgaataa tcgtccgaac    300 gatgcgaccg tggatgcaca aggacgtttg tggtttggta cgatgcacga tggtgaagag    360
aataacagcg gctctttgta tcgtatggat ttgacgggag ttgcacgcat ggatcgtgat    420
atttgcatca caaacggacc gtgcgtttcc cctgacggta aaaccttcta tcatacggac    480
acgctggaaa agaccattta cgcgttcgat cttgcggaag acggtcttct gagcaataaa    540
cgcgtgtttg ttcaattcgc tctgggtgac gatgtctacc ctgacggctc tgtggtagat    600
agcgaaggtt atctgtggac cgcactgtgg ggagggtttg gcgcggtgcg tttcagcccg    660
cagggtgacg ctgtaacccg cattgaatta ccggctccga acgtgacgaa gccgtgcttt    720
gggggtccgg atctgaaaac gttgtatttc accaccgcgc gtaaaggatt atcagatgag    780
acccttgccc aatatccatt ggctggcggg gttttcgccg taccggtaga tgtcgctggt    840
caacctcaac acgaagtgcg tttagtttaa                                      870
```

<210> SEQ ID NO 55  
<211> LENGTH: 289  
<212> TYPE: PRT  
<213> ORGANISM: Caulobacter crescentus

<400> SEQUENCE: 55

Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
            20                  25                  30

Gln Arg Lys Ile His Asn Tyr His Pro Ala Thr Gly Glu Arg Phe Ser
        35                  40                  45

Phe Asp Ala Pro Asp Gln Val Thr Phe Leu Ala Pro Ile Val Gly Ala
    50                  55                  60

Thr Gly Phe Val Val Gly Leu Lys Thr Gly Ile His Arg Phe His Pro
65                  70                  75                  80

Ala Thr Gly Phe Ser Leu Leu Leu Glu Val Glu Asp Ala Ala Leu Asn
                85                  90                  95

Asn Arg Pro Asn Asp Ala Thr Val Asp Ala Gln Gly Arg Leu Trp Phe
            100                 105                 110

Gly Thr Met His Asp Gly Glu Glu Asn Asn Ser Gly Ser Leu Tyr Arg
        115                 120                 125

Met Asp Leu Thr Gly Val Ala Arg Met Asp Arg Asp Ile Cys Ile Thr
    130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                165                 170                 175

Leu Ser Asn Lys Arg Val Phe Val Gln Phe Ala Leu Gly Asp Asp Val
            180                 185                 190

Tyr Pro Asp Gly Ser Val Val Asp Ser Glu Gly Tyr Leu Trp Thr Ala
        195                 200                 205

Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Thr Ala Arg Lys Gly
                245                 250                 255

Leu Ser Asp Glu Thr Leu Ala Gln Tyr Pro Leu Ala Gly Gly Val Phe
            260                 265                 270

Ala Val Pro Val Asp Val Ala Gly Gln Pro Gln His Glu Val Arg Leu
        275                 280                 285

Val

<210> SEQ ID NO 56
<211> LENGTH: 885
<212> TYPE: DNA
<213> ORGANISM: Burkholderia xenovorans

<400> SEQUENCE: 56
atgaaaatcc ccctccggt ctgtgtctgg ccagttcacg cggagttggg ggaaggccct      60
ttgtggcagg cggggaaaa cgcggtttat ttcgtggata ttaagggtcg tcaaattcac     120
cgtttaactg tgaccactgg ccaaacgcaa acctggaaag cgcctggaca gccaggggttt    180 attgccccat ggccggtca tgggtttgtt tgtggtctgc cgggaggtct ttaccgcttt     240
gacgccgggt caggccaatt cagcaagctg aaagatgtag aagtacatct tccggggaat    300
cgcttaaacg acggcttcgt cgatgccagc gggcatttat ggtttggatc tatggatgat    360
ggagaagaac agcctagtgg aaccctgtac cgtgtcaatc atgcgggaga ggctgttgcc    420

```
caggatgacg gatatgtcat cacgaatggt cctgcaagtt caccggatgc ccgcacttta    480
tatcacggcg acactatgcg tcgcgttgtc tacgctttcg acctgggcga agatgggaca    540
cttagccgca agcgcatctt tgccgcgatc tcgggagatg gctatccaga tggcatggcc    600
gtggacgcgg acggattcct gtgggttgcg ctgttcggtg gatggcgtat tgaacgtttc    660
tccccggacg gaaaacgtgt cgagcaagtt ccgtttcctt gcgctaacgt gacgaaattg    720
gcattcggcg gcgacgattt acaaacggtc tatgcgtcaa ccgcctggaa gggtttgtct    780
cccgttgcgc gtcagcaaca gcccgacgca gggggttat tcagctttcg ctccccggta    840
ccaggccagc cccaggcccg ttgcaaatgg ggcttcgctc agtaa                    885
```

<210> SEQ ID NO 57
<211> LENGTH: 294
<212> TYPE: PRT
<213> ORGANISM: Burkholderia xenovorans

<400> SEQUENCE: 57

```
Met Lys Ile His Pro Val Cys Val Trp Pro Val His Ala Glu Leu
1               5                   10                  15

Gly Glu Gly Pro Leu Trp Gln Ala Gly Glu Asn Ala Val Tyr Phe Val
            20                  25                  30

Asp Ile Lys Gly Arg Gln Ile His Arg Leu Thr Val Thr Thr Gly Gln
        35                  40                  45

Thr Gln Thr Trp Lys Ala Pro Gly Gln Pro Gly Phe Ile Ala Pro Leu
    50                  55                  60

Ala Gly His Gly Phe Val Cys Gly Leu Pro Gly Leu Tyr Arg Phe
65                  70                  75                  80

Asp Ala Gly Ser Gly Gln Phe Ser Lys Leu Lys Asp Val Glu Val His
                85                  90                  95

Leu Pro Gly Asn Arg Leu Asn Asp Gly Phe Val Asp Ala Ser Gly His
            100                 105                 110

Leu Trp Phe Gly Ser Met Asp Asp Gly Glu Glu Gln Pro Ser Gly Thr
        115                 120                 125

Leu Tyr Arg Val Asn His Ala Gly Glu Ala Val Ala Gln Asp Asp Gly
    130                 135                 140

Tyr Val Ile Thr Asn Gly Pro Ala Ser Ser Pro Asp Ala Arg Thr Leu
145                 150                 155                 160

Tyr His Gly Asp Thr Met Arg Arg Val Val Tyr Ala Phe Asp Leu Gly
                165                 170                 175

Glu Asp Gly Thr Leu Ser Arg Lys Arg Ile Phe Ala Ala Ile Ser Gly
            180                 185                 190

Asp Gly Tyr Pro Asp Gly Met Ala Val Asp Ala Asp Gly Phe Leu Trp
        195                 200                 205

Val Ala Leu Phe Gly Gly Trp Arg Ile Glu Arg Phe Ser Pro Asp Gly
    210                 215                 220

Lys Arg Val Glu Gln Val Pro Phe Pro Cys Ala Asn Val Thr Lys Leu
225                 230                 235                 240

Ala Phe Gly Gly Asp Asp Leu Gln Thr Val Tyr Ala Ser Thr Ala Trp
                245                 250                 255

Lys Gly Leu Ser Pro Val Ala Arg Gln Gln Gln Pro Asp Ala Gly Gly
            260                 265                 270

Leu Phe Ser Phe Arg Ser Pro Val Pro Gly Gln Pro Gln Ala Arg Cys
        275                 280                 285
```

Lys Trp Gly Phe Ala Gln
                290

<210> SEQ ID NO 58
<211> LENGTH: 876
<212> TYPE: DNA
<213> ORGANISM: Haloferax volcanii

<400> SEQUENCE: 58

| | | | | | |
|---|---|---|---|---|---|
| atgaccgtca cgagagtggt cgacacgtcg tgccgactcg gcgagggacc ggtctggcac | | | | | 60 |
| cccgacgaga agcggctgta ctgggtagac atcgaatccg gcgactcca ccgctacgac | | | | | 120 |
| cccgagaccg gagcgcacga ctgtccggtc gaaacgtcgg tcatcgccgg cgtgacgata | | | | | 180 |
| cagcgcgacg ggtcgctcct agcgttcatg gaccgcggtc gcgtcgggcg cgtcgtcgac | | | | | 240 |
| ggcgaccgcc gggaaagcgc gcgaatcgtc gactcaccga cccggttcaa cgacgtcatc | | | | | 300 |
| gccgaccccg ccgggcgggt gttctgcggg acgatgccgt cagatacggc gggcgggcgg | | | | | 360 |
| ctgttccgcc tcgacaccga cggaacggtg acgacggtcg aaaccggcgt cggaatcccc | | | | | 420 |
| aacgggatgg gattcacccg cgaccgcgag cgattctact tcacggaaac cgaggcgcgc | | | | | 480 |
| accgtctatc ggtacgccta cgacgaagag acgggagccg tctcggcccg cgagcggttc | | | | | 540 |
| gtcgaatcgc cggagacgcc ggggctaccg gacgggatga cggtcgattc ggcggggcac | | | | | 600 |
| atctggtcgg cccgctggga gggcggctgt gtggtcgagt acgacgccga cggcaccgaa | | | | | 660 |
| ctcggccggt tcgacgtgcc gacggagaag gtgacgagcg tcgccttcgg cgggccggac | | | | | 720 |
| ctcgattcgc tctacgtgac gaccgccggc ggcgacgggg acgggagcgc tggcgagggc | | | | | 780 |
| gacgagagca ccggcgacgc tgcgggcgcg ctgttccgcc tcgacgtggc ggcgaccggg | | | | | 840 |
| cggcccgagt tccgctccga cgttcggttg gggtga | | | | | 876 |

<210> SEQ ID NO 59
<211> LENGTH: 291
<212> TYPE: PRT
<213> ORGANISM: Haloferax volcanii

<400> SEQUENCE: 59

Met Thr Val Thr Arg Val Val Asp Thr Ser Cys Arg Leu Gly Glu Gly
1               5                   10                  15

Pro Val Trp His Pro Asp Glu Lys Arg Leu Tyr Trp Val Asp Ile Glu
                20                  25                  30

Ser Gly Arg Leu His Arg Tyr Asp Pro Glu Thr Gly Ala His Asp Cys
            35                  40                  45

Pro Val Glu Thr Ser Val Ile Ala Gly Val Thr Ile Gln Arg Asp Gly
        50                  55                  60

Ser Leu Leu Ala Phe Met Asp Arg Gly Arg Val Gly Arg Val Val Asp
65                  70                  75                  80

Gly Asp Arg Arg Glu Ser Ala Arg Ile Val Asp Ser Pro Thr Arg Phe
                85                  90                  95

Asn Asp Val Ile Ala Asp Pro Ala Gly Arg Val Phe Cys Gly Thr Met
                100                 105                 110

Pro Ser Asp Thr Ala Gly Gly Arg Leu Phe Arg Leu Asp Thr Asp Gly
            115                 120                 125

Thr Val Thr Val Glu Thr Gly Val Gly Ile Pro Asn Gly Met Gly
        130                 135                 140

Phe Thr Arg Asp Arg Glu Arg Phe Tyr Phe Thr Glu Thr Glu Ala Arg
145                 150                 155                 160

Thr Val Tyr Arg Tyr Ala Tyr Asp Glu Glu Thr Gly Ala Val Ser Ala
            165                 170                 175

Arg Glu Arg Phe Val Glu Ser Pro Glu Thr Pro Gly Leu Pro Asp Gly
        180                 185                 190

Met Thr Val Asp Ser Ala Gly His Ile Trp Ser Ala Arg Trp Glu Gly
        195                 200                 205

Gly Cys Val Val Glu Tyr Asp Ala Asp Gly Thr Glu Leu Gly Arg Phe
        210                 215                 220

Asp Val Pro Thr Glu Lys Val Thr Ser Val Ala Phe Gly Gly Pro Asp
225                 230                 235                 240

Leu Asp Ser Leu Tyr Val Thr Thr Ala Gly Asp Gly Asp Gly Ser
            245                 250                 255

Ala Gly Glu Gly Asp Glu Ser Thr Gly Asp Ala Ala Gly Ala Leu Phe
        260                 265                 270

Arg Leu Asp Val Ala Ala Thr Gly Arg Pro Glu Phe Arg Ser Asp Val
        275                 280                 285

Arg Leu Gly
    290

<210> SEQ ID NO 60
<211> LENGTH: 1776
<212> TYPE: DNA
<213> ORGANISM: Caulobacter crescentus

<400> SEQUENCE: 60

| | | | | | |
|---|---|---|---|---|---|
| atgtcgaatc | gcactccacg | tcgttttcgc | tcacgtgact | ggttcgataa | tccagaccat | 60 |
| atcgacatga | cggccttgta | tcttgaacgt | tttatgaatt | atgggattac | ccccgaggag | 120 |
| ttacgctcgg | ggaagccgat | tattgggatc | gcacagactg | gctctgatat | tcaccctgt | 180 |
| aaccgtatcc | acctggacct | ggtgcagcgt | gtgcgtgacg | ggatccgtga | cgcaggaggc | 240 |
| attcctatgg | aattcccagt | tcacccaatc | ttcgagaatt | gccgtcgccc | tactgctgcg | 300 |
| cttgatcgta | accttttctta | cttgggtctt | gtcgagactc | ttcatgggta | ccctatcgat | 360 |
| gcggtcgttt | taacaacggg | gtgcgataaa | acgaccccag | caggcattat | ggctgccacc | 420 |
| acagtcaaca | tcccggctat | tgtgttgtcc | ggggggcccaa | tgcttgatgg | gtggcatgaa | 480 |
| aatgaattgg | tgggttcagg | cacagtcatt | tggcgtagcc | gtcgcaaatt | agccgccggc | 540 |
| gaaatcacag | aagaagaatt | tattgaccgt | gccgctagta | gcgcgccaag | cgcgggacac | 600 |
| tgtaacacga | tgggaacagc | gtccacgatg | aatgccgtgg | cggaggcttt | gggtcttcc | 660 |
| ctgacaggtt | gtgcagccat | tcccgcaccc | tatcgcgagc | gtggtcagat | ggcgtacaaa | 720 |
| acgggacaac | gcattgtgga | cttggcgtat | gacgacgtta | agccacttga | catccttacc | 780 |
| aagcaggcgt | tgaaaacgc | cattgctttg | gtcgccgcag | ccggaggttc | gaccaatgca | 840 |
| cagccacaca | ttgtagcaat | ggcccgccat | gccggagtgg | aaatcaccgc | cgatgattgg | 900 |
| cgtgctgcat | atgacattcc | gcttatcgtg | aatatgcaac | tgctggtaa | atacttggga | 960 |
| gaacgttcc | atcgcgctgg | tggcgcacca | gcggtactgt | gggagttact | tcagcaaggt | 1020 |
| cgcctgcacg | cgacgtact | tactgtcacg | ggaaagacaa | tgtcagagaa | cttacgggg | 1080 |
| cgcgaaacct | cagatcgtga | agtaatcttt | cctatcatg | aaccgcttgc | cgagaaagcc | 1140 |
| ggcttcttgg | ttcttaaggg | caatttgttt | gatttcgcga | tcatgaaaag | ctcggtgatt | 1200 |
| ggtgaggaat | tcgtaagcg | ctacttatca | cagccaggc | aagagggtgt | ttcgaagca | 1260 |
| cgtgctattg | tttttgacgg | ctcggacgac | taccataaac | gcattaacga | tcctgcatta | 1320 |

-continued

```
gaaatcgatg aacgttgtat cttagtgatc cgtggtgcag gaccaatcgg gtggccgggc    1380
tcagcggagg tcgtcaacat gcaaccacca gaccacttac tgaaaaaagg gatcatgtcg    1440
ttaccaacac tgggggacgg tcgtcaaagt ggtactgccg attcccctc tattttgaat    1500 gcgtccccag agtccgctat tggaggcgga cttagctggc ttcgtacagg tgacacaatc    1560
cgtatcgatc tgaacacggg acgttgcgac gcgttagtgg acgaggccac aattgcggct    1620
cgtaagcagg acggaattcc cgccgtcccg gcaaccatga caccgtggca agaaatttat    1680
cgcgcgcatg cgtcacagct tgacaccggt ggggtattgg agtttgctgt gaaatatcag    1740
gatctggcgg cgaagctgcc acgccataat cactaa                              1776
```

<210> SEQ ID NO 61
<211> LENGTH: 591
<212> TYPE: PRT
<213> ORGANISM: Caulobacter crescentus

<400> SEQUENCE: 61

```
Met Ser Asn Arg Thr Pro Arg Arg Phe Arg Ser Arg Asp Trp Phe Asp
 1               5                  10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Phe Ile Asp Arg Ala Ala
            180                 185                 190

Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
    210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Val Lys Pro Leu
                245                 250                 255

Asp Ile Leu Thr Lys Gln Ala Phe Glu Asn Ala Ile Ala Leu Val Ala
            260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
```

Asp Ile Pro Leu Ile Val Asn Met Gln Pro Ala Gly Lys Tyr Leu Gly
305                 310                 315                 320

Glu Arg Phe His Arg Ala Gly Ala Pro Ala Val Leu Trp Glu Leu
            325                 330                 335

Leu Gln Gln Gly Arg Leu His Gly Asp Val Leu Thr Val Thr Gly Lys
                340                 345                 350

Thr Met Ser Glu Asn Leu Gln Gly Arg Glu Thr Ser Asp Arg Glu Val
            355                 360                 365

Ile Phe Pro Tyr His Glu Pro Leu Ala Glu Lys Ala Gly Phe Leu Val
370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Asp Tyr His
            420                 425                 430

Lys Arg Ile Asn Asp Pro Ala Leu Glu Ile Asp Glu Arg Cys Ile Leu
            435                 440                 445

Val Ile Arg Gly Ala Gly Pro Ile Gly Trp Pro Gly Ser Ala Glu Val
    450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Leu Ser
            500                 505                 510

Trp Leu Arg Thr Gly Asp Thr Ile Arg Ile Asp Leu Asn Thr Gly Arg
                515                 520                 525

Cys Asp Ala Leu Val Asp Glu Ala Thr Ile Ala Ala Arg Lys Gln Asp
    530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Val Leu Glu Phe Ala
            565                 570                 575

Val Lys Tyr Gln Asp Leu Ala Ala Lys Leu Pro Arg His Asn His
            580                 585                 590

<210> SEQ ID NO 62
<211> LENGTH: 1785
<212> TYPE: DNA
<213> ORGANISM: Burkholderia xenovorans

<400> SEQUENCE: 62
atgtcagcca gtacccctcg tcgtcttcgc tctcaggagt ggttcgacga tccgagtcac    60
gctgatatga ccgcattata tgtcgagcgt tttatgaact atggattaac tcgcgaggaa    120
ttacaatctg gtcgtccgat tatcggcatt gcacagaccg gaagcgacct ggcgccctgt    180
aatcgccacc atatcgagtt agcccgcgcg acaaaggccg gaattcgcga cgcgggtgga    240
attccaatgg agttccccgt ccatccgctt gccgaacaat cccgccgccc gacggccgcg    300
cttgaccgta atctggctta cttgggtctg gtggaaatct tacacggttt cccttagat     360 ggcgtagttt taaccactgg ttgcgataaa accacgccag cgtgtctgat ggcagctgcg    420
acagtggata tgccagcgat cgtgttaagt ggcggccccca tgcttgatgg atggcacgag    480

```
ggtaaacgcg tgggctctgg tacagtcatt tggcatgcgc gcaacctgtt ggcgacaggg      540
gagattgatt acgaagggtt catgcagttg actacggcgc gagtccatc tatcggccac       600 tgtaatacta tggggacagc gttatccatg aactcattgg cagaggcgct gggtatgagc      660
ttacccggtt gtgcttcaat tcccgctgca tatcgtgaac gtggccagat ggcgtacgcg      720
acaggcaagc gtattgtgga cttggtccgc gaagatgtcc gtccaagcca tatcatgact      780
aaggcggcat ttgaaaatgc catcgtcgtt gcaagcgccc ttggcgcgag cacaaattgt      840
ccaccacatt taattgctat tgcgcgccat atgggggtgg aattgacttt agatgattgg      900
caacgcgtgg gtgagcaggt gccccttatt gtaaactgca tgcccgctgg cgaatatttg      960
ggtgaatcgt ttcatcgtgc tgggggtgtt ccagctgtct tgcgcgagtt ggtccacgct     1020
caactggttc atcgcgagtg tctgactgtc agtggccgca ctattggaga gatcgcggcg     1080
gatgccccat cgccagatcg tgacgtgatt cgcactactg aagacccgct taaacatggg     1140
gcgggattta tcgtattgtc aggcaacttt ttcgatagtg caattatgaa gatgagtgtg     1200
gtaggcgaag cctttcgtca aacgtacctg tccgagcctg gcaacgagaa cacatttgaa     1260
gctcgtgcca tcgttttga cggcccagaa gattaccacg cgcgtatcaa tgaccctagc      1320
cttgatattg accaacattg tattttagtc attcgtggag ccggtaccgt aggatatccg     1380
ggcagtgctg aggtagtgaa catggccccg ccggcggaat tagtgcgtca gggtatcacc     1440
tcattgccaa cacttggaga tggccgtcaa agcggcacat cagcttcgcc gtctattttg     1500
aacatgagcc ctgaggccgc cgttggcgga ggattaagtc ttttgcgcac caatgaccgc     1560
attcgtgttg atctgaactc acgctcagta aatgtactgg ttgatgacga agaattagca     1620
cgccgtcgtg aaaccgcaac gttcgctatt cctcctaccc agacgccgtg gcaagaatta     1680
taccgccaga cggtggggca gctgagtact ggcgggtgtc tggaacctgc taccttatat     1740
ttgaaagtta tcgcagaacg tggcaatccg cgtcacagcc actaa                      1785
```

<210> SEQ ID NO 63
<211> LENGTH: 594
<212> TYPE: PRT
<213> ORGANISM: Burkholderia xenovorans

<400> SEQUENCE: 63

```
Met Ser Ala Ser Thr Pro Arg Arg Leu Arg Ser Gln Glu Trp Phe Asp
1               5                   10                  15

Asp Pro Ser His Ala Asp Met Thr Ala Leu Tyr Val Glu Arg Phe Met
            20                  25                  30

Asn Tyr Gly Leu Thr Arg Glu Glu Leu Gln Ser Gly Arg Pro Ile Ile
        35                  40                  45

Gly Ile Ala Gln Thr Gly Ser Asp Leu Ala Pro Cys Asn Arg His His
    50                  55                  60

Ile Glu Leu Ala Ala Arg Thr Lys Ala Gly Ile Arg Asp Ala Gly Gly
65                  70                  75                  80

Ile Pro Met Glu Phe Pro Val His Pro Leu Ala Glu Gln Ser Arg Arg
                85                  90                  95

Pro Thr Ala Ala Leu Asp Arg Asn Leu Ala Tyr Leu Gly Leu Val Glu
            100                 105                 110

Ile Leu His Gly Phe Pro Leu Asp Gly Val Val Leu Thr Thr Gly Cys
        115                 120                 125

Asp Lys Thr Thr Pro Ala Cys Leu Met Ala Ala Thr Val Asp Met
    130                 135                 140
```

```
Pro Ala Ile Val Leu Ser Gly Gly Pro Met Leu Asp Gly Trp His Glu
145                 150                 155                 160

Gly Lys Arg Val Gly Ser Gly Thr Val Ile Trp His Ala Arg Asn Leu
                165                 170                 175

Leu Ala Thr Gly Glu Ile Asp Tyr Glu Gly Phe Met Gln Leu Thr Thr
            180                 185                 190

Ala Ser Ser Pro Ser Ile Gly His Cys Asn Thr Met Gly Thr Ala Leu
            195                 200                 205

Ser Met Asn Ser Leu Ala Glu Ala Leu Gly Met Ser Leu Pro Gly Cys
        210                 215                 220

Ala Ser Ile Pro Ala Ala Tyr Arg Glu Arg Gly Gln Met Ala Tyr Ala
225                 230                 235                 240

Thr Gly Lys Arg Ile Val Asp Leu Val Arg Glu Asp Val Arg Pro Ser
                245                 250                 255

His Ile Met Thr Lys Ala Ala Phe Glu Asn Ala Ile Val Val Ala Ser
            260                 265                 270

Ala Leu Gly Ala Ser Thr Asn Cys Pro Pro His Leu Ile Ala Ile Ala
        275                 280                 285

Arg His Met Gly Val Glu Leu Thr Leu Asp Asp Trp Gln Arg Val Gly
        290                 295                 300

Glu Gln Val Pro Leu Ile Val Asn Cys Met Pro Ala Gly Glu Tyr Leu
305                 310                 315                 320

Gly Glu Ser Phe His Arg Ala Gly Val Pro Ala Val Leu Arg Glu
                325                 330                 335

Leu Val His Ala Gln Leu Val His Arg Glu Cys Leu Thr Val Ser Gly
            340                 345                 350

Arg Thr Ile Gly Glu Ile Ala Ala Asp Ala Pro Ser Pro Asp Arg Asp
            355                 360                 365

Val Ile Arg Thr Thr Glu Asp Pro Leu Lys His Gly Ala Gly Phe Ile
370                 375                 380

Val Leu Ser Gly Asn Phe Phe Asp Ser Ala Ile Met Lys Met Ser Val
385                 390                 395                 400

Val Gly Glu Ala Phe Arg Gln Thr Tyr Leu Ser Glu Pro Gly Asn Glu
                405                 410                 415

Asn Thr Phe Glu Ala Arg Ala Ile Val Phe Asp Gly Pro Glu Asp Tyr
            420                 425                 430

His Ala Arg Ile Asn Asp Pro Ser Leu Asp Ile Asp Gln His Cys Ile
            435                 440                 445

Leu Val Ile Arg Gly Ala Gly Thr Val Gly Tyr Pro Gly Ser Ala Glu
        450                 455                 460

Val Val Asn Met Ala Pro Pro Ala Glu Leu Val Arg Gln Gly Ile Thr
465                 470                 475                 480

Ser Leu Pro Thr Leu Gly Asp Gly Arg Gln Ser Gly Thr Ser Ala Ser
            485                 490                 495

Pro Ser Ile Leu Asn Met Ser Pro Glu Ala Ala Val Gly Gly Gly Leu
            500                 505                 510

Ser Leu Leu Arg Thr Asn Asp Arg Ile Arg Val Asp Leu Asn Ser Arg
        515                 520                 525

Ser Val Asn Val Leu Val Asp Asp Glu Glu Leu Ala Arg Arg Arg Glu
        530                 535                 540

Thr Ala Thr Phe Ala Ile Pro Pro Thr Gln Thr Pro Trp Gln Glu Leu
545                 550                 555                 560
```

Tyr Arg Gln Thr Val Gly Gln Leu Ser Thr Gly Gly Cys Leu Glu Pro
            565                 570                 575

Ala Thr Leu Tyr Leu Lys Val Ile Ala Glu Arg Gly Asn Pro Arg His
            580                 585                 590

Ser His

<210> SEQ ID NO 64
<211> LENGTH: 1239
<212> TYPE: DNA
<213> ORGANISM: Haloferax volcanii

<400> SEQUENCE: 64

| | |
|---|---|
| atggttgagc aagcgaagct tagcgacccg aacgcggagt acacgatgcg cgacctgtcc | 60 |
| gcggagacga tagacatcac gaatccgcga ggtggcgtcc gcgacgccga aatcacggac | 120 |
| gtacagacga cgatggtcga cgggaactac ccgtggattc tcgtccgcgt ctacaccgac | 180 |
| gcgggcgtcg tcggcaccgg cgaggcctac tggggcggcg gcgacaccgc catcatcgag | 240 |
| cggatgaagc cgttcctcgt cggcgagaac cccctcgaca tcgaccgcct gtacgagcat | 300 |
| ctcgtccaga gatgtccgg cgagggctcc gtctcgggca aggtcatctc cgccatctcg | 360 |
| ggcatcgaaa tcgcgctcca cgacgtcgcc ggaaagctcc tcgacgtgcc cgcctatcaa | 420 |
| ctcgtcggcg ggaagtaccg cgacgaggtg cgcgtctact gcgacctcca caccgaagac | 480 |
| gaggccaacc cgcaggcctg cgccgaggag gcgtccgcg tggtcgagga actcggctac | 540 |
| gacgccatca gttcgacct cgacgtgccc tcgggccacg agaaggaccg cgcgaaccgc | 600 |
| cacctccgaa accccgaaat cgaccacaag gtcgaaatcg tcgaggccgt caccgaggcc | 660 |
| gtcggcgacc gcgcggacgt ggcgttcgac tgccactggt cctttaccgg cgggagcgcc | 720 |
| aagcgcctcg cgtccgagct ggaagactac gacgtgtggt ggctcgaaga ccccgtgccg | 780 |
| ccggagaacc acgacgtgca gaagctcgtg acgcagtcca cgacgacgcc catcgcggtc | 840 |
| ggtgagaacg tctaccggaa gttcggccag cggacgctgc tcgaaccgca ggcggtggat | 900 |
| atcatcgcgc ccgacctgcc ccgcgtcggc ggcatgcgcg agacgcggaa gattgccgac | 960 |
| ctcgcggaca tgtactacat ccccgtggcg atgcacaacg tctcgtcgcc catcgggacg | 1020 |
| atggcctccg cgcaggtcgc cgcggccatc ccgaactcgc tggccctcga ataccactcc | 1080 |
| taccagctcg gctggtggga ggacctcgtc gaagaggacg acctgattca gaacggtcac | 1140 |
| atggagattc ccgaaaagcc cggcctcggg ctgacgctcg acctcgacgc cgtcgaagca | 1200 |
| cacatggtcg aaggggagac gctcttcgac gaggagtaa | 1239 |

<210> SEQ ID NO 65
<211> LENGTH: 412
<212> TYPE: PRT
<213> ORGANISM: Haloferax volcanii

<400> SEQUENCE: 65

Met Val Glu Gln Ala Lys Leu Ser Asp Pro Asn Ala Glu Tyr Thr Met
1               5                   10                  15

Arg Asp Leu Ser Ala Glu Thr Ile Asp Ile Thr Asn Pro Arg Gly Gly
            20                  25                  30

Val Arg Asp Ala Glu Ile Thr Asp Val Gln Thr Thr Met Val Asp Gly
        35                  40                  45

Asn Tyr Pro Trp Ile Leu Val Arg Val Tyr Thr Asp Ala Gly Val Val
    50                  55                  60

Gly Thr Gly Glu Ala Tyr Trp Gly Gly Gly Asp Thr Ala Ile Ile Glu

```
65                  70                  75                  80

Arg Met Lys Pro Phe Leu Val Gly Glu Asn Pro Leu Asp Ile Asp Arg
                85                  90                  95

Leu Tyr Glu His Leu Val Gln Lys Met Ser Gly Glu Gly Ser Val Ser
            100                 105                 110

Gly Lys Val Ile Ser Ala Ile Ser Gly Ile Glu Ile Ala Leu His Asp
        115                 120                 125

Val Ala Gly Lys Leu Leu Asp Val Pro Ala Tyr Gln Leu Val Gly Gly
    130                 135                 140

Lys Tyr Arg Asp Glu Val Arg Val Tyr Cys Asp Leu His Thr Glu Asp
145                 150                 155                 160

Glu Ala Asn Pro Gln Ala Cys Ala Glu Glu Gly Val Arg Val Val Glu
                165                 170                 175

Glu Leu Gly Tyr Asp Ala Ile Lys Phe Asp Leu Asp Val Pro Ser Gly
            180                 185                 190

His Glu Lys Asp Arg Ala Asn Arg His Leu Arg Asn Pro Glu Ile Asp
        195                 200                 205

His Lys Val Glu Ile Val Glu Ala Val Thr Glu Ala Val Gly Asp Arg
    210                 215                 220

Ala Asp Val Ala Phe Asp Cys His Trp Ser Phe Thr Gly Gly Ser Ala
225                 230                 235                 240

Lys Arg Leu Ala Ser Glu Leu Glu Asp Tyr Asp Val Trp Trp Leu Glu
                245                 250                 255

Asp Pro Val Pro Pro Glu Asn His Asp Val Gln Lys Leu Val Thr Gln
            260                 265                 270

Ser Thr Thr Thr Pro Ile Ala Val Gly Glu Asn Val Tyr Arg Lys Phe
        275                 280                 285

Gly Gln Arg Thr Leu Leu Glu Pro Gln Ala Val Asp Ile Ile Ala Pro
    290                 295                 300

Asp Leu Pro Arg Val Gly Gly Met Arg Glu Thr Arg Lys Ile Ala Asp
305                 310                 315                 320

Leu Ala Asp Met Tyr Tyr Ile Pro Val Ala Met His Asn Val Ser Ser
                325                 330                 335

Pro Ile Gly Thr Met Ala Ser Ala Gln Val Ala Ala Ala Ile Pro Asn
            340                 345                 350

Ser Leu Ala Leu Glu Tyr His Ser Tyr Gln Leu Gly Trp Trp Glu Asp
        355                 360                 365

Leu Val Glu Glu Asp Asp Leu Ile Gln Asn Gly His Met Glu Ile Pro
    370                 375                 380

Glu Lys Pro Gly Leu Gly Leu Thr Leu Asp Leu Asp Ala Val Glu Ala
385                 390                 395                 400

His Met Val Glu Gly Glu Thr Leu Phe Asp Glu Glu
                405                 410

<210> SEQ ID NO 66
<211> LENGTH: 1179
<212> TYPE: DNA
<213> ORGANISM: Clostridium beijerinckii

<400> SEQUENCE: 66
atgaaagaag ttgttattgc gagcgcggtt cgtaccgcga ttggcagcta tggcaagagc      60
ctgaaggatg ttccggcggt ggacctgggt gcgaccgcga tcaaagaggc ggttaagaaa     120
gcgggcatta aaccggagga tgtgaacgaa gttatcctgg gtaacgtgct gcaagcgggt     180
```

```
ctgggccaaa acccggcgcg tcaggcgagc ttcaaggcgg gcctgccggt tgaaatcccg    240
gcgatgacca ttaacaaagt ttgcggtagc ggcctgcgta ccgtgagcct ggcggcgcaa    300
atcattaagg cgggtgacgc ggatgttatc attgcgggtg gcatggagaa catgagccgt    360
gcgccgtacc tggcgaacaa cgcgcgttgg ggttatcgta tgggcaacgc gaaattcgtg    420
gacgaaatga ttaccgacgg tctgtgggat gcgtttaacg actaccacat gggcatcacc    480
gcggagaaca ttgcggaacg ttggaacatt agccgtgagg aacaagatga gttcgcgctg    540
gcgagccaga agaaagcgga ggaagcgatc aagagcggcc agtttaaaga cgaaatcgtt    600
ccggtggtta ttaagggtcg taaggtgaa accgtggtgg acaccgatga cacccgcgt    660
ttcggtagca ccattgaggg cctggcgaag ctgaaaccgg cgtttaagaa agatggcacc    720
gtgaccgcgg gtaacgcgag cggcctgaac gactgcgcgg cggtgctggt tatcatgagc    780
gcggagaagg cgaaagaact gggtgtgaag ccgctggcga aaattgttag ctacggtagc    840
gcgggtgtgg acccggcgat catgggttac ggcccgtttt atgcgaccaa ggcggcgatt    900
gagaaagcgg gttggaccgt ggacgaactg gatctgatcg agagcaacga agcgttcgcg    960
gcgcaaagcc tggcggtggc gaaggatctg aaatttgaca tgaacaaggt gaacgtgaac    1020
ggtggtgcga ttgcgctggg tcacccgatt ggtgcgagcg gcgcgcgtat cctggtgacc    1080
ctggttcacg cgatgcagaa acgtgacgcg aagaaaggtc tggcgaccct gtgcattggt    1140
ggtggtcaag gcaccgcgat tctgctggaa aagtgctaa                          1179
```

<210> SEQ ID NO 67
<211> LENGTH: 393
<212> TYPE: PRT
<213> ORGANISM: Clostridium beijerinckii

<400> SEQUENCE: 67

```
Met Arg Asp Val Val Ile Val Ser Ala Val Arg Thr Ala Leu Gly Ser
  1               5                  10                  15

Phe Gly Gly Ala Leu Lys Asp Val Ser Ala Val Asp Leu Gly Ala Leu
             20                  25                  30

Val Ile Lys Glu Ala Val Asn Arg Ala Gly Val Lys Pro Glu Leu Ile
         35                  40                  45

Glu Glu Val Ile Met Gly Asn Val Ile Gln Ala Gly Leu Gly Gln Asn
     50                  55                  60

Thr Ala Arg Gln Ser Thr Ile Lys Ala Gly Leu Pro Gln Glu Val Ser
 65                  70                  75                  80

Ala Met Thr Ile Asn Lys Val Cys Gly Ser Gly Leu Arg Ala Val Ser
                 85                  90                  95

Leu Ala Ala Gln Met Ile Lys Ala Gly Asp Ala Asp Val Val Val Ala
            100                 105                 110

Gly Gly Met Glu Asn Met Ser Ala Ala Pro Tyr Ala Leu Asp Lys Ala
        115                 120                 125

Arg Trp Gly Gln Arg Met Gly Asp Gly Lys Leu Val Asp Thr Met Ile
    130                 135                 140

Lys Asp Ala Leu Trp Asp Ala Phe Asn Asn Tyr His Met Gly Val Thr
145                 150                 155                 160

Ala Glu Asn Ile Ala Lys Gln Trp Gly Leu Thr Arg Glu Glu Gln Asp
                165                 170                 175

Ala Phe Ser Ala Ser Ser Gln Gln Lys Ala Glu Ala Ala Ile Lys Ser
            180                 185                 190

Gly Arg Phe Lys Asp Glu Ile Val Pro Val Val Ile Pro Gln Arg Lys
```

```
                195                 200                 205
Gly Glu Pro Lys Val Phe Asp Thr Asp Glu Phe Pro Arg Phe Gly Thr
210                 215                 220

Thr Ala Glu Thr Leu Ala Lys Leu Lys Pro Ala Phe Ile Lys Asp Gly
225                 230                 235                 240

Thr Val Thr Ala Gly Asn Ala Ser Gly Ile Asn Asp Gly Ala Ala Ala
                245                 250                 255

Phe Val Val Met Ser Ala Glu Lys Ala Glu Glu Leu Gly Leu Lys Pro
            260                 265                 270

Met Ala Lys Ile Leu Ser Tyr Gly Ser Lys Gly Leu Asp Pro Ala Ile
        275                 280                 285

Met Gly Tyr Gly Pro Phe His Ala Thr Lys Lys Ala Leu Glu Lys Ala
    290                 295                 300

Asn Leu Thr Val Glu Asp Leu Asp Leu Ile Glu Ala Asn Glu Ala Phe
305                 310                 315                 320

Ala Ala Gln Ser Leu Ala Val Ala Lys Asp Leu Lys Phe Asp Met Ser
                325                 330                 335

Lys Val Asn Val Asn Gly Gly Ala Ile Ala Leu Gly His Pro Val Gly
            340                 345                 350

Ala Ser Gly Ala Arg Ile Leu Val Thr Leu Leu His Glu Met Glu Lys
        355                 360                 365

Arg Asp Ala Lys Lys Gly Leu Ala Thr Leu Cys Ile Gly Gly Met
    370                 375                 380

Gly Thr Ala Leu Ile Val Glu Arg Val
385                 390

<210> SEQ ID NO 68
<211> LENGTH: 1179
<212> TYPE: DNA
<213> ORGANISM: Clostridium acetobutylicum

<400> SEQUENCE: 68
atgaaagaag ttgtaatagc tagtgcagta agaacagcga ttggatctta tggaaagtct      60
cttaaggatg taccagcagt agatttagga gctacagcta taaggaagc agttaaaaaa    120 gcaggaataa aaccagagga tgttaatgaa gtcattttag gaatgttct tcaagcaggt    180 ttaggacaga atccagcaag acaggcatct tttaaagcag gattaccagt tgaaattcca    240
gctatgacta ttaataaggt ttgtggttca ggacttagaa cagttagctt agcagcacaa    300
attataaaag caggagatgc tgacgtaata atagcaggtg gtatggaaaa tatgtctaga    360
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaagctga agaagctata aaatcaggtc aatttaaaga tgaaatagtt    600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagttc ttatggttca    840 gcaggagttg acccagcaat aatgggatat ggaccttct atgcaacaaa agcagctatt    900 gaaaagcag ttggacagt tgatgaatta gatttaatag aatcaaatga agcttttgca    960
gctcaaagtt tagcagtagc aaaagattta aaatttgata tgaataaagt aaatgtaaat   1020
```

```
ggaggagcta ttgcccttgg tcatccaatt ggagcatcag gtgcaagaat actcgttact   1080
cttgtacacg caatgcaaaa aagagatgca aaaaaggct tagcaactttt atgtataggt    1140 ggcggacaag gaacagcaat attgctagaa aagtgctag                           1179
```

<210> SEQ ID NO 69
<211> LENGTH: 392
<212> TYPE: PRT
<213> ORGANISM: Clostridium acetobutylicum

<400> SEQUENCE: 69

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
```

```
              340             345             350
Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gln Gly
        370                 375             380

Thr Ala Ile Leu Leu Glu Lys Cys
385                 390

<210> SEQ ID NO 70
<211> LENGTH: 663
<212> TYPE: DNA
<213> ORGANISM: Escherichia coli

<400> SEQUENCE: 70
atgaaaacaa aattgatgac attacaagac gccaccggct tctttcgtga cggcatgacc    60
atcatggtgg gcggatttat ggggattggc actccatccc gcctggttga agcattactg   120
gaatctggtg ttcgcgacct gacattgata gccaatgata ccgcgtttgt tgataccggc   180
atcggtccgc tcatcgtcaa tggtcgagtc cgcaaagtga ttgcttcaca tatcggcacc   240
aacccggaaa caggtcggcg catgatatct ggtgagatgg acgtcgttct ggtgccgcaa   300
ggtacgctaa tcgagcaaat tcgctgtggt ggagctggac ttggtggttt tctcacccca   360
acgggtgtcg gcaccgtcgt agaggaaggc aaacagacac tgacactcga cggtaaaacc   420
tggctgctcg aacgcccact gcgcgccgac ctggcgctaa ttcgcgctca tcgttgcgac   480
acacttggca acctgaccta tcaacttagc gcccgcaact ttaacccccct gatagccctt   540
gcggctgata tcacgctggt agagccagat gaactggtcg aaaccggcga gctgcaacct   600
gaccatattg tcacccctgg tgccgttatc gaccacatca tcgtttcaca ggagagcaaa   660
taa                                                                 663

<210> SEQ ID NO 71
<211> LENGTH: 651
<212> TYPE: DNA
<213> ORGANISM: Escherichia coli

<400> SEQUENCE: 71
atggatgcga acaacgtat tgcgcgccgt gtggcgcaag agcttcgtga tggtgacatc     60
gttaacttag ggatcggttt acccacaatg gtcgccaatt atttaccgga gggtattcat   120
atcactctgc aatcggaaaa cggcttcctc ggtttaggcc cggtcacgac agcgcatcca   180
gatctggtga acgctggcgg gcaaccgtgc ggtgttttac ccggtgcagc catgtttgat   240
agcgccatgt catttgcgct aatccgtggc ggtcatattg atgcctgcgt gctcggcggt   300
ttgcaagtag acgaagaagc aaacctcgcg aactgggtag tgcctgggaa atggtgccc    360
ggtatgggtg gcgcgatgga tctggtgacc gggtcgcgca agtgatcat cgccatggaa    420
cattgcgcca agatggttc agcaaaaatt ttgcgccgct gcaccatgcc actcactgcg    480
caacatgcgg tgcatatgct ggttactgaa ctggctgtct ttcgttttat tgacggcaaa   540
atgtggctca ccgaaattgc cgacgggtgt gatttagcca ccgtgcgtgc caaaacagaa   600
gctcggtttg aagtcgccgc cgatctgaat acgcaacggg gtgatttatg a            651

<210> SEQ ID NO 72
<211> LENGTH: 220
<212> TYPE: PRT
<213> ORGANISM: Escherichia coli
```

```
<400> SEQUENCE: 72

Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220

<210> SEQ ID NO 73
<211> LENGTH: 216
<212> TYPE: PRT
<213> ORGANISM: Escherichia coli

<400> SEQUENCE: 73

Met Asp Ala Lys Gln Arg Ile Ala Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140
```

```
Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215
```

```
<210> SEQ ID NO 74
<211> LENGTH: 735
<212> TYPE: DNA
<213> ORGANISM: Clostridium acetobutylicum

<400> SEQUENCE: 74
atgctgaagg acgaggttat taagcagatt agcacccccgc tgaccagccc ggcgttcccg      60
cgtggtccgt acaagttcca taatcgcgaa tacttcaaca ttgtgtatcg taccgacatg     120
gatgcgctgc gtaaggtggt tccggagccg ctggaaattg acgagccgct ggttcgtttc     180
gaaatcatgg cgatgcacga taccagcggt ctgggctgct acaccgagag cggtcaggcg     240
attccggtga gctttaacgg tgttaaaggc gactacctgc acatgatgta tctggataac     300
gaaccggcga ttgcggtggg tcgtgagctg agcgcgtacc cgaagaaact gggctatccg     360
aagctgttcg tggacagcga taccctggtg ggcaccctgg actacggcaa actgcgtgtt     420
gcgaccgcga ccatgggcta taagcacaaa gcgctggacg cgaacgaagc gaaggatcag     480
atttgccgtc cgaactacat gctgaaaatc attccgaact atgacggtag cccgcgtatc     540
tgcgaactga ttaacgcgaa gatcaccgat gttaccgttc atgaggcgtg gaccggcccg     600
acccgtctgc aactgtttga ccacgcgatg gcgccgctga cgatctgcc ggtgaaagag     660
atcgttagca gcagccacat cctggcggac atcatcctgc cgcgtgcgga agttatctac     720
gattacctga agtaa                                                       735
```

```
<210> SEQ ID NO 75
<211> LENGTH: 244
<212> TYPE: PRT
<213> ORGANISM: Clostridium acetobutylicum

<400> SEQUENCE: 75

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
                20                  25                  30

Asn Ile Val Tyr Arg Thr Asp Met Asp Ala Leu Arg Lys Val Val Pro
            35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
```

```
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 76
<211> LENGTH: 741
<212> TYPE: DNA
<213> ORGANISM: Clostridium beijerinckii

<400> SEQUENCE: 76
atgctggaga gcgaagttag caaacaaatc accaccccgc tggcggcgcc ggcgttcccg      60
cgtggcccgt accgttttca taaccgtgag tacctgaaca tcatttatcg taccgacctg     120
gatgcgctgc gtaagattgt gccggagccg ctggaactgg accgtgcgta cgttcgtttc     180
gagatgatgg cgatgccgga taccaccggt ctgggcagct acaccgaatg cggtcaggcg     240
atcccggtga agtataacgg tgttaaaggc gactacctgc acatgatgta tctggataac     300
gagccggcga ttgcggtggg tcgtgaaagc agcgcgtacc cgaagaaact gggctatccg     360
aagctgtttg tggacagcga taccctggtg ggcaccctga aatatggcac cctgccggtt     420
gcgaccgcga ccatgggcta caagcacgag ccgctggacc tgaaagaagc gtatgcgcag     480
attgcgcgtc cgaacttcat gctgaagatc attcaaggtt atgacggcaa accgcgtatc     540
tgcgagctga tttgcgcgga aaacaccgat atcaccatcc atggtgcgtg gaccggcagc     600
gcgcgtctgc aactgtttag ccatgcgctg gcgccgctgg cggatctgcc ggtgctggaa     660
atcgttagcg cgagccacat tctgaccgat ctgaccctgg gcaccccgaa ggttgtgcat     720
gactatctga gcgtgaagta a                                               741

<210> SEQ ID NO 77
<211> LENGTH: 246
<212> TYPE: PRT
<213> ORGANISM: Clostridium beijerinckii

<400> SEQUENCE: 77

Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60
```

```
Met Pro Asp Thr Thr Gly Leu Gly Ser Tyr Thr Glu Cys Gly Gln Ala
 65                  70                  75                  80

Ile Pro Val Lys Tyr Asn Gly Val Lys Gly Asp Tyr Leu His Met Met
                 85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
            245

<210> SEQ ID NO 78
<211> LENGTH: 191
<212> TYPE: DNA
<213> ORGANISM: Artificial Sequence
<220> FEATURE:
<223> OTHER INFORMATION: OXB11 promoter

<400> SEQUENCE: 78
aagctgttgt gaccgcttgc tctagccagc tatcgagttg tgaaccgatc catctagcaa    60
ttggactcga tctagcgata ggcttcgatc tagctatgta gaaacgccgt gtgctcgatc   120
gcctgataag gtccacagta gctgctataa ttgcttcaac agaacatatt gactatccgg   180
tattacccgg c                                                        191

<210> SEQ ID NO 79
<211> LENGTH: 1500
<212> TYPE: DNA
<213> ORGANISM: Escherichia coli

<400> SEQUENCE: 79
atgagcatct tgtacgaaga gcgtcttgat ggcgctttac ccgatgtcga ccgcacatcg    60
gtactgatgg cactgcgtga gcatgtccct ggacttgaga tcctgcatac cgatgaggag   120
atcattcctt acgagtgtga cgggttgagc gcgtatcgca cgcgtccatt actggttgtt   180
ctgcctaagc aaatggaaca ggtgacagcg attctggctg tctgccatcg cctgcgtgta   240
ccggtggtga cccgtggtgc aggcaccggg ctttctggtg gcgcgctgcc gctgaaaaaa   300
ggtgtgttgt tggtgatggc gcgctttaaa gagatcctcg acattaaccc cgttggtcgc   360
cgcgcgcgcg tgcagccagg cgtgcgtaac ctggcgatct cccaggccgt tgcaccgcat   420
aatctctact acgcaccgga cccttcctca caaatcgcct gttccattgg cggcaatgtg   480
gctgaaaatg ccggcggcgt ccactgcctg aaatatggtc tgaccgtaca taacctgctg   540
```

-continued

```
aaaattgaag tgcaaacgct ggacggcgag gcactgacgc ttggatcgga cgcgctggat    600
tcacctggtt ttgacctgct ggcgctgttc accggatcgg aaggtatgct cggcgtgacc    660
accgaagtga cggtaaaact gctgccgaag ccgcccgtgg cgcgggttct gttagccagc    720
tttgactcgg tagaaaaagc cggacttgcg gttggtgaca tcatcgccaa tggcattatc    780
cccggcgggc tggagatgat ggataacctg tcgatccgcg cggcggaaga ttttattcat    840
gccggttatc ccgtcgacgc cgaagcgatt ttgttatgcg agctggacgg cgtggagtct    900
gacgtacagg aagactgcga gcgggttaac gacatcttgt tgaaagcggg cgcgactgac    960
gtccgtctgg cacaggacga agcagagcgc gtacgtttct gggccggtcg caaaaatgcg   1020 ttccggcgg taggacgtat ctccccggat tactactgca tggatggcac catcccgcgt   1080
cgcgccctgc ctggcgtact ggaaggcatt gcccgtttat cgcagcaata tgatttacgt   1140
gttgccaacg tctttcatgc cggagatggc aacatgcacc cgttaatcct tttcgatgcc   1200
aacgaacccg tgaatttgc ccgcgcgaa gagctgggcg gaagatcct cgaactctgc   1260 gttgaagttg gcggcagcat cagtggcgaa catggcatcg ggcgagaaaa aatcaatcaa   1320
atgtgcgccc agttcaacag cgatgaaatc acgaccttcc atgcggtcaa ggcggcgttt   1380
gaccccgatg gtttgctgaa ccctgggaaa acattccca cgctacaccg ctgtgctgaa   1440
tttggtgcca tgcatgtgca tcacggtcat ttacctttcc ctgaactgga gcgtttctga   1500
```

<210> SEQ ID NO 80
<211> LENGTH: 1053
<212> TYPE: DNA
<213> ORGANISM: Escherichia coli

<400> SEQUENCE: 80

```
atgctacgcg agtgtgatta cagccaggcg ctgctggagc aggtgaatca ggcgattagc     60
gataaaacgc cgctggtgat tcagggcagc aatagcaaag ccttttttagg tcgccctgtc    120 accgggcaaa cgctggatgt tcgttgtcat cgcggcattg ttaattacga cccgaccgag    180
ctggtgataa ccgcgcgtgt cggaacgccg ctggtgacaa ttgaagcggc gctggaaagc    240
gcggggcaaa tgctcccctg tgagccgccg cattatggtg aagaagccac ctggggcggg    300
atggtcgcct gcgggctggc ggggccgcgt cgcccgtgga gcggttcggt ccgcgatttt    360
gtcctcggca cgcgcatcat taccggcgct ggaaaacatc tgcgttttgg tggcgaagtg    420
atgaaaaacg ttgccggata cgatctctca cggttaatgg tcggaagcta cggttgtctt    480
ggcgtgctca ctgaaatctc aatgaaagtg ttaccgcgac cgcgcgcctc cctgagcctg    540
cgtcgggaaa tcagcctgca agaagccatg agtgaaatcg ccgagtggca actccagcca    600
ttacccatta gtggcttatg ttacttcgac aatgcgttgt ggatccgcct tgagggcggc    660
gaaggatcgg taaaagcagc gcgtgaactg ctgggtggcg aagaggttgc cggtcagttc    720
tggcagcaat tgcgtgaaca caactgccg ttcttctcgt taccaggtac cttatgcgc    780 atttcattac ccagtgatgc gccgatgatg gatttacccg gcgagcaact gatcgactgg    840
ggcggggcgt tacgctggct gaaatcgaca gccgaggaca tcaaatcca tcgcatcgcc    900 cgcaacgctg gcggtcatgc gacccgcttt agtgccggag atggtggctt tgccccgcta    960
tcggctcctt tattccgcta tcaccagcag cttaaacagc agctcgaccc ttgcggcgtg   1020
tttaaccccg gtcgcatgta cgcggaactt tga                                 1053
```

<210> SEQ ID NO 81

-continued

```
<211> LENGTH: 1224
<212> TYPE: DNA
<213> ORGANISM: Escherichia coli

<400> SEQUENCE: 81
atgcaaaccc aattaactga agagatgcgg cagaacgcgc gcgcgctgga agccgacagc    60
atcctgcgcg cctgtgttca ctgcggattt tgtaccgcaa cctgcccaac ctatcagctt   120
ctgggcgatg aactggacgg gccgcgcggg cgcatctatc tgattaaaca ggtgctggaa   180
ggcaacgaag tcacgcttaa aacacaggag catctcgatc gctgcctcac ttgccgtaat   240
tgtgaaacca cctgtccttc tggtgtgcgc tatcacaatt tgctggatat cgggcgtgat   300
attgtcgagc agaaagtgaa acgcccactg ccggagcgaa tactgcgcga aggattgcgc   360
caggtagtgc cgcgtccggc ggtcttccgt gcgctgacgc aggtagggct ggtgctgcga   420 ccgttttttac cggaacaggt cagagcaaaa ctgcctgctg aaacggtgaa agctaaaccg   480
cgtccgccgc tgcgccataa gcgtcgggtt ttaatgttgg aaggctgcgc ccagcctacg   540
ctttcgccca acaccaacgc ggcaactgcg cgagtgctgg atcgtctggg gatcagcgtc   600
atgccagcta acgaagcagg ctgttgtggc gcggtggact atcatcttaa tgcgcaggag   660
aaagggctgg cacgggcgcg caataatatt gatgcctggt ggcccgcgat gaagcaggt   720 gccgaggcaa ttttgcaaac cgccagcggc tgcggcgcgt ttgtcaaaga gtatgggcag   780
atgctgaaaa acgatgcgtt atatgccgat aaagcacgtc aggtcagtga actggcggtc   840
gatttagtcg aacttctgcg cgaggaaccg ctggaaaaac tggcaattcg cggcgataaa   900
aagctggcct ccactgtcc gtgtaccccta aacatgcgc aaaagctgaa cggcgaagtg   960
gaaaaagtgt tgcttcgtct tggatttacc ttaacggacg ttcccgacag ccatctgtgc  1020
tgcggttcag cgggaacata tgcgttaacg catcccgatc tggcacgcca gctgcgggat  1080
aacaaaatga atgcgctgga aagcggcaaa ccggaaatga tcgtcaccgc caacattggt  1140
tgccagacgc atctggcgag cgccggtcgt acctctgtgc gtcactggat gaaattgta  1200 gaacaagccc ttgaaaagga ataa                                         1224

<210> SEQ ID NO 82
<211> LENGTH: 499
<212> TYPE: PRT
<213> ORGANISM: Escherichia coli

<400> SEQUENCE: 82

Met Ser Ile Leu Tyr Glu Glu Arg Leu Asp Gly Ala Leu Pro Asp Val
1               5                   10                  15

Asp Arg Thr Ser Val Leu Met Ala Leu Arg Glu His Val Pro Gly Leu
                20                  25                  30

Glu Ile Leu His Thr Asp Glu Glu Ile Ile Pro Tyr Glu Cys Asp Gly
            35                  40                  45

Leu Ser Ala Tyr Arg Thr Arg Pro Leu Val Val Leu Pro Lys Gln
        50                  55                  60

Met Glu Gln Val Thr Ala Ile Leu Ala Val Cys His Arg Leu Arg Val
65                  70                  75                  80

Pro Val Val Thr Arg Gly Ala Gly Thr Gly Leu Ser Gly Gly Ala Leu
                85                  90                  95

Pro Leu Glu Lys Gly Val Leu Leu Val Met Ala Arg Phe Lys Glu Ile
                100                 105                 110

Leu Asp Ile Asn Pro Val Gly Arg Arg Ala Arg Val Gln Pro Gly Val
            115                 120                 125
```

Arg Asn Leu Ala Ile Ser Gln Ala Val Ala Pro His Asn Leu Tyr Tyr
            130                 135                 140

Ala Pro Asp Pro Ser Ser Gln Ile Ala Cys Ser Ile Gly Gly Asn Val
145                 150                 155                 160

Ala Glu Asn Ala Gly Gly Val His Cys Leu Lys Tyr Gly Leu Thr Val
                165                 170                 175

His Asn Leu Leu Lys Ile Glu Val Gln Thr Leu Asp Gly Glu Ala Leu
            180                 185                 190

Thr Leu Gly Ser Asp Ala Leu Asp Ser Pro Gly Phe Asp Leu Leu Ala
        195                 200                 205

Leu Phe Thr Gly Ser Glu Gly Met Leu Gly Val Thr Thr Glu Val Thr
    210                 215                 220

Val Lys Leu Leu Pro Lys Pro Pro Val Ala Arg Val Leu Leu Ala Ser
225                 230                 235                 240

Phe Asp Ser Val Glu Lys Ala Gly Leu Ala Val Gly Asp Ile Ile Ala
                245                 250                 255

Asn Gly Ile Ile Pro Gly Gly Leu Glu Met Met Asp Asn Leu Ser Ile
            260                 265                 270

Arg Ala Ala Glu Asp Phe Ile His Ala Gly Tyr Pro Val Asp Ala Glu
        275                 280                 285

Ala Ile Leu Leu Cys Glu Leu Asp Gly Val Glu Ser Asp Val Gln Glu
    290                 295                 300

Asp Cys Glu Arg Val Asn Asp Ile Leu Leu Lys Ala Gly Ala Thr Asp
305                 310                 315                 320

Val Arg Leu Ala Gln Asp Glu Ala Glu Arg Val Arg Phe Trp Ala Gly
                325                 330                 335

Arg Lys Asn Ala Phe Pro Ala Val Gly Arg Ile Ser Pro Asp Tyr Tyr
            340                 345                 350

Cys Met Asp Gly Thr Ile Pro Arg Arg Ala Leu Pro Gly Val Leu Glu
        355                 360                 365

Gly Ile Ala Arg Leu Ser Gln Gln Tyr Asp Leu Arg Val Ala Asn Val
    370                 375                 380

Phe His Ala Gly Asp Gly Asn Met His Pro Leu Ile Leu Phe Asp Ala
385                 390                 395                 400

Asn Glu Pro Gly Glu Phe Ala Arg Ala Glu Glu Leu Gly Gly Lys Ile
                405                 410                 415

Leu Glu Leu Cys Val Glu Val Gly Gly Ser Ile Ser Gly Glu His Gly
            420                 425                 430

Ile Gly Arg Glu Lys Ile Asn Gln Met Cys Ala Gln Phe Asn Ser Asp
        435                 440                 445

Glu Ile Thr Thr Phe His Ala Val Lys Ala Ala Phe Asp Pro Asp Gly
    450                 455                 460

Leu Leu Asn Pro Gly Lys Asn Ile Pro Thr Leu His Arg Cys Ala Glu
465                 470                 475                 480

Phe Gly Ala Met His Val His His Gly His Leu Pro Phe Pro Glu Leu
                485                 490                 495

Glu Arg Phe

<210> SEQ ID NO 83
<211> LENGTH: 350
<212> TYPE: PRT
<213> ORGANISM: Escherichia coli

<400> SEQUENCE: 83

Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60

Ala Arg Val Gly Thr Pro Leu Val Thr Ile Glu Ala Ala Leu Glu Ser
65                  70                  75                  80

Ala Gly Gln Met Leu Pro Cys Glu Pro Pro His Tyr Gly Glu Glu Ala
                85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
    130                 135                 140

Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
    210                 215                 220

Lys Ala Ala Arg Glu Leu Leu Gly Gly Glu Val Ala Gly Gln Phe
225                 230                 235                 240

Trp Gln Gln Leu Arg Glu Gln Leu Pro Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285

Ser Thr Ala Glu Asp Asn Gln Ile His Arg Ile Ala Arg Asn Ala Gly
    290                 295                 300

Gly His Ala Thr Arg Phe Ser Ala Gly Asp Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
            340                 345                 350

<210> SEQ ID NO 84
<211> LENGTH: 407
<212> TYPE: PRT
<213> ORGANISM: Escherichia coli

<400> SEQUENCE: 84

Met Gln Thr Gln Leu Thr Glu Glu Met Arg Gln Asn Ala Arg Ala Leu
1               5                   10                  15

Glu Ala Asp Ser Ile Leu Arg Ala Cys Val His Cys Gly Phe Cys Thr

```
            20                  25                  30
Ala Thr Cys Pro Thr Tyr Gln Leu Leu Gly Asp Glu Leu Asp Gly Pro
         35                  40                  45
Arg Gly Arg Ile Tyr Leu Ile Lys Gln Val Leu Glu Gly Asn Glu Val
 50                  55                  60
Thr Leu Lys Thr Gln Glu His Leu Asp Arg Cys Leu Thr Cys Arg Asn
 65                  70                  75                  80
Cys Glu Thr Thr Cys Pro Ser Gly Val Arg Tyr His Asn Leu Leu Asp
                 85                  90                  95
Ile Gly Arg Asp Ile Val Glu Gln Lys Val Lys Arg Pro Leu Pro Glu
            100                 105                 110
Arg Ile Leu Arg Glu Gly Leu Arg Gln Val Val Pro Arg Pro Ala Val
            115                 120                 125
Phe Arg Ala Leu Thr Gln Val Gly Leu Val Leu Arg Pro Phe Leu Pro
    130                 135                 140
Glu Gln Val Arg Ala Lys Leu Pro Ala Glu Thr Val Lys Ala Lys Pro
145                 150                 155                 160
Arg Pro Pro Leu Arg His Lys Arg Arg Val Leu Met Leu Glu Gly Cys
                165                 170                 175
Ala Gln Pro Thr Leu Ser Pro Asn Thr Asn Ala Ala Thr Ala Arg Val
            180                 185                 190
Leu Asp Arg Leu Gly Ile Ser Val Met Pro Ala Asn Glu Ala Gly Cys
        195                 200                 205
Cys Gly Ala Val Asp Tyr His Leu Asn Ala Gln Glu Lys Gly Leu Ala
    210                 215                 220
Arg Ala Arg Asn Asn Ile Asp Ala Trp Trp Pro Ala Ile Glu Ala Gly
225                 230                 235                 240
Ala Glu Ala Ile Leu Gln Thr Ala Ser Gly Cys Gly Ala Phe Val Lys
                245                 250                 255
Glu Tyr Gly Gln Met Leu Lys Asn Asp Ala Leu Tyr Ala Asp Lys Ala
            260                 265                 270
Arg Gln Val Ser Glu Leu Ala Val Asp Leu Val Glu Leu Leu Arg Glu
        275                 280                 285
Glu Pro Leu Glu Lys Leu Ala Ile Arg Gly Asp Lys Lys Leu Ala Phe
    290                 295                 300
His Cys Pro Cys Thr Leu Gln His Ala Gln Lys Leu Asn Gly Glu Val
305                 310                 315                 320
Glu Lys Val Leu Leu Arg Leu Gly Phe Thr Leu Thr Asp Val Pro Asp
                325                 330                 335
Ser His Leu Cys Cys Gly Ser Ala Gly Thr Tyr Ala Leu Thr His Pro
            340                 345                 350
Asp Leu Ala Arg Gln Leu Arg Asp Asn Lys Met Asn Ala Leu Glu Ser
        355                 360                 365
Gly Lys Pro Glu Met Ile Val Thr Ala Asn Ile Gly Cys Gln Thr His
    370                 375                 380
Leu Ala Ser Ala Gly Arg Thr Ser Val Arg His Trp Ile Glu Ile Val
385                 390                 395                 400
Glu Gln Ala Leu Glu Lys Glu
                405

<210> SEQ ID NO 85
<211> LENGTH: 828
<212> TYPE: DNA
<213> ORGANISM: Escherichia coli
```

<400> SEQUENCE: 85

```
atggctaatc caaccgttat taagctacag gatggcaatg tcatgcccca gctgggactg      60
ggcgtctggc aagcaagtaa tgaggaagta atcaccgcca ttcaaaaagc gttagaagtg     120
ggttatcgct cgattgatac cgccgcggcc tacaagaacg aagaaggtgt cggcaaagcc     180
ctgaaaaatg cctcagtcaa cagagaagaa ctgttcatca ccactaagct gtggaacgac     240
gaccacaagc gcccccgcga agccctgctc gacagcctga aaaaactcca gcttgattat     300
atcgacctct acttaatgca ctggcccgtt ccgctatcg accattatgt cgaagcatgg      360
aaaggcatga tcgaattgca aaagagggga ttaatcaaaa gcatcggcgt gtgcaacttc     420
cagatccatc acctgcaacg cctgattgat gaaactggcg tgacgcctgt gataaaccag     480
atcgaacttc atccgctgat gcaacaacgc cagctacacg cctggaacgc gacacacaaa     540
atccagaccg aatcctggag cccattagcg caaggaggga aaggcgtttt cgatcagaaa     600
gtcattcgcg atctggcaga taaatacggc aaaaccccgg cgcagattgt tatccgctgg     660
catctggata gcggcctggt ggtgatcccg aaatcggtca ccttcacg tattgccgaa       720
aactttgatg tctgggattt ccgtctcgac aaagacgaac tcggcgaaat tgcaaaactc     780
gatcagggca agcgtctcgg tcccgatcct gaccagttcg gcggctaa                   828
```

<210> SEQ ID NO 86
<211> LENGTH: 275
<212> TYPE: PRT
<213> ORGANISM: Escherichia coli

<400> SEQUENCE: 86

```
Met Ala Asn Pro Thr Val Ile Lys Leu Gln Asp Gly Asn Val Met Pro
1               5                   10                  15
Gln Leu Gly Leu Gly Val Trp Gln Ala Ser Asn Glu Glu Val Ile Thr
            20                  25                  30
Ala Ile Gln Lys Ala Leu Glu Val Gly Tyr Arg Ser Ile Asp Thr Ala
        35                  40                  45
Ala Ala Tyr Lys Asn Glu Glu Gly Val Gly Lys Ala Leu Lys Asn Ala
    50                  55                  60
Ser Val Asn Arg Glu Glu Leu Phe Ile Thr Thr Lys Leu Trp Asn Asp
65                  70                  75                  80
Asp His Lys Arg Pro Arg Glu Ala Leu Leu Asp Ser Leu Lys Lys Leu
                85                  90                  95
Gln Leu Asp Tyr Ile Asp Leu Tyr Leu Met His Trp Pro Val Pro Ala
            100                 105                 110
Ile Asp His Tyr Val Glu Ala Trp Lys Gly Met Ile Glu Leu Gln Lys
        115                 120                 125
Glu Gly Leu Ile Lys Ser Ile Gly Val Cys Asn Phe Gln Ile His His
    130                 135                 140
Leu Gln Arg Leu Ile Asp Glu Thr Gly Val Thr Pro Val Ile Asn Gln
145                 150                 155                 160
Ile Glu Leu His Pro Leu Met Gln Gln Arg Gln Leu His Ala Trp Asn
                165                 170                 175
Ala Thr His Lys Ile Gln Thr Glu Ser Trp Ser Pro Leu Ala Gln Gly
            180                 185                 190
Gly Lys Gly Val Phe Asp Gln Lys Val Ile Arg Asp Leu Ala Asp Lys
        195                 200                 205
Tyr Gly Lys Thr Pro Ala Gln Ile Val Ile Arg Trp His Leu Asp Ser
```

```
            210                 215                 220
Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
        275
```

<210> SEQ ID NO 87
<211> LENGTH: 1050
<212> TYPE: DNA
<213> ORGANISM: Escherichia coli

<400> SEQUENCE: 87

```
atgaagatca aagctgttgg tgcatattcc gctaaacaac cacttgaacc gatggatatc      60
acccggcgtg aaccgggacc gaatgatgtc aaaatcgaaa tcgcttactg tggcgtttgc     120
cattccgatc tccaccaggt ccgttccgag tgggcgggga cggtttaccc ctgcgtgccg     180
ggtcatgaaa ttgtggggcg tgtggtagcc gttggtgatc aggtagaaaa atatgcgccg     240
ggcgatctgg tcggtgtcgg ctgcattgtc gacagttgta acattgcga agagtgtgaa     300
gacgggttgg aaaactactg tgatcacatg accggcacct ataactcgcc gacgccggac     360
gaaccgggcc atactctggg cggctactca aacagatcg tcgttcatga gcgatatgtt     420
ctgcgtattc gtcacccgca agagcagctg gcggcggtgg ctcctttgtt gtgtgcaggg     480
atcaccacgt attcgccgct acgtcactgg caggccgggc cgggtaaaaa agtgggcgtg     540
gtcggcatcg gcggtctggg acatatgggg attaagctgg cccacgcgat gggggcacat     600
gtggtggcat ttaccacttc tgaggcaaaa cgcgaagcgg caaaagccct ggggccgat     660
gaagttgtta actcacgcaa tgccgatgag atggcggctc atctgaagag tttcgatttc     720
attttgaata cagtagctgc gccacataat ctcgacgatt ttaccacctt gctgaagcgt     780
gatggcacca tgacgctggt tggtgcgcct gcgacaccgc ataaatcgcc ggaagttttc     840
aacctgatca tgaaacgccg tgcgatagcc ggttctatga ttggcggcat tccagaaact     900
caggagatgc tcgatttttg cgccgaacat ggcatcgtgg ctgatataga gatgattcgg     960
gccgatcaaa ttaatgaagc ctatgagcga atgctgcgcg gtgatgtgaa atatcgtttt    1020
gttatcgata tcgcacact aacagactga                                       1050
```

<210> SEQ ID NO 88
<211> LENGTH: 349
<212> TYPE: PRT
<213> ORGANISM: Escherichia coli

<400> SEQUENCE: 88

```
Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
            20                  25                  30

Glu Ile Ala Tyr Cys Gly Val Cys His Ser Asp Leu His Gln Val Arg
        35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
```

|    |     |     |     |     | 65  |     |     |     | 70  |     |     |     |     | 75  |     |     |     |     | 80  |
|----|-----|-----|-----|-----|-----|-----|-----|-----|-----|-----|-----|-----|-----|-----|-----|-----|-----|-----|-----|

Gly Asp Leu Val Gly Val Gly Cys Ile Val Asp Ser Cys Lys His Cys
                    85                  90                  95

Glu Glu Cys Glu Asp Gly Leu Glu Asn Tyr Cys Asp His Met Thr Gly
                100                 105                 110

Thr Tyr Asn Ser Pro Thr Pro Asp Glu Pro Gly His Thr Leu Gly Gly
                115                 120                 125

Tyr Ser Gln Gln Ile Val Val His Glu Arg Tyr Val Leu Arg Ile Arg
130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
                180                 185                 190

Leu Ala His Ala Met Gly Ala His Val Ala Phe Thr Thr Ser Glu
                195                 200                 205

Ala Lys Arg Glu Ala Ala Lys Ala Leu Gly Ala Asp Glu Val Val Asn
210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
                245                 250                 255

Leu Leu Lys Arg Asp Gly Thr Met Thr Leu Val Gly Ala Pro Ala Thr
                260                 265                 270

Pro His Lys Ser Pro Glu Val Phe Asn Leu Ile Met Lys Arg Arg Ala
                275                 280                 285

Ile Ala Gly Ser Met Ile Gly Gly Ile Pro Glu Thr Gln Glu Met Leu
                290                 295                 300

Asp Phe Cys Ala Glu His Gly Ile Val Ala Asp Ile Glu Met Ile Arg
305                 310                 315                 320

Ala Asp Gln Ile Asn Glu Ala Tyr Glu Arg Met Leu Arg Gly Asp Val
                325                 330                 335

Lys Tyr Arg Phe Val Ile Asp Asn Arg Thr Leu Thr Asp
                340                 345

```
<210> SEQ ID NO 89
<211> LENGTH: 1305
<212> TYPE: DNA
<213> ORGANISM: Escherichia coli

<400> SEQUENCE: 89
atgaaaaccc gtacacaaca aattgaagaa ttacagaaag agtggactca accgcgttgg      60
gaaggcatta ctcgcccata cagtgcggaa gatgtggtga aattacgcgg ttcagtcaat     120
cctgaatgca cgctggcgca actgggcgca gcgaaaatgt ggcgtctgct gcacggtgag     180
tcgaaaaaag gctacatcaa cagcctcggc gcactgactg gcggtcaggc gctgcaacag     240
gcgaaagcgg gtattgaagc agtctatctg tcgggatggc aggtagcggc ggacgctaac     300
ctggcggcca gcatgtatcc ggatcagtcg ctctatccgg caaactcggt gccagctgtg     360
gtggagcgga tcaacaacac cttccgtcgt gccgatcaga tccaatggtc cgcgggcatt     420
gagccgggcg atccgcgcta tgtcgattac ttcctgccga tcgttgccga tgcggaagcc     480
ggttttggcg gtgtcctgaa tgcctttgaa ctgatgaaag cgatgattga agccggtgca     540
```

-continued

```
gcggcagttc acttcgaaga tcagctggcg tcagtgaaga aatgcggtca catgggcggc      600
aaagttttag tgccaactca ggaagctatt cagaaactgg tcgcggcgcg tctggcagct      660
gacgtgacgg gcgttccaac cctgctggtt gcccgtaccg atgctgatgc ggcggatctg      720
atcacctccg attgcgaccc gtatgacagc gaatttatta ccggcgagcg taccagtgaa      780
ggcttcttcc gtactcatgc gggcattgag caagcgatca gccgtggcct ggcgtatgcg      840
ccatatgctg acctggtctg tgtgaaacc tccacgccgg atctggaact ggcgcgtcgc      900
tttgcacaag ctatccacgc gaaatatccg ggcaaactgc tggcttataa ctgctcgccg      960
tcgttcaact ggcagaaaaa cctcgacgac aaaactattg ccagcttcca gcagcagctg     1020
tcggatatgg gctacaagtt ccagttcatc accctggcag gtatccacag catgtggttc     1080
aacatgtttg acctggcaaa cgcctatgcc cagggcgagg gtatgaagca ctacgttgag     1140
aaagtgcagc agccggaatt tgccgccgcg aaagatggct ataccttcgt atctcaccag     1200
caggaagtgg gtacaggtta cttcgataaa gtgacgacta ttattcaggg cggcacgtct     1260
tcagtcaccg cgctgaccgg ctccactgaa gaatcgcagt tctaa                      1305
```

<210> SEQ ID NO 90
<211> LENGTH: 434
<212> TYPE: PRT
<213> ORGANISM: Escherichia coli

<400> SEQUENCE: 90

```
Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240
```

```
Ile Thr Ser Asp Cys Asp Pro Tyr Asp Ser Glu Phe Ile Thr Gly Glu
                245                 250                 255
Arg Thr Ser Glu Gly Phe Phe Arg Thr His Ala Gly Ile Glu Gln Ala
            260                 265                 270
Ile Ser Arg Gly Leu Ala Tyr Ala Pro Tyr Ala Asp Leu Val Trp Cys
        275                 280                 285
Glu Thr Ser Thr Pro Asp Leu Glu Leu Ala Arg Arg Phe Ala Gln Ala
    290                 295                 300
Ile His Ala Lys Tyr Pro Gly Lys Leu Leu Ala Tyr Asn Cys Ser Pro
305                 310                 315                 320
Ser Phe Asn Trp Gln Lys Asn Leu Asp Asp Lys Thr Ile Ala Ser Phe
                325                 330                 335
Gln Gln Gln Leu Ser Asp Met Gly Tyr Lys Phe Gln Phe Ile Thr Leu
            340                 345                 350
Ala Gly Ile His Ser Met Trp Phe Asn Met Phe Asp Leu Ala Asn Ala
        355                 360                 365
Tyr Ala Gln Gly Glu Gly Met Lys His Tyr Val Glu Lys Val Gln Gln
    370                 375                 380
Pro Glu Phe Ala Ala Lys Asp Gly Tyr Thr Phe Val Ser His Gln
385                 390                 395                 400
Gln Glu Val Gly Thr Gly Tyr Phe Asp Lys Val Thr Thr Ile Ile Gln
                405                 410                 415
Gly Gly Thr Ser Ser Val Thr Ala Leu Thr Gly Ser Thr Glu Glu Ser
            420                 425                 430
Gln Phe

<210> SEQ ID NO 91
<211> LENGTH: 939
<212> TYPE: DNA
<213> ORGANISM: Escherichia coli

<400> SEQUENCE: 91
atggatatca tcttttatca cccaacgttc gatacccaat ggtggattga ggcactgcgc      60
aaagctattc ctcaggcaag agtcagagca tggaaaagcg gagataatga ctctgctgat     120
tatgctttag tctggcatcc tcctgttgaa atgctggcag gcgcgatctc taaagcggtg     180
ttcgcactcg gggccggtgt tgattctatt ttgagcaagc tacaggcaca ccctgaaatg     240
ctgaacccct tctgttccact ttttcgcctg aagataccg gtatgggcga gcaaatgcag     300
gaatatgctg tcagtcaggt gctgcattgg tttcgacgtt ttgacgatta tcgcatccag     360
caaaatagtt cgcattggca accgctgcct gaatatcatc gggaagattt taccatcggc     420
attttgggcg caggcgtact gggcagtaaa gttgctcaga gtctgcaaac ctggcgcttt     480
ccgctgcgtt gctggagtcg aacccgtaaa tcgtggcctg gcgtgcaaag ctttgccgga     540
cgggaagaac tgtctgcatt tctgagccaa tgtcgggtat tgattaattt gttaccgaat     600
accctgaaa ccgtcggcat tattaatcaa caattactcg aaaaattacc ggatggcgcg      660
tatctcctca acctggcgcg tggtgttcat gttgtggaag atgacctgct cgcggcgctg     720
gatagcggca agttaaagg cgcaatgttg atgttttta atcgtgaacc cttaccgcct      780
gaaagtccgc tctggcaaca tccacgcgtg acgataacac acatgtcgc cgcgattacc      840
cgtcccgctg aagctgtgga gtacatttct cgcaccattg cccagctcga aaaggggag      900
agggtctgcg ggcaagtcga ccgcgcacgc ggctactaa                            939
```

<210> SEQ ID NO 92
<211> LENGTH: 312
<212> TYPE: PRT
<213> ORGANISM: Escherichia coli

<400> SEQUENCE: 92

Met Asp Ile Ile Phe Tyr His Pro Thr Phe Asp Thr Gln Trp Trp Ile
1               5                   10                  15

Glu Ala Leu Arg Lys Ala Ile Pro Gln Ala Arg Val Arg Ala Trp Lys
            20                  25                  30

Ser Gly Asp Asn Asp Ser Ala Asp Tyr Ala Leu Val Trp His Pro Pro
        35                  40                  45

Val Glu Met Leu Ala Gly Arg Asp Leu Lys Ala Val Phe Ala Leu Gly
    50                  55                  60

Ala Gly Val Asp Ser Ile Leu Ser Lys Leu Gln Ala His Pro Glu Met
65                  70                  75                  80

Leu Asn Pro Ser Val Pro Leu Phe Arg Leu Glu Asp Thr Gly Met Gly
                85                  90                  95

Glu Gln Met Gln Glu Tyr Ala Val Ser Gln Val Leu His Trp Phe Arg
            100                 105                 110

Arg Phe Asp Asp Tyr Arg Ile Gln Gln Asn Ser Ser His Trp Gln Pro
        115                 120                 125

Leu Pro Glu Tyr His Arg Glu Asp Phe Thr Ile Gly Ile Leu Gly Ala
    130                 135                 140

Gly Val Leu Gly Ser Lys Val Ala Gln Ser Leu Gln Thr Trp Arg Phe
145                 150                 155                 160

Pro Leu Arg Cys Trp Ser Arg Thr Arg Lys Ser Trp Pro Gly Val Gln
                165                 170                 175

Ser Phe Ala Gly Arg Glu Glu Leu Ser Ala Phe Leu Ser Gln Cys Arg
            180                 185                 190

Val Leu Ile Asn Leu Leu Pro Asn Thr Pro Glu Thr Val Gly Ile Ile
        195                 200                 205

Asn Gln Gln Leu Leu Glu Lys Leu Pro Asp Gly Ala Tyr Leu Leu Asn
    210                 215                 220

Leu Ala Arg Gly Val His Val Val Glu Asp Asp Leu Leu Ala Ala Leu
225                 230                 235                 240

Asp Ser Gly Lys Val Lys Gly Ala Met Leu Asp Val Phe Asn Arg Glu
                245                 250                 255

Pro Leu Pro Pro Glu Ser Pro Leu Trp Gln His Pro Arg Val Thr Ile
            260                 265                 270

Thr Pro His Val Ala Ala Ile Thr Arg Pro Ala Glu Ala Val Glu Tyr
        275                 280                 285

Ile Ser Arg Thr Ile Ala Gln Leu Glu Lys Gly Glu Arg Val Cys Gly
    290                 295                 300

Gln Val Asp Arg Ala Arg Gly Tyr
305                 310

<210> SEQ ID NO 93
<211> LENGTH: 1056
<212> TYPE: DNA
<213> ORGANISM: Clostridium beijerinckii

<400> SEQUENCE: 93
atgaaagggt tgccatgtt aggtatcaat aaactgggct ggattgaaaa agagcgcccg      60
gtggcgggtt catacgatgc aattgttcgt ccgctggccg tcagtccgtg caccagcgac     120

-continued

```
atccatacag tctttgaagg tgccctgggt gatcggaaaa acatgattct gggccatgaa    180
gccgtaggcg aagtagtgga agtgggcagc gaggtaaagg atttcaaacc gggtgatcgc    240
gtaattgttc cttgcacgac cccagattgg cgctcactgg aagttcaggc tggttttcag    300
cagcatagta acggtatgtt agcaggctgg aagtttagca attttaaaga cggggtgttc    360
ggggagtatt ttcatgtcaa cgatgcggac atgaatctgg ctattttacc taaagatatg    420
ccgctggaga acgcagtgat gattaccgac atgatgacga caggctttca cggtgcagaa    480
ctggctgaca tccaaatggg ctccagtgtg gtggttatcg gtattggtgc ggtcgggctg    540
atgggtatcg cgggcgcgaa attacggggc gctggtcgca tcatcggtgt cggcagccgt    600
ccaatttgcg ttgaagcagc taaattctat ggtgccacgg acattctgaa ctataaaaat    660
ggtcacatcg tcgatcaggt gatgaaactg accaatggca aaggtgtgga ccgcgtgatc    720
atggcgggcg gcggctcaga gactttatct caagcggtgt ctatggttaa acctgggggc    780
atcatttcta atattaacta tcatggctcc ggcgacgcat tactgatccc gcgtgttgaa    840
tggggctgtg ggatggccca caaaaccatt aaagggggt tatgtccggg tggtcgcctg     900
cgtgccgaaa tgctgcgtga catggtggtt tacaaccgtg tggatctgtc caaactggta    960
actcacgtat accacggttt cgatcacatt gaagaggcgc tgctgctgat gaaggataag   1020
ccaaaggatc tgattaaggc ggttgttatc ctgtaa                             1056

<210> SEQ ID NO 94
<211> LENGTH: 351
<212> TYPE: PRT
<213> ORGANISM: Clostridium beijerinckii

<400> SEQUENCE: 94

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205
```

```
Phe Tyr Gly Ala Thr Asp Ile Leu Asn Tyr Lys Asn Gly His Ile Val
    210                 215                 220
Asp Gln Val Met Lys Leu Thr Asn Gly Lys Gly Val Asp Arg Val Ile
225                 230                 235                 240
Met Ala Gly Gly Gly Ser Glu Thr Leu Ser Gln Ala Val Ser Met Val
                245                 250                 255
Lys Pro Gly Gly Ile Ile Ser Asn Ile Asn Tyr His Gly Ser Gly Asp
            260                 265                 270
Ala Leu Leu Ile Pro Arg Val Glu Trp Gly Cys Gly Met Ala His Lys
        275                 280                 285
Thr Ile Lys Gly Gly Leu Cys Pro Gly Gly Arg Leu Arg Ala Glu Met
    290                 295                 300
Leu Arg Asp Met Val Val Tyr Asn Arg Val Asp Leu Ser Lys Leu Val
305                 310                 315                 320
Thr His Val Tyr His Gly Phe Asp His Ile Glu Glu Ala Leu Leu Leu
                325                 330                 335
Met Lys Asp Lys Pro Lys Asp Leu Ile Lys Ala Val Val Ile Leu
            340                 345                 350
```

<210> SEQ ID NO 95
<211> LENGTH: 95
<212> TYPE: DNA
<213> ORGANISM: Escherichia coli

<400> SEQUENCE: 95
gattgatttg tcgcaatgat tgacacgatt ccgcttgacg ctgcgtaagg ttttttgtaat    60 tttacaggca accttttatt cactaacaaa tagct                                95

<210> SEQ ID NO 96
<211> LENGTH: 190
<212> TYPE: DNA
<213> ORGANISM: Artificial Sequence
<220> FEATURE:
<223> OTHER INFORMATION: OXB20 Promoter

<400> SEQUENCE: 96
aagctgttgt gaccgcttgc tctagccagc tatcgagttg tgaaccgatc catctagcaa    60
ttggtctcga tctagcgata ggcttcgatc tagctatgta gaaacgccgt gtgctcgatc   120
gcttgataag gtccacgtag ctgctataat tgcttcaaca gaacatattg actatccggt   180
attacccggc                                                          190

<210> SEQ ID NO 97
<211> LENGTH: 768
<212> TYPE: DNA
<213> ORGANISM: Burkholderia xenovorans

<400> SEQUENCE: 97
atgtcatacg caatttaccc ttcgttaagt ggtaagacag tggtgattac tggggggga    60 tcaggaatcg gagctgcgat ggttgaagca ttcgcccgcc agggagcgcg tgtatttttt   120
ttggatgtag ccgaagatga ctcgcttgcg cttcaacaga gcctgtccga cgcgccacac   180
ccacccctgt tccgtcgctg tgacttacgc tcagtagacg caatccattc cgcctttgca   240
ggtatcgttg aaatcgcagg gccgattgag gttttggtta acaatgcagg caatgacgat   300
cgtcatgagg tcgacgctat tacaccggcg tattgggacg agcgcatggc cgtgaatctg   360
cgccatcaat tcttctgtgc ccaagctgcg gctgctggaa tgcgtaaaat tggacgcggg   420

```
gtcatcctga atttgggtag tgtttcctgg catcttgcgt tgccgaactt ggcgatctac    480
atgagtgcga aggcgggtat tgagggcctg actcgtggac ttgcacgcga tttgggcgca    540
gccggcatcc gcgtaaattg tattattcct ggagctgtac gtacgccccg tcagatgcag    600
ctttggcagt ccccggagtc ggaagcgaag ctggtggcgt cacagtgtct tcgtcttcgc    660
atcgaacccg agcacgtagc tcgcatggca ttatttttgg catctgacga cgcaagccgc    720
tgttcaggcc gcgattattt cgttgatgct ggctggtatg gagagtaa                 768
```

<210> SEQ ID NO 98
<211> LENGTH: 382
<212> TYPE: PRT
<213> ORGANISM: Escherichia coli

<400> SEQUENCE: 98

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320
```

```
Ala Ala Val Glu Ala Val Phe Ala Leu Asn Arg Asp Val Gly Ile Pro
            325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
            355                 360                 365

Ala Thr Leu Glu Asp Ile Val Glu Leu Tyr His Thr Ala Trp
    370                 375                 380
```

METABOLIC ENGINEERING FOR SIMULTANEOUS CONSUMPTION OF XYLOSE AND GLUCOSE FOR PRODUCTION OF CHEMICALS FROM SECOND GENERATION SUGARS

CROSS-REFERENCE TO RELATED APPLICATION

This application claims priority to U.S. Provisional Application No. 62/829,398 filed Apr. 4, 2019, the content of which are incorporated by reference in their entirety herein.

STATEMENT REGARDING SEQUENCE LISTING

The sequence listing associated with this application is provided in text format in lieu of a paper copy, and is hereby incorporated by reference into the specification. The name of the text file containing the sequence listing is BRSK_021_01US_ST25.txt. The text file is 222 kb, and was created on Apr. 4, 2020, and is being submitted electronically.

BACKGROUND OF THE DISCLOSURE

The production of desirable chemicals such as monoethylene glycol, glycolic acid, C3 compounds (such as acetone, isopropanol and propene), amino acids, and polyols from alternative feedstocks, like pentoses, is an alternative to deriving the same from petroleum-based chemicals.

The utilization of xylose, a pentose, is a source of differentiation from most renewable chemicals projects. Lignocellulosic biomass is a promising renewable feedstock given that the utilization of lignocellulosic biomass as a feedstock does not require utilizing a plant that would otherwise produce foodstuffs. Lignocellulosic biomass is further promising as a renewable feedstock due to its sustainability and worldwide availability. The separation and isolation of lignocellulosic sugars is one option to increase sugar production without increasing land-use. Xylose is the primary carbon source in hemicellulosic hydrolysates, followed by glucose and arabinose. Xylose typically represents 70-80% of sugars present in hemicellulosic hydrolysates, while glucose accounts for 10-20%.

In *Escherichia coli*, even minimal amounts of glucose completely inhibit the uptake of xylose (even if xylose is the predominant sugar), thus limiting the overall conversion of sugars into desirable chemicals. In an industrial process productivity (g of product/liter per hour) is a key factor to ensure an economic viability, thus microbial strains have to be capable of constantly converting a primary substrate, such as xylose, into product at a maximum rate. Considering that glucose is present in the lignocellulosic hydrolysate, in a batch operation, xylose uptake will be delayed until complete depletion of glucose, decreasing productivity. If we consider a fed batch or continuous operation, a stream containing both xylose and glucose is constantly fed to the reactor, reinforcing the repression potential of glucose, and thus failing to maximize the potential productivity of a microbe's ability to produce one or more products from a common renewable feedstock.

There exists a need to maximize the productivity of microbes capable of producing desirable products from renewable feedstocks, particularly the need to maximize the use of multiple carbon sources while minimizing or eliminating the repression activities of carbon sources on the microbes.

As set forth herein, the disclosure provides methods and compositions for the engineering of microbes to utilize a mixed stream of sugars for production of desirable chemicals without concern for the typical catabolic repression effects of set into motion due to the presence of the mixed stream of sugars.

SUMMARY OF THE DISCLOSURE

In some aspects, the disclosure is generally drawn to a recombinant microorganism capable of producing a fermentation product from a feedstock comprising xylose and glucose, wherein the recombinant microorganism simultaneously utilizes xylose and glucose, and wherein the microorganism comprises one or more of the following: (a) deletion or inactivation of a pentose ATP-binding transporter proteins from the genome of the microorganism such that the transporter proteins are not expressed; (b) one or more endogenous or exogenous nucleic acid sequences encoding at least one of a C5 sugar symporter operatively linked to one or more constitutive promoters; wherein the C5 sugar symporter comprises: (1) a xylose symporter and/or a (2) an arabinose symporter; (c) one or more endogenous or exogenous nucleic acid sequences encoding (1) a xylose isomerase operatively linked to one or more constitutive promoters, and deletion or inactivation of one or more xylulokinases and/or (2) a xylose dehydrogenase operatively linked to one or more constitutive promoters and deletion or inactivation of one or more xylose isomerases and/or one or more xylulokinases.

In some aspects, the fermentation product produced by the microorganism is one or more molecules comprising 1, 2, 3, 4, 5, 6, 7, 8, 9, or 10 carbons. In some aspects, two or more molecules are produced simultaneously.

In some aspects, the disclosure is generally drawn to a recombinant *E. coli* capable of producing a fermentation product from a feedstock comprising xylose and glucose, wherein the recombinant microorganism simultaneously utilizes xylose and glucose, and wherein the microorganism comprises one or more of the following: (a) deletion or inactivation of ATP-binding transporter proteins araFGH and xylFGH from the genome of the microorganism such that the transporter proteins are not expressed; (b) one or more endogenous or exogenous nucleic acid sequences encoding at least one of a C5 sugar symporter operatively linked to one or more constitutive promoters; wherein the C5 sugar symporter comprises: (1) a xylose symporter and/or a (2) an arabinose symporter; (c) one or more endogenous or exogenous nucleic acid sequences encoding (1) a xylose isomerase operatively linked to one or more constitutive promoters and deletion or inactivation of one or more xylulokinases and/or (2) a xylose dehydrogenase operatively linked to one or more constitutive promoters and deletion or inactivation of one or more xylose isomerases and/or one or more xylulokinases.

In some aspects, the disclosure is generally drawn to a recombinant microorganism capable of producing monoethylene glycol (MEG) and/or acetone from a feedstock comprising xylose and glucose, wherein the recombinant microorganism simultaneously utilizes xylose and glucose, comprising one or more of the following: (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism expresses pathways for MEG and/or acetone production.

In some aspects, the recombinant microorganism of claim 5, wherein the microorganism further comprises the deletion or inactivation of glcDEF. In some aspects, the C5 symporter is controlled by a GAPDH promoter at the araFGH locus. In some aspects, the C5 sugar symporter is a xylose symporter XylE. In some aspects, the XylE comprises an amino acid sequence comprising SEQ ID NO: 49. In some aspects, the XylE is encoded by a nucleic acid sequence comprising SEQ ID NO: 48. In some aspects, the xylose symporter is endogenous to the microorganism.

In some aspects, the C5 sugar symporter is an arabinose symporter AraE. In some aspects, the AraE comprises an amino acid sequence comprising SEQ ID NO: 47. In some aspects, the AraE is encoded by a nucleic acid sequence comprising SEQ ID NO: 46. In some aspects, the arabinose symporter is endogenous to the microorganism.

In some aspects, uptake of the xylose is not sensitive to catabolic repression by other monosaccharides. In some aspects, the microorganism comprises a functional phosphotransferase system. In some aspects, the microorganism comprises a native wild-type nucleic acid sequence encoding a cAMP receptor protein (CRP). In some aspects, the CRP comprises an amino acid sequence comprising SEQ ID NO: 10. In some aspects, the CRP is encoded by a nucleic acid sequence comprising SEQ ID NO: 9.

In some aspects, the constitutive overexpression of the xylose symporter enables continuous import of xylose from the feedstock into the microorganism. In some aspects, the constitutive overexpression of the arabinose symporter enables continuous import of xylose from the feedstock into the microorganism. In some aspects, the continuous xylose import occurs independent of the presence of other sugars in the feedstock.

In some aspects, the recombinant microorganism comprises a pathway for MEG production with one or more of the following from (c) through (e); (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylulokinases from the genome of a parent microorganism. In some aspects, (c) and (d) are in an operon controlled by the proD promoter. In some aspects, the proD promoter is encoded by a nucleic acid sequence comprising SEQ ID NO: 53.

In some aspects, the xylose isomerase is XylA. In some aspects, the xylose isomerase is endogenous to the microorganism. In some aspects, the XylA comprises an amino acid sequence comprising SEQ ID NO: 6. In some aspects, the XylA is encoded by a nucleic acid sequence comprising SEQ ID NO: 5.

In some aspects, the ketohexokinase is from *Homo Sapiens*. In some aspects, the ketohexokinase is heterologous to the microorganism. In some aspects, the ketohexokinase is khk-C. In some aspects, the khk-C comprises an amino acid sequence comprising SEQ ID NO: 12. In some aspects, the khk-C is encoded by a nucleic acid sequence comprising SEQ ID NO: 11.

In some aspects, the fructose-biphosphate aldolase is from *Homo Sapiens*. In some aspects, the fructose-biphosphate aldolase is heterologous to the microorganism. In some aspects, the fructose-biphosphate aldolase is aldoB. In some aspects, the aldoB comprises an amino acid sequence comprising SEQ ID NO: 51. In some aspects, the aldoB is encoded by a nucleic acid sequence comprising SEQ ID NO: 50.

In some aspects, the glycoaldehyde reductase is endogenous to the microorganism. In some aspects, the glycoaldehyde reductase is fucO. In some aspects, the fucO comprises an amino acid sequence comprising SEQ ID NO: 98. In some aspects, the fucO is encoded by a nucleic acid sequence comprising SEQ ID NO: 52.

In some aspects, the xylulokinase is XylB. In some aspects, the xylB comprises an amino acid sequence comprising SEQ ID NO: 14. In some aspects, the xylB is encoded by a nucleic acid sequence comprising SEQ ID NO: 13.

In some aspects, the recombinant microorganism comprises a pathway for MEG production with one or more of the following from (c) through (e); (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylose isomerases and/or one or more xylulokinases from the genome of a parent microorganism.

In some aspects, the xylose dehydrogenase is from *Caulobacter crescentus, Burkholderia xenovorans, Haloferax volcanii*. In some aspects, the xylose dehydrogenase is xdh. In some aspects, the xdh comprises an amino acid sequence comprising SEQ ID NO: 16, 17 or 19. In some aspects, the xdh is encoded by a nucleic acid sequence comprising SEQ ID NO: 15, 18 or 97. In some aspects, the xylose dehydrogenase is heterologous to the microorganism.

In some aspects, the xylonolactonase is from *Caulobacter crescentus, Burkholderia xenovorans, Haloferax volcanii*. In some aspects, the xylonolactonase is xylC. In some aspects, the xylC comprises an amino acid sequence comprising SEQ ID NO: 55, 57 or 59. In some aspects, the xylC is encoded by a nucleic acid sequence comprising SEQ ID NO: 54, 56 or 58.

In some aspects, the xylonolactonase is heterologous to the microorganism. In some aspects, the xylonolactonase is endogenous to the microorganism.

In some aspects, the xylose dehydratase is from *Caulobacter crescentus, Burkholderia xenovorans, Haloferax volcanii*. In some aspects, the xylose dehydratase is xylD. In some aspects, the xylD comprises an amino acid sequence comprising SEQ ID NO: 61, 63 or 65. In some aspects, the xylD is encoded by a nucleic acid sequence comprising SEQ ID NO: 60, 62 or 64. In some aspects, the xylose dehydratase is heterologous to the microorganism. In some aspects, the xylose dehydratase is endogenous to the microorganism.

In some aspects, the glycoaldehyde reductase is endogenous to the microorganism. In some aspects, the glycoaldehyde reductase is fucO. In some aspects, the fucO comprises an amino acid sequence comprising SEQ ID NO: 98. In some aspects, the fucO is encoded by a nucleic acid sequence comprising SEQ ID NO: 52.

In some aspects, the glycoaldehyde reductase is heterologous to the microorganism. In some aspects, the xylose isomerase is XylA. In some aspects, the xylA comprises an amino acid sequence comprising SEQ ID NO: 6. In some aspects, the xylA is encoded by a nucleic acid sequence comprising SEQ ID NO: 5.

In some aspects, the xylulokinase is XylB. In some aspects, the xylB comprises an amino acid sequence comprising SEQ ID NO: 14. In some aspects, the xylB is encoded by a nucleic acid sequence comprising SEQ ID NO: 13.

In some aspects, the recombinant microorganism further comprises a pathway for acetone production with one or more of the following from (f) to (h): (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone.

In some aspects, (f), (g) and (h) are in an operon controlled by the OXB11 promoter. In some aspects, the OXB11 promoter is encoded by a nucleic acid sequence comprising SEQ ID NO: 78. In some aspects, the acetoacetyl-CoA thiolase is from *Clostridium acetobutylicum*. In some aspects, the acetoacetyl-CoA thiolase comprises an amino acid sequence comprising SEQ ID NO: 67 or 69. In some aspects, the acetoacetyl-CoA thiolase is encoded by a nucleic acid sequence comprising SEQ ID NO: 66 or 68. In some aspects, the acetate:acetoacetyl-CoA transferase is a AtoDA. In some aspects, the AtoDA subunit alpha comprises an amino acid sequence comprising SEQ ID NO: 72. In some aspects, the AtoDA subunit alpha is encoded by a nucleic acid sequence comprising SEQ ID NO: 70. In some aspects, the AtoDA subunit beta comprises an amino acid sequence comprising SEQ ID NO: 73. In some aspects, the AtoDA subunit beta is encoded by a nucleic acid sequence comprising SEQ ID NO: 71.

The recombinant microorganism of claim 77, wherein the acetoacetate decarboxylase is from *Clostridium beijerinckii* or *Clostridium acetobutylicum*. In some aspects, the acetoacetate decarboxylase is Adc. In some aspects, the Adc comprises an amino acid sequence comprising SEQ ID NO: 75 or 77. In some aspects, the Adc is encoded by a nucleic acid sequence comprising SEQ ID NO: 74 or 76.

In some aspects, the recombinant microorganism further comprises a pathway for isopropanol production with one or more of the following from (f) to (i): (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone (i) expression of at least one exogenous nucleic acid molecule encoding an alcohol dehydrogenase that catalyzes the conversion of acetone to isopropanol.

In some aspects, the disclosure is generally drawn to a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid.

In some aspects, the microorganism further comprises the deletion or inactivation of glcDEF. In some aspects, the microorganism further comprises the deletion or inactivation of dkgA. In some aspects, the microorganism further comprises the deletion or inactivation of yahK. In some aspects, the xylose symporter is controlled by a GAPDH promoter at the araFGH locus.

In some aspects, the C5 sugar symporter is a xylose symporter XylE. In some aspects, the XylE comprises an amino acid sequence comprising SEQ ID NO: 49. In some aspects, the XylE is encoded by a nucleic acid sequence comprising SEQ ID NO: 48. In some aspects, the xylose symporter is endogenous to the microorganism.

In some aspects, the C5 sugar symporter is an arabinose symporter AraE. In some aspects, the arabinose symporter is endogenous to the microorganism. In some aspects, uptake of the xylose is not sensitive to catabolic repression by other monosaccharides. In some aspects, the microorganism comprises a functional phosphotransferase system.

In some aspects, the microorganism comprises a native wild-type nucleic acid sequence encoding a cAMP receptor protein (CRP). In some aspects, the CRP comprises an amino acid sequence comprising SEQ ID NO: 10. In some aspects, the CRP is encoded by a nucleic acid sequence comprising SEQ ID NO: 9. In some aspects, the constitutive overexpression of the xylose symporter enables continuous import of xylose from the feedstock into the microorganism. In some aspects, the constitutive overexpression of the arabinose symporter enables continuous import of xylose from the feedstock into the microorganism. In some aspects, the continuous xylose import occurs independent of the presence of other sugars in the feedstock.

In some aspects, the recombinant microorganism comprises a pathway for glycolic acid production with one or more of the following from (c) and (e); (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylulokinases from the genome of a parent microorganism. In some aspects, (c) and (d) are in an operon controlled by the proD promoter. In some aspects, the proD promoter is encoded by a nucleic acid sequence comprising SEQ ID NO: 53.

In some aspects, the xylose isomerase is XylA. In some aspects, the XylA comprises an amino acid sequence comprising SEQ ID NO: 6. In some aspects, the XylA is encoded by a nucleic acid sequence comprising SEQ ID NO: 5. In some aspects, the xylose isomerase is endogenous to the microorganism.

In some aspects, the ketohexokinase is from *Homo Sapiens*. In some aspects, the ketohexokinase is heterologous to the microorganism. In some aspects, the ketohexokinase is khk-C. In some aspects, the khk-C comprises an amino acid sequence comprising SEQ ID NO: 12. In some aspects, the khk-C is encoded by a nucleic acid sequence comprising SEQ ID NO: 11.

In some aspects, the fructose-biphosphate aldolase is from *Homo Sapiens*. In some aspects, the fructose-biphosphate aldolase is aldoB. In some aspects, the aldoB comprises an amino acid sequence comprising SEQ ID NO: 51. In some aspects, the aldoB is encoded by a nucleic acid sequence comprising SEQ ID NO: 50. In some aspects, the fructose-biphosphate aldolase is heterologous to the microorganism.

In some aspects, the glycoaldehyde dehydrogenase is aldA. In some aspects, the aldA comprises an amino acid sequence comprising SEQ ID NO: 4. In some aspects, the aldA is encoded by a nucleic acid sequence comprising SEQ ID NO: 3. In some aspects, the glycoaldehyde dehydrogenase is endogenous to the microorganism.

In some aspects, the xylulokinase is XylB. In some aspects, the xylB comprises an amino acid sequence comprising SEQ ID NO: 14. In some aspects, the xylB is encoded by a nucleic acid sequence comprising SEQ ID NO: 13.

In some aspects, the recombinant microorganism comprises a pathway for glycolic acid production with one or more of the following from (c) through (e); (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylose isomerases and/or one or more xylulokinases from the genome of a parent microorganism. In some aspects, (c) and (d) are controlled by the proD promoter. In some aspects, the proD promoter is encoded by a nucleic acid sequence comprising SEQ ID NO: 53.

In some aspects, the xylose isomerase is XylA. In some aspects, the XylA comprises an amino acid sequence comprising SEQ ID NO: 6. In some aspects, the XylA is encoded by a nucleic acid sequence comprising SEQ ID NO: 5.

In some aspects, the xylulokinase is XylB. In some aspects, the xylB comprises an amino acid sequence comprising SEQ ID NO: 14. In some aspects, the xylB is encoded by a nucleic acid sequence comprising SEQ ID NO: 13.

In some aspects, the xylose dehydrogenase is from *Caulobacter crescentus, Burkholderia xenovorans, Haloferax volcanii*. In some aspects, the xylose dehydrogenase is xdh. In some aspects, the xdh comprises an amino acid sequence comprising SEQ ID NO: 16, 17 or 19. In some aspects, the xdh is encoded by a nucleic acid sequence comprising SEQ ID NO: 15, 18 or 97. In some aspects, the xylose dehydrogenase is heterologous to the microorganism.

In some aspects, the xylonolactonase is from *Caulobacter crescentus, Burkholderia xenovorans, Haloferax volcanii*. In some aspects, the xylonolactonase is xylC. In some aspects, the xylC comprises an amino acid sequence comprising SEQ ID NO: 55, 57 or 59. In some aspects, the xylC is encoded by a nucleic acid sequence comprising SEQ ID NO: 54, 56 or 58.

In some aspects, the xylonolactonase is heterologous to the microorganism. In some aspects, the xylonolactonase is endogenous to the microorganism.

In some aspects, the glycoaldehyde dehydrogenase is aldA. In some aspects, the aldA comprises an amino acid sequence comprising SEQ ID NO: 4. In some aspects, the aldA is encoded by a nucleic acid sequence comprising SEQ ID NO: 3. In some aspects, the glycoaldehyde dehydrogenase is endogenous to the microorganism.

In some aspects, the microorganism further expresses a pathway for the production of glycolic acid with one or more of the following: (f) expression of at least one endogenous or exogenous nucleic acid molecule encoding an isocitrate lyase; and/or (g) expression of at least one endogenous or exogenous nucleic acid molecule encoding a glyoxylate reductase. In some aspects, (f) and (g) are in an operon controlled by the OXB20 promoter. In some aspects, the OXB20 promoter is encoded by a nucleic acid sequence comprising SEQ ID NO: 96.

In some aspects, the isocitrate lyase is AceA. In some aspects, the AceA comprises an amino acid sequence comprising SEQ ID NO: 90. In some aspects, the AceA is encoded by a nucleic acid sequence comprising SEQ ID NO: 89.

In some aspects, the glyoxylate reductase is YcdW. In some aspects, the YcdW comprises an amino acid sequence comprising SEQ ID NO: 92. In some aspects, the YcdW is encoded by a nucleic acid sequence comprising SEQ ID NO: 91.

In some aspects, the recombinant microorganism is derived from a parental microorganism selected from the group consisting of *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp., *Corynebacterium* sp., *Yarrowia lipolytica, Scheffersomyces stipitis*, and0 *Terrisporobacter glycolicus*. In some aspects, the parental microorganism is *E. coli*.

In some aspects, the disclosure is generally drawn to a recombinant microorganism capable of producing a fermentation product from a feedstock comprising xylose and glucose, wherein the recombinant microorganism simultaneously utilizes xylose and glucose, and wherein the microorganism comprises one or more of the following: (a) deletion or inactivation of a pentose ATP-binding transporter proteins from the genome of the microorganism such that the transporter proteins are not expressed; (b) one or more endogenous or exogenous nucleic acid sequences encoding at least one of a C5 sugar symporter operatively linked to one or more constitutive promoters; wherein the C5 sugar symporter comprises: (1) a xylose symporter and/or a (2) an arabinose symporter; (c) one or more endogenous or exogenous nucleic acid sequences encoding (1) a xylose isomerase operatively linked to one or more constitutive promoters, and deletion or inactivation of one or more xylulokinases and/or (2) a xylose dehydrogenase operatively linked to one or more constitutive promoters and deletion or inactivation of one or more xylose isomerases and/or one or more xylulokinases. In some aspects, the fermentation product produced by the microorganism is one or more molecules comprising 1, 2, 3, 4, 5, 6, 7, 8, 9, or 10 carbons. In some aspects, the two or more molecules are produced simultaneously.

In some aspects, the disclosure is generally drawn to a recombinant *E. coli* capable of producing a fermentation product from a feedstock comprising xylose and glucose, wherein the recombinant microorganism simultaneously utilizes xylose and glucose, and wherein the microorganism comprises one or more of the following: (a) deletion or inactivation of ATP-binding transporter proteins araFGH and xylFGH from the genome of the microorganism such that the transporter proteins are not expressed; (b) one or more endogenous or exogenous nucleic acid sequences encoding at least one of a C5 sugar symporter operatively linked to one or more constitutive promoters; wherein the C5 sugar symporter comprises: (1) a xylose symporter and/or a (2) an arabinose symporter; (c) one or more endogenous or exogenous nucleic acid sequences encoding (1) a xylose isomerase operatively linked to one or more constitutive promoters and deletion or inactivation of one or more xylulokinases and/or (2) a xylose dehydrogenase operatively linked to one or more constitutive promoters and deletion or inactivation of one or more xylose isomerases and/or one or more xylulokinases.

In some aspects, the disclosure is generally drawn to a recombinant microorganism capable of producing monoethylene glycol (MEG) and/or acetone from a feedstock comprising xylose and glucose, wherein the recombinant microorganism simultaneously utilizes xylose and glucose, comprising one or more of the following: (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism expresses pathways for MEG and/or acetone production.

In aspects, the microorganism further comprises the deletion or inactivation of glcDEF. In some aspects, the C5 symporter is controlled by a GAPDH promoter at the araFGH locus. In some aspects, the C5 sugar symporter is a xylose symporter XylE. In some aspects, the xylose symporter is endogenous to the microorganism. In some aspects, the C5 sugar symporter is an arabinose symporter AraE. In some aspects, the arabinose symporter is endogenous to the microorganism. In some aspects, the uptake of the xylose is not sensitive to catabolic repression by other monosaccharides. In some aspects, the microorganism comprises a functional phosphotransferase system. In some aspects, the microorganism comprises a native wild-type nucleic acid sequence encoding a cAMP receptor protein (CRP). In some aspects, the one or more nucleic acid molecules encoding the aldA comprises a nucleic acid sequence set forth in SEQ ID NO: 3. In some aspects, the one or more amino acid sequences encoding the aldA comprises an amino acid sequence set forth in SEQ ID NO: 4. The recombinant microorganism of claim 5, wherein the constitutive overexpression of the xylose symporter enables continuous import of xylose from the feedstock into the microorganism. The recombinant microorganism of claim 5, wherein the constitutive overexpression of the arabinose symporter enables continuous import of xylose from the feedstock into the microorganism. The recombinant microorganism of claim 5, wherein the continuous xylose import occurs independent of the presence of other sugars in the feedstock.

In some aspects, the recombinant microorganism comprises a pathway for MEG production with one or more of the following from (c) through (e); (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylulokinases from the genome of a parent microorganism.

In some aspects, (c) and (d) are in an operon controlled by the proD promoter. In some aspects, the xylose isomerase is XylA. In some aspects, the xylose isomerase is endogenous to the microorganism. In some aspects, the ketohexokinase is from *Homo Sapiens*. In some aspects, the ketohexokinase is heterologous to the microorganism. In some aspects, the fructose-biphosphate aldolase is from *Homo Sapiens*. In some aspects, the fructose-biphosphate aldolase is heterologous to the microorganism. In some aspects, the glycoaldehyde reductase is endogenous to the microorganism. In some aspects, the glycoaldehyde reductase is fucO. In some aspects, the xylulokinase is XylB.

In some aspects, the recombinant microorganism comprises a pathway for MEG production with one or more of the following from (c) through (e); (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylose isomerases and/or one or more xylulokinases from the genome of a parent microorganism.

In some aspects, the xylose dehydrogenase is from *Caulobacter crescentus, Burkholderia xenovorans, Haloferax volcanii*. In some aspects, the xylose dehydrogenase is heterologous to the microorganism. In some aspects, the xylonolactonase is from *Caulobacter crescentus, Burkholderia xenovorans, Haloferax volcanii*. In some aspects, the xylonolactonase is heterologous to the microorganism. In some aspects, the xylonolactonase is endogenous to the microorganism. In some aspects, the xylose dehydratase is from *Caulobacter crescentus, Burkholderia xenovorans, Haloferax volcanii*.

In some aspects, the xylose dehydratase is heterologous to the microorganism. In some aspects, the xylose dehydratase is endogenous to the microorganism. In some aspects, the glycoaldehyde reductase is endogenous to the microorganism. In some aspects, the glycoaldehyde reductase is fucO. In some aspects, the glycoaldehyde reductase is heterologous to the microorganism. In some aspects, the xylose isomerase is XylA. In some aspects, the xylulokinase is XylB.

In some aspects, the recombinant microorganism further comprises a pathway for acetone production with one or more of the following from (f) to (h); (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone. In some aspects, (f), (g) and (h) are in an operon controlled by the OXB11 promoter.

In some aspects, the acetoacetyl-CoA thiolase is from *Clostridium acetobutylicum*. In some aspects, the acetate:acetoacetyl-CoA transferase is a AtoDA. In some aspects, the acetoacetate decarboxylase is from *Clostridium beijerinckii*.

In some aspects, the recombinant microorganism further comprises a pathway for isopropanol production with one or more of the following from (f) to (i); (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone. (i) expression of at least one exogenous nucleic acid molecule encoding an alcohol dehydrogenase that catalyzes the conversion of acetone to isopropanol.

In some aspects, the disclosure is generally drawn to a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid. In some aspects, the microorganism further comprises the deletion or inactivation of glcDEF. In some aspects, the microorganism further comprises the deletion or inactivation of dkgA. In some aspects, the microorganism further comprises the deletion or inactivation of yahK. In some aspects, the xylose symporter is controlled by a GAPDH promoter at the araFGH locus. In some aspects, the C5 sugar symporter is a xylose symporter XylE. In some aspects, the xylose symporter is endogenous to the microorganism. In some aspects, the C5 sugar symporter is a arabinose symporter AraE. In some aspects, the arabinose symporter is endogenous to the microorganism. In some aspects, the uptake of the xylose is not sensitive to catabolic repression by other monosaccharides.

In some aspects, the microorganism comprises a functional phosphotransferase system. In some aspects, the microorganism comprises a native wild-type nucleic acid sequence encoding a cAMP receptor protein (CRP). In some aspects, the one or more nucleic acid molecules encoding the CRP comprises a nucleic acid sequence set forth in SEQ ID NO: 9. In some aspects, the one or more amino acid sequences encoding the CRP comprises an amino acid sequence set forth in SEQ ID NO: 10. In some aspects, the constitutive overexpression of the xylose symporter enables continuous import of xylose from the feedstock into the microorganism. In some aspects, the constitutive overexpression of the arabinose symporter enables continuous import of xylose from the feedstock into the microorganism. In some aspects, the continuous xylose import occurs independent of the presence of other sugars in the feedstock.

In some aspects, the recombinant microorganism comprises a pathway for glycolic acid production with one or more of the following from (c) and (e): (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylulokinases from the genome of a parent microorganism. In some aspects, (c) and (d) are in an operon controlled by the proD promoter.

In some aspects, the xylose isomerase is XylA. In some aspects, the xylose isomerase is endogenous to the microorganism. In some aspects, the ketohexokinase is from *Homo Sapiens*. In some aspects, the ketohexokinase is heterologous to the microorganism. In some aspects, the fructose-biphosphate aldolase is from *Homo Sapiens*. In some aspects, the fructose-biphosphate aldolase is heterologous to the microorganism. In some aspects, the glycoaldehyde dehydrogenase is aldA. In some aspects, the glycoaldehyde dehydrogenase is endogenous to the microorganism. In some aspects, the xylulokinase is XylB.

In some aspects, the recombinant microorganism comprises a pathway for glycolic acid production with one or more of the following from (c) through (e): (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylose isomerases and/or one or more xylulokinases from the genome of a parent microorganism. In some aspects, (c) and (d) are controlled by the proD promoter.

In some aspects, the xylose isomerase is XylA. In some aspects, the xylulokinase is XylB. In some aspects, the xylose dehydrogenase is from *Caulobacter crescentus. Burkholderia xenovorans, Haloferax volcanii*. In some aspects, the xylose dehydrogenase is heterologous to the microorganism. In some aspects, the xylonolactonase is from *Caulobacter crescentus, Burkholderia xenovorans, Haloferax volcanii*. In some aspects, the xylonolactonase is heterologous to the microorganism. In some aspects, the xylonolactonase is endogenous to the microorganism. In some aspects, the glycoaldehyde dehydrogenase is aldA. In some aspects, the glycoaldehyde dehydrogenase is endogenous to the microorganism.

In some aspects, the microorganism further expresses a pathway for the production of glycolic acid with one or more of the following: (f) expression of at least one endogenous or exogenous nucleic acid molecule encoding an isocitrate lyase; and/or (g) expression of at least one endogenous or exogenous nucleic acid molecule encoding a glyoxylate reductase. In some aspects, (f) and (g) are in an operon controlled by the OXB20 promoter. In some aspects, the isocitrate lyase is AceA. In some aspects, the glyoxylate reductase is YcdW.

In some aspects, the recombinant microorganism is derived from a parental microorganism selected from the group consisting of *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp., *Corynebacterium* sp., *Yarrowia lipolytica, Scheffersomyces stipitis,* and *Terrisporobacter glycolicus*.

DETAILED DESCRIPTION OF THE DISCLOSURE

Figure 1:
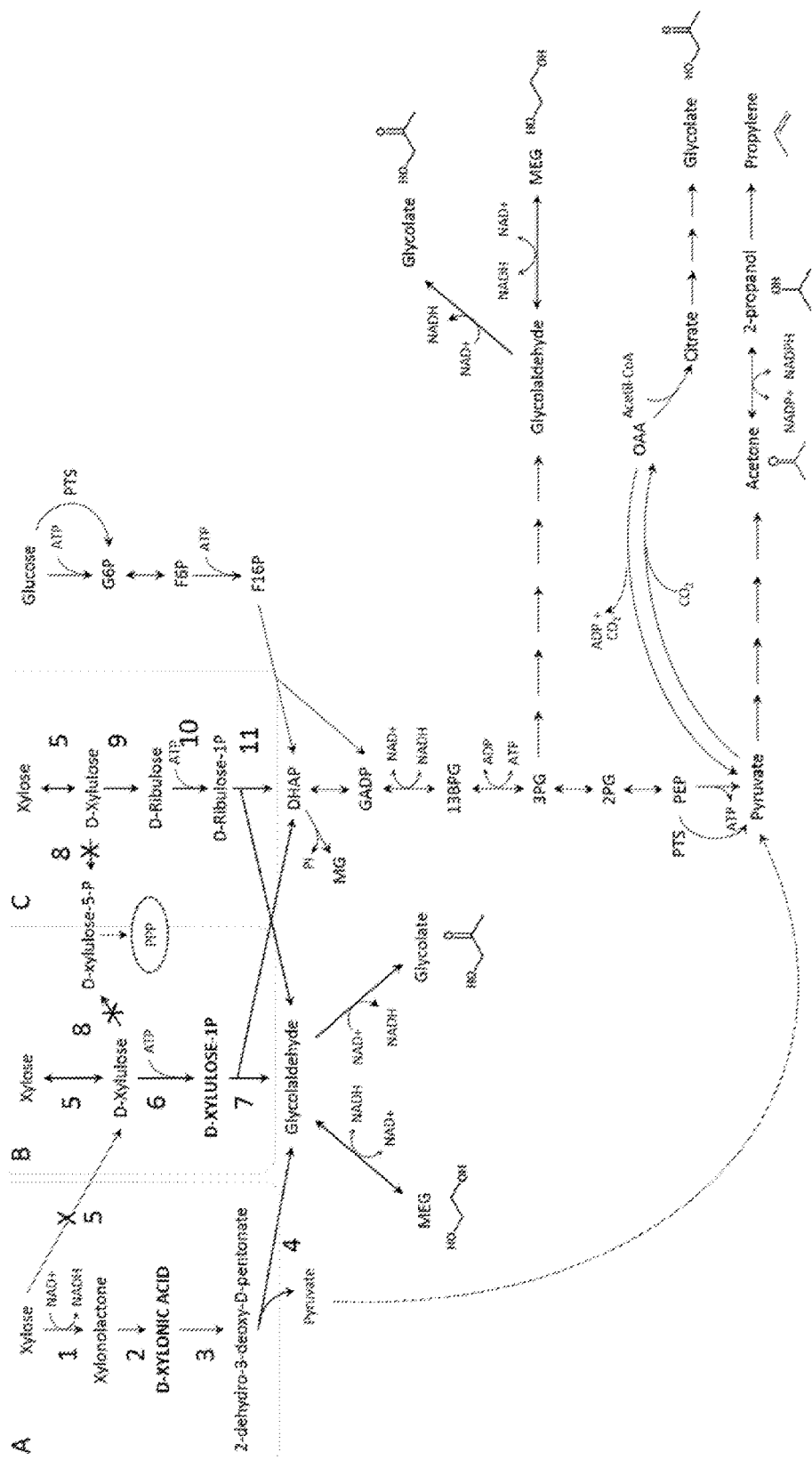
FIG. 1 depicts multiple pathways utilizing xylose and glucose to produce products contemplated herein.

The present disclosure is generally drawn to the engineering of microbes to maximize the production of desirable products from biorenewable plant feedstocks that would ordinarily be incapable of achieving anything approaching a maximal yield and productivity due to the repression effects of multiple carbon sources present in a single type of feedstock. The present disclosure sets forth methods and compositions for reducing or eliminating the repression effects stemming from the co-consumption of some monosaccharides, which result in a microbes that are not operating at maximal productivity.

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scoreable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one aspect, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one aspect, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting aspect, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some aspects, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some aspects, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

As used herein the terms "microorganism" or "microbe" should be taken broadly. These terms, used interchangeably, include but are not limited to, the two prokaryotic domains, Bacteria and Archaea.

As used herein, "isolate," "isolated," "isolated microbe," and like terms, are intended to mean that the one or more microorganisms has been separated from at least one of the materials with which it is associated in a particular environment (for example media, water, reaction chamber, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be a commercially or industrial acceptable carrier.

In certain aspects of the disclosure, the isolated microbes exist as "isolated and biologically pure cultures." It will be appreciated by one of skill in the art, that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970)(discussing purified prostaglandins), see also, In re Bergy, 596 F.2d 952 (CCPA 1979) (discussing purified microbes), see also, Parke-Davis & Co. v. H. K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain aspects, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

Microbes of the present disclosure may include spores and/or vegetative cells. In some aspects, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, stored, or transferred, which does not detrimentally effect the microbe.

The term "yield potential" as used herein refers to a yield of a product from a biosynthetic pathway. In one aspect, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway.

If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one aspect, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide (NAD+), which then contributes to the creation of a proton gradient, which drives the synthesis of adenosine triphosphate (ATP) and is maintained by the reduction of oxygen. The term redox state is often used to describe the balance of GSH/GSSG, NAD+/NADH and NADP+/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

As used herein, the term "productivity" refers to the total amount of bioproduct produced per hour-gram of product/(liter per hour).

As used herein, the term "substantially free of microorganisms," "substantially free of bacteria", or "substantially free of fungi/yeasts" should not be construed to mean that no microorganisms/bacteria/fungi/yeasts are present, although this may be preferred in some aspects. Rather, "substantially free" should be construed to mean that, as an example, a composition substantially free of bacteria is a composition in which any bacteria that are present in the composition are so few that they fall below the detection limit. In some aspects, the microorganisms are selected from one or more bacteria, fungi, yeasts, viruses, protists, and algae.

As used herein, the term "free of microorganisms" refers to either the complete absence of microorganisms or the complete absence of viable microorganisms capable of vegetative growth of reproduction.

Simultaneous Consumption of Xylose and Glucose

In industrial or commercial processes, the microbial productivity is a critical factor that must be taken into consideration when considering the economic viability of large-scaled reactions that often have razor thin margins. Microbial productivity, in this sense is the gram of product produced per liter per hour. In the absence of modified microbes, a stream containing both xylose and glucose constantly fed into a reaction chamber(s) will likely result in uptake repression of one or more monosaccharides by at least glucose.

The underlying mechanism for diauxic growth is carbon catabolite repression (CCR), in which the global transcriptional regulator CRP (cAMP receptor protein) plays a central role in modulating transcriptional activation of catabolic operons for secondary sugars such as xylose arabinose, and galactose. The phosphoenolpyruvate: sugar phosphotransferase system (PTS) is also involved in glucose-induced repression of xylose utilization in *E. coli*. Xylose can be utilized by *E. coli* as a sole carbon and energy source, and is metabolized through the pentose phosphate pathway. Xylose can be imported by two uptake systems: high-affinity ATP-dependent system and the relatively low-affinity D-xylose:H+ symporter. Unlike for arabinose transport which is primarily transported through the more energy-efficient symporter, xylose is primarily transported through the more-energy-costly ATP-dependent transporter, even at high sugar concentrations. All genes responsible for uptake and catabolism of xylose are sensitive to CCR.

In order to have an effective bioprocess for conversion of pentoses into desirable chemicals, it is necessary to engineer the host microbe for efficient, simultaneous, and rapid utilization of mixed sugars to reach yields and productivities needed for an industrial process. The present disclosure sets forth a metabolic engineering strategy to efficiently promote simultaneous consumption of xylose and glucose from lignocellulosic biomass, and consequently access full potential of the engineered microbial strain for desirable chemicals derived from pathways that have D-xylonate or D-xylulose-1P or glycolaldehyde as intermediates.

Common strategies for engineering sugar co-utilization in *E. coli* relies on the inactivation of PTS components which may or may not be associated with improvements in galP (galactose:H+ symporter) activity and mutagenesis of CRP. However, inactivation of PTS components impairs glucose uptake and CRP mutants often have slow growth phenotypes potentially due to unpredictable changes in expression of other important genes. These two approaches result in decreases in productivity, particularly for conditions of high sugar concentrations and low-cost media.

Applicant believes that it is the first to develop a metabolic engineering strategy to support glucose and xylose co-consumption for production of desirable chemicals having D-xylulose-1P or D-xylonate or glycolaldehyde as intermediates that are independent of PTS inactivation and have the deletion of ATP-binding transporters.

In some aspects, the promotion of simultaneous consumption of xylose and glucose for production of desirable chemicals is based upon: (1) constitutive overexpression of ATP-independent D-xylose symporters; (2) constitutive expression of genes for the conversion of xylose into D-xylulose-1P or D-xylonate; (3) deletion of native pentose (mainly xylose and arabinose) ABC transporter systems; and/or deletion of xylose catabolism genes.

The subject matter described herein is distinguished over the state of the art in that the deletion or inactivation of the ABC transporters and the expression of the symporters and pathways utilizing or comprising D-xylulose, D-xylonate, or glycolaldehyde as intermediates not only positively effects the sugar co-utilization, but also increases the overall yield and productivity of a pathway for the production of desirable chemicals. This improvement is due to the modulation of the overall metabolism of the microbe, modification of the ATP availability profile, and furthering the production of the intermediates, D-xylulose-1P, D-xylonate, and/or glycolaldehyde. See Kim et al. (2015. *Metabolic Engineering*, 30:141-148), Sievert et al. (2017. *PNAS*, 114(28):7349-7354), Wang et al. (2018. *Microbial Cell Factories*, 17(12):1-12), and Bai et al. (2016. *Metabolic Engineering*, 38:285-292).

The present disclosure comprises a strategy of overcoming the catabolic repression of glucose on xylose, allowing for both sugars to be simultaneously consumed. Unlike other approaches for co-consumption of sugars, the present strategy was designed and implemented to focus on assuring an efficient xylose uptake that is not sensitive to catabolic repression by sugars, while keeping the efficient uptake of glucose by the native PTS system.

In some aspects, the instant methods comprise making the following modifications in a microbial strain of interest: 1(a) overexpressing the native xylose symporter XylE operatively linked to a constitutive promoter, and/or 1(b) overexpressing the native arabinose symporter AraE operatively linked to a constitutive promoter; 2(a) expressing the native xylose isomerase XylA and a heterologous ketohexokinase khk-C under a constitutive promoter and deletion or inactivation of the native xylulokinase XylB, or 2(b) expressing the heterologous xylose dehydrogenase xdh operatively linked to a constitutive promoter and deletion or inactivation of the native xylose isomerase XylA and/or deletion of the native xylulokinase XylB; and 3 the deletion of ATP-binding transporter proteins AraFGH, XylFGH, RbsABC, and AlsABC.

In some aspects, the constitutive expression of xylose and arabinose symporters enables xylose import independent of CRP regulation, and consequently, independent of other sugars present in the culture broth. In some aspects, the constitutive expression of xylose isomerase enables the xylose utilization independent of CRP regulation, and consequently, also independent of other sugars present in the culture broth. In some aspects, the expression of ketohexokinase khk-C efficiently converts D-xylulose into D-xylulose 1-P, an intermediate for the production of desirable chemicals. In some aspects, the deletion of xylulokinase prevents the diversion of carbon from the pathway for chemical production to the native Pentose Phosphate Pathway.

In some aspects, the constitutive expression of xylose dehydrogenase enables the xylose utilization independent of CRP regulation, and consequently, also independent of other sugars presented in the culture broth; and also efficiently convert D-xylose into D-xylonate, an intermediate for the production of desirable chemicals. In some aspects, the deletion of xylulokinase and/or xylose isomerase prevents the diversion of carbon from the pathway for chemical production to the native Pentose Phosphate Pathway. In some aspects, the deletion of ATP-binding cassette transporters such as the arabinose ABC transporter and the xylose ABC transporter avoids ATP loss during sugar import. The net amount of ATP can change the activity of the central metabolism of *E. coli*, potentially increasing the pathway yield.

Overexpression of the Native Xylose Symporter XylE Under a Constitutive Promoter The D-xylose/proton symporter XylE is an ATP-independent low-affinity transporter, a member of the major facilitator superfamily (MFS) of transporters, encoded by the xylE gene. Transcription of xylE is believed to be regulated by XylR (SEQ ID NO: 7 or SEQ ID NO: 8). XylR is a transcription factor, encoded by the xylR gene, which positively regulates the transcription of the xylose metabolic and transporter genes in response to xylose (xylE, xylFGH, and xylAB genes).

The constitutive overexpression of the xylose symporter releases carbon catabolic repression and enables continuous xylose import, independent of the sugars present in the culture broth, while the glucose uptake will still be performed by PTS system components. Therefore, both glucose and xylose present in hydrolysates can be imported simultaneously by *E. coli*.

Overexpression of the Native Arabinose Symporter AraE Under a Constitutive Promoter The D-arabinose/proton symporter AraE is an ATP-independent low-affinity transporter, a member of the major facilitator superfamily (MFS) of transporters encoded by the araE gene. Transcription of araE is regulated by AraC (SEQ ID NO: 32 and SEQ ID NO: 33) and CRP. AraC is a transcription factor, encoded by the araC gene, which negatively regulates the transcription of the xylose metabolic and transporter genes in response to arabinose (xylE, xylFGH, and xylAB genes) and positively regulates the transcription of the arabinose metabolic and transporter genes in response to arabinose (araE, araFGH, and araBAD genes). araE expression is induced by arabinose in the absence of glucose. It is known that the AraE transporter is promiscuous and able to transport xylose and other pentoses.

The constitutive expression of a promiscuous arabinose symporter releases CCR and enables continuous xylose import, independent of the sugars present in the culture broth, while the glucose uptake is still performed by the PTS system components. Therefore, both glucose and xylose present in the hydrolysate can be imported simultaneously by *E. coli*.

Expression of Native Xylose Isomerase XylA and a Heterologous Ketohexokinase Khk-C Under Constitutive Promoters, and the Deletion of the Native Xylulokinase XylB XylA is an endogenous D-xylose isomerase (FIG. 1, reaction 5, pathway B) that catalyzes the conversion of D-xylose into D-xylulose. D-xylose isomerase (E.C. 5.3.1.5) catalyzes the first reaction in the *E. coli* native catabolism of D-xylose. Transcription of xylA is regulated by XylR and CRP; its expression is induced by xylose in the absence of glucose. The ketohexokinase (FIG. 1, reaction 6, pathway B) catalyzes the phosphorylation of D-xylulose to D-xylulose-1-P. Ketohexokinases (E.C. 2.7.1.3) can be found in a variety of organisms, however khk-C from human liver is a promising candidate for activity on xylulose. D-xylulose 1-P is a key intermediate for the production of a variety of chemicals.

XylB is a xylulose kinase (2.7.1.17) encoded by xylB that catalyzes the phosphorylation of D-xylulose (FIG. 1, reaction 8, pathway B). This is the second step in the native xylose degradation pathway that produces D-xylulose-5-phosphate, an intermediate of the pentose phosphate pathway. This reaction competes with the phosphorylation of the D-xylulose by khk-C, deviating the flux from D-xylulose-1-P production to the Pentose Phosphate Pathway.

The constitutive expression of native xylose isomerase xylA releases CCR and, when associated with constitutive heterologous expression of a ketohexokinase khk-C enables continuous xylose utilization, independent of the sugars present in the culture broth and yield D-xylulose 1-P as intermediate to produce chemicals. The glucose uptake will still be performed by PTS system components. Therefore, both glucose and xylose present in hydrolysates can be utilized simultaneously by *E. coli*. The deletion of xylulokinase xylB will prevent the diversion of carbon from the pathway for chemical production to the native Pentose Phosphate Pathway.

Expression of Heterologous Xylose Dehydrogenase Xdh Under a Constitutive Promoter and Deletion of the Native Xylose Isomerase Xyla and/or Deletion of the Native Xylulokinase XylB xdh, a heterologous xylose dehydrogenase, catalyzes the conversion of D-xylose to D-xylonolactone (FIG. 1, reaction 1, pathway A). D-xylose dehydrogenase (E.C. 1.1.1.175) can be found in a variety of organisms; however, xdh from *Caulobacter crescentus* is a candidate for activity on D-xylose. D-xylonolactone could be spontaneously converted to D-xylonic acid, so the expression of xdh on xylose yields D-xylonic acid, a key intermediate for the production of a variety of chemicals.

XylA, a D-xylose isomerase (E.C. 5.3.1.5) encoded by xylA, catalyzes the conversion of D-xylose to D-xylulose (FIG. 1, reaction 5, pathway A), an intermediate of the pentose phosphate pathway. XylB, a xylulose kinase (2.7.1.17) encoded by xylB, catalyzes the phosphorylation of D-xylulose (FIG. 1, reaction 8, pathway A), the second step in the xylose degradation pathway, producing D-xylulose-5-phosphate, another intermediate of the pentose phosphate pathway. Both reactions compete with xdh, deviating the flux from D-xylonic acid production to the Pentose Phosphate Pathway.

The constitutive heterologous expression of a xylose dehydrogenase enables the continuous xylose utilization, independent of the sugars present in the culture broth, and yields D-xylonic acid as an intermediate to produce the desirable chemicals. The glucose uptake will still be performed by PTS system components. Therefore, both glucose and xylose present in hydrolysates can be utilized simultaneously by the *E. coli*. The deletion of D-xylose isomerase and/or xylulokinase will prevent the diversion of carbon from the pathway for chemical production to the native Pentose Phosphate Pathway.

Deletion of ATP-Binding Cassette Transporter Proteins AraFGH, XylFGH, RbsABC, and AlsABC Arabinose ABC transporter AraFGH (E.C. 3.6.3.17, TCDB 3.A.1.2.2) is a high affinity ATP-driven system encoded by the araFGH genes. The AraF is a periplasmic binding protein, AraH is the membrane component and AraG is the ATP-binding component of this ABC transporter. Transcription of the araFGH operon is regulated by AraC and CRP. araFGH expression is induced by arabinose in the absence of glucose. It is known that the AraFGH transporter is promiscuous and able to transport xylose and other pentoses.

Xylose ABC transporter XylFGH (E.C. 3.6.3.17, TCDB 3.A.1.2.4) is a high affinity ATP-driven system encoded by the xylFGH genes. The XylF is a periplasmic binding protein, XylH is the membrane component and XylG is the ATP-binding component of this ABC transporter. Transcription of xylFGH operon is regulated by XylR and CRP; its expression is induced by xylose in the absence of glucose.

Ribose ABC transporter RbsABC (E.C. 3.6.3.17; TCDB 3.A.1.2.1) is a high affinity ATP-driven system encoded by the rbsABC genes.

In some aspects, the one or more nucleic acid molecules encoding the RbsB periplasmic binding protein subunit of RbsABC comprises a nucleic acid sequence set forth in SEQ ID NO: 35. In some aspects, the one or more amino acid sequences encoding the RbsB periplasmic binding protein subunit of RbsABC comprises an amino acid sequence set forth in SEQ ID NO:38. In some aspects, the one or more nucleic acid molecules encoding the RbsA ATP-binding subunit of RbsABC comprises a nucleic acid sequence set forth in SEQ ID NO: 34. In some aspects, the one or more amino acid sequences encoding the RbsA ATP-binding subunit of RbsABC comprises an amino acid sequence set forth in SEQ ID NO:37. In some aspects, the one or more nucleic acid molecules encoding the RbsC membrane subunit of RbsABC comprises a nucleic acid sequence set forth in SEQ ID NO: 36. In some aspects, the one or more amino acid sequences encoding the RbsC membrane subunit of RbsABC comprises an amino acid sequence set forth in SEQ ID NO: 39.

Allose ABC transporter AlsABC (E.C. 3.6.3.17; TCDB 3.A.1.2.6) is an ATP-driven system encoded by the alsABC genes.

In some aspects, the one or more nucleic acid molecules encoding the alsB periplasmic binding protein subunit of AlsABC comprises a nucleic acid sequence set forth in SEQ ID NO: 41. In some aspects, the one or more amino acid sequences encoding the alsB periplasmic binding protein subunit of AlsABC comprises an amino acid sequence set forth in SEQ ID NO: 44. In some aspects, the one or more nucleic acid molecules encoding the alsA ATP-binding subunit of AlsABC comprises a nucleic acid sequence set forth in SEQ ID NO: 40. In some aspects, the one or more amino acid sequences encoding the alsA ATP-binding subunit of AlsABC comprises an amino acid sequence set forth in SEQ ID NO: 43. In some aspects, the one or more nucleic acid molecules encoding the alsC membrane subunit of AlsABC comprises a nucleic acid sequence set forth in SEQ ID NO: 42. In some aspects, the one or more amino acid sequences encoding the alsC membrane subunit of AlsABC comprises an amino acid sequence set forth in SEQ ID NO: 45.

The deletion of ATP-binding cassette transporters such as the ribose ABC transporter, allose ABC transporter, arabinose ABC transporter, and the xylose ABC transporter, which include the preferential xylose transporters in *E. coli*, in association with xylE constitutive expression (See Examples 1 and 2), releases CCR and enables continuous xylose import. Furthermore the deletion will avoid ATP loss during sugar import. The ATP net can change the activity of the central metabolism of *E. coli*.

Microbes

As described herein, in some aspects, recombinant microorganisms are capable of utilizing both xylose and glucose simultaneously.

As described herein, in some aspects, the recombinant microorganisms are prokaryotic microorganisms. In some aspects, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, Micrococcus, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

In some aspects, the microorganisms of the present disclosure are fungi.

In some aspects, the recombinant microorganism is a eukaryotic microorganism. In some aspects, the eukaryotic microorganism is a yeast. In exemplary aspects, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula,* and Myxozyma.

In some aspects, the recombinant microorganism is a prokaryotic microorganism. In exemplary aspects, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some aspects, microorganism for use in the methods of the present disclosure can be selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula, Myxozyma, Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium,* and *Brevibacterium.*

In some aspects, a microbe resulting from the methods described herein may be a species selected from any of the following genera: *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Actinomyces, Bacillus, Clostridium, Corynebacterium, Erysipelothrix, Lactobacillus, Listeria, Mycobacterium, Myxococcus, Nocardia, Staphylococcus, Streptococcus, Streptomyces, Saccharomyces, Pichia,* and *Aspergillus.*

In some aspects, microorganisms for use in the methods of the present disclosure include *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp, *Corynebacterium* sp., *Yarrowia lipolytica, Scheffersomyces stipitis,* and *Terrisporobacter glycolicus.*

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

Culturing of the microorganisms used in the methods of the disclosure may be conducted using any number of processes known in the art for culturing and fermenting substrates using the microorganisms of the present disclosure.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioreactor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. In some aspects, the bioreactor comprises a first, growth reactor in which the microorganisms are cultured, and a second, fermentation reactor, to which fermentation broth from the growth reactor is fed and in which most of the fermentation product is produced. In some aspects, the bioreactor simultaneously accomplishes the culturing of microorganism and the producing the fermentation product from carbon sources such substrates and/or feedstocks provided.

Products

In some aspects, engineered microbes of the present disclosure produce a fermentation product from a feedstock comprising xylose and glucose, wherein the recombinant microorganism simultaneously utilizes xylose and glucose. In some aspects the fermentation product produced by the microorganism comprises one or more molecules comprising at least 1, at least 2 at least 3, at least 4, at least 5, at least 6, at least 7, at least 8, at least 9, or at least 10 carbons.

In some aspects, engineered microbes of the present disclosure are capable of producing desirable chemicals such as monoethylene glycol, glycolic acid, C3 compounds (such as acetone, isopropanol and propene), amino acids, and polyols. See Koch et al. (WO2017156166A1) and Mcbride et al. (WO2011022651A1).

In some aspects, engineered microbes of the present disclosure are capable of producing desirable chemicals at a maximal yield due to the absence of the repression effects of multiple carbon sources present in a single type of feedstock.

Genetic Modifications

The genetic modification introduced into one or more microbes of the present disclosure may alter or abolish a regulatory sequence of a target gene. In some aspects, the genetic modification introduced into one or more microbes of the present disclosure may introduce a new trait or phenotype into the one or more microbes. One or more regulatory sequences may also be inserted, including heterologous regulatory sequences and regulatory sequences found within a genome of an animal, plant, fungus, yeast, bacteria, or virus corresponding to the microbe into which the genetic variation is introduced. Moreover, regulatory sequences may be selected based on the expression level of a gene in a microbial culture. The genetic variation may be a pre-determined genetic variation that is specifically introduced to a target site. In some aspects the genetic variation is a nucleic acid sequence that is introduced into one or more microbial chromosomes. In some aspects, the genetic variation is a nucleic acid sequence that is introduced into one or more extrachromosomal nucleic acid sequence. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of desired modifications in the microbes.

In some aspects, the genetic modification is a deletion or inactivation of a target gene or regulatory sequence. In some aspects, the deletion is a removal of the target gene or a substantial portion of the target gene. In some aspects, the deletion is a replacement of the target gene or a substantial portion of the target gene. In further aspects, the deletion results in a complete loss of function of the target gene. In some aspects, the deletion results in a partial loss of function of the target gene. In some aspects, the loss of function or partial loss of function is determined by comparing the activity of the modified target gene sequence with the activity of an unmodified target gene sequence. In some aspects, the inactivation of the target gene is the result of deleting or disrupting one or more regulatory or control sequence(s) operably linked to the target sequence. In some aspects, the inactivation of the target gene is the result of disrupting the target gene with a heterologous sequence. In some aspects, the inactivation results in a partial loss of function of the target gene. In some aspects, the inactivation results in a complete loss of function of the target gene.

In some aspects, one or more of the substrates set forth in the production of desirable chemicals are biosynthesized from a carbon feedstock (e.g., xylose and glucose).

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethyl sulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like).

Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some aspects, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some aspects, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some aspects, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for assessing conferral of an improved trait.

A CRISPR nuclease may be used as the site-specific nuclease to direct cleavage to a target site. An improved selection of mutated microbes can be obtained by using Cas9 to kill non-mutated cells. Microbes can then be re-isolated from tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-Ppol, I-SceIII, I-CreI, I-TeeI, I-TevII and I-TevIII.

In some aspects, the microorganisms are recombinant microorganisms. In some aspects, the microorganisms have been genetically modified to produce monoethylene glycol. In some aspects, the microorganisms have been genetically modified to produce one or more three-carbon compounds, such as acetone, isopropanol, and propene. In some aspects, the microorganisms have been genetically modified to co-produce monoethylene glycol and one or more three-carbon compounds. In some aspects, the microorganisms have been genetically modified with microbial biosynthetic pathways for producing one or more of monoethylene glycol, acetone, isopropanol, and propene. See Koch et al. (WO2017156166A1) pertaining to the state of the art for engineering microbes to produce one or more of monoethylene glycol, acetone, isopropanol, and propene from a renewable feedstock.

In some aspects, the microorganisms have been genetically modified with the introduction of the xylonate pathway. In some aspects, the microorganisms have been genetically modified with the introduction of the xylulose phosphate pathway. In some aspects, the microorganisms have been genetically modified with the introduction of the ribulose phosphate pathway. See Koch et al.

Recombinant Microorganisms Capable of Producing a Fermentation Product from a Feedstock Comprising Xylose and Glucose, Wherein the Recombinant Microorganism Simultaneously Utilizes Xylose and Glucose In some aspects, the recombinant microorganism comprises one or more of the following: (a) deletion or inactivation of pentose ATP-binding transporter proteins from the genome of the microorganism such that the transporter proteins are not expressed; (b) one or more endogenous or exogenous nucleic acid sequences encoding at least one of a C5 sugar symporter operatively linked to one or more constitutive promoters; wherein the C5 sugar symporter comprises: (1) a xylose symporter and/or a (2) an arabinose symporter; (c) one or more endogenous or exogenous nucleic acid sequences encoding (1) a xylose isomerase operatively linked to one or more constitutive promoters, and deletion or inactivation of one or more xylulokinases and/or (2) a xylose dehydrogenase operatively linked to one or more constitutive promoters and deletion or inactivation of one or more xylose isomerases and/or one or more xylulokinases. In some aspects, the C5 sugar symporter is a symporter protein capable of transporting 5-carbon sugars. In some aspects, the 5-carbon sugar can be, but not limited to, xylose, arabinose, or ribose.

General Production of MEG and/or Acetone

In some aspects, the recombinant microorganism comprises (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism expresses pathways for MEG and/or acetone production.

In some aspects, the microorganism further comprises the deletion or inactivation of glycolate dehydrogenase glcDEF. In some aspects, the C5 symporter is controlled by a GAPDH promoter at the araFGH locus. In some aspects, the one or more nucleic acid molecules encoding the GAPDH promoter comprises a nucleic acid sequence set forth in SEQ ID NO: 95. In some aspects, the C5 sugar symporter is a xylose symporter XylE. In some aspects, the one or more nucleic acid molecules encoding the XylE comprises a nucleic acid sequence set forth in SEQ ID NO: 48. In some aspects, the one or more amino acid sequences encoding the XylE comprises an amino acid sequence set forth in SEQ ID NO: 49. In some aspects, the xylose symporter is endogenous to the microorganism. In some aspects, the C5 sugar symporter is an arabinose symporter AraE. In some aspects, the arabinose symporter is endogenous to the microorganism. In some aspects, the one or more nucleic acid molecules encoding the AraE comprises a nucleic acid sequence set forth in SEQ ID NO: 46. In some aspects, the one or more amino acid sequences encoding the AraE comprises an amino acid sequence set forth in SEQ ID NO: 47. In some aspects, the xylose is not sensitive to catabolic repression by other monosaccharides.

In some aspects, the microorganism comprises a functional phosphotransferase system. In some aspects, the microorganism comprises a native wild-type nucleic acid sequence encoding a cAMP receptor protein (CRP). In some aspects, the one or more nucleic acid molecules encoding the CRP comprises a nucleic acid sequence set forth in SEQ ID NO: 9. In some aspects, the one or more amino acid sequences encoding the CRP comprises an amino acid sequence set forth in SEQ ID NO: 10. In some aspects, the constitutive overexpression of the xylose symporter enables continuous import of xylose from the feedstock into the microorganism. In some aspects, the constitutive overexpression of the arabinose symporter enables continuous import of xylose from the feedstock into the microorganism. In some aspects, the continuous xylose import occurs independent of the presence of other sugars in the feedstock.

Production of MEG and/or Acetone, with the Inclusion of the Xylulose Pathway

In some aspects, the recombinant microorganism comprises (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism comprises a pathway for MEG production with one or more of (c) expression of one or more endogenous or exogenous nucleic acid sequences encoding a xylose isomerase and/or, a keto-hexokinase and/or a fructose-biphosphate aldolase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylulokinases from the genome of a parent microorganism; wherein the recombinant microorganism expresses pathways for MEG and/or acetone production.

In some aspects, (c) and (d) are in an operon controlled by the proD promoter. In some aspects, the one or more nucleic acid molecules encoding the proD promoter comprises a nucleic acid sequence set forth in SEQ ID NO: 53. In some aspects, the xylose isomerase is XylA. In some aspects, the one or more nucleic acid molecules encoding the XylA comprises a nucleic acid sequence set forth in SEQ ID NO: 5. In some aspects, the one or more amino acid sequences encoding the XylA comprises an amino acid sequence set forth in SEQ ID NO: 6. In some aspects, the xylose isomerase is endogenous to the microorganism. In some aspects, the ketohexokinase is Khk-C. In some aspects, the ketohexokinase is from *Homo sapiens*. In some aspects, the ketohexokinase is heterologous to the microorganism. In some aspects, the one or more nucleic acid molecules encoding the Khk-C comprises a nucleic acid sequence set forth in SEQ ID NO: 11. In some aspects, the one or more amino acid sequences encoding the Khk-C comprises an amino acid sequence set forth in SEQ ID NO: 12. In some aspects, the fructose-biphosphate aldolase is aldoB. In some aspects, the fructose-biphosphate aldolase is from *Homo sapiens*. In some aspects, the fructose-biphosphate aldolase is heterologous to the microorganism. In some aspects, the one or more nucleic acid molecules encoding the aldoB comprises a nucleic acid sequence set forth in SEQ ID NO: 50. In some aspects, the one or more amino acid sequences encoding the aldoB comprises an amino acid sequence set forth in SEQ ID NO: 51. In some aspects, the glycoaldehyde reductase is endogenous to the microorganism. In some aspects, the glycoaldehyde reductase is fucO. In some aspects, the one or more nucleic acid molecules encoding the fucO comprises a nucleic acid sequence set forth in SEQ ID NO: 52. In some aspects, the one or more amino acid sequences encoding the fucO comprises an amino acid sequence set forth in SEQ ID NO: 98. In some aspects, the xylulokinase is XylB. In some aspects, the one or more nucleic acid molecules encoding the XylB comprises a nucleic acid sequence set forth in SEQ ID NO: 13. In some aspects, the one or more amino acid sequences encoding the XylB comprises an amino acid sequence set forth in SEQ ID NO: 14.

Production of MEG and/or Acetone with the Inclusion of the Xylonate Pathway

In some aspects, the recombinant microorganism comprises (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism comprises a pathway for MEG production with one or more of (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylose isomerases and/or one or more xylulokinases from the genome of a parent microorganism; and wherein the recombinant microorganism expresses pathways for MEG and/or acetone production.

In some aspects, the xylose dehydrogenase is from *Caulobacter crescentus, Burkholderia xenovorans*, or *Haloferax volcanii*. In some aspects, the xylose dehydrogenase is heterologous to the microorganism. In some aspects, the one or more nucleic acid molecules encoding the *Caulobacter crescentus* xylose dehydrogenase comprises a nucleic acid sequence set forth in SEQ ID NO: 15. In some aspects, the one or more amino acid sequences encoding the *Caulobacter crescentus* xylose dehydrogenase comprises an amino acid sequence set forth in SEQ ID NO: 16. In some aspects, the one or more nucleic acid molecules encoding the *Burkholderia xenovorans* xylose dehydrogenase comprises a nucleic acid sequence set forth in SEQ ID NO: 97. In some aspects, the one or more amino acid sequences encoding the *Burkholderia xenovorans* xylose dehydrogenase comprises an amino acid sequence set forth in SEQ ID NO: 17. In some aspects, the one or more nucleic acid molecules encoding the *Haloferax volcanii* xylose dehydrogenase comprises a nucleic acid sequence set forth in SEQ ID NO: 18. In some aspects, the one or more amino acid sequences encoding the *Haloferax volcanii* xylose dehydrogenase comprises an amino acid sequence set forth in SEQ ID NO: 19.

In some aspects, the xylonolactonase is from *Caulobacter crescentus, Burkholderia xenovorans*, or *Haloferax volcanii*. In some aspects, the xylonolactonase is heterologous to the microorganism. In some aspects, the xylonolactonase is endogenous to the microorganism. In some aspects, the one or more nucleic acid molecules encoding the *Caulobacter crescentus* xylonolactonase comprises a nucleic acid sequence set forth in SEQ ID NO: 54. In some aspects, the one or more nu amino acid sequences encoding the *Caulobacter crescentus* xylonolactonase comprises an amino acid sequence set forth in SEQ ID NO: 55. In some aspects, the one or more nucleic acid molecules encoding the *Burkholderia xenovorans* xylonolactonase comprises a nucleic acid sequence set forth in SEQ ID NO: 56. In some aspects, the one or more amino acid sequences encoding the *Burkholderia xenovorans* xylonolactonase comprises an amino acid sequence set forth in SEQ ID NO: 57. In some aspects, the one or more nucleic acid molecules encoding the *Haloferax volcanii* xylonolactonase comprises a nucleic acid sequence set forth in SEQ ID NO: 58. In some aspects, the one or more amino acid sequences encoding the *Haloferax volcanii* xylonolactonase comprises an amino acid sequence set forth in SEQ ID NO: 59.

In some aspects, the xylose dehydratase is from *Caulobacter crescentus, Burkholderia xenovorans*, or *Haloferax volcanii*. In some aspects, the xylose dehydratase is heterologous to the microorganism. In some aspects, the xylose dehydratase is endogenous to the microorganism. In some aspects, the one or more nucleic acid molecules encoding the *Caulobacter crescentus* xylose dehydratase comprises a nucleic acid sequence set forth in SEQ ID NO: 60. In some aspects, the one or more amino acid sequences encoding the *Caulobacter crescentus* xylose dehydratase comprises an amino acid sequence set forth in SEQ ID NO: 61. In some aspects, the one or more nucleic acid molecules encoding the *Burkholderia xenovorans* xylose dehydratase comprises a nucleic acid sequence set forth in SEQ ID NO: 62. In some aspects, the one or more amino acid sequences encoding the *Burkholderia xenovorans* xylose dehydratase comprises an amino acid sequence set forth in SEQ ID NO: 63. In some aspects, the one or more nucleic acid molecules encoding the *Haloferax volcanii* xylose dehydratase comprises a nucleic acid sequence set forth in SEQ ID NO: 64. In some aspects, the one or more amino acid sequences encoding the *Haloferax volcanii* xylose dehydratase comprises an amino acid sequence set forth in SEQ ID NO: 65. In some aspects, the glycoaldehyde reductase is endogenous to the microorganism. In some aspects, the glycoaldehyde reductase is fucO. In some aspects, the glycoaldehyde reductase is heterologous to the microorganism. In some aspects, the xylose isomerase is XylA. In some aspects, the xylulokinase is XylB.

Production of MEG and/or Acetone with the Inclusion of the Xylulose Pathway

In some aspects, the recombinant microorganism comprises (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism comprises a pathway for MEG production with one or more of (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylulokinases from the genome of a parent microorganism; wherein the recombinant microorganism comprises a pathway for acetone production with one or more of the following: (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone, wherein the recombinant microorganism expresses pathways for MEG and/or acetone production In some aspects, (f), (g) and (h) are in an operon controlled by the OXB11 promoter. In some aspects, the one or more nucleic acid molecules encoding the OXB11 comprises a nucleic acid sequence set forth in SEQ ID NO: 78. In some aspects, the acetoacetyl-CoA thiolase is a Thl. In some aspects, the thiolase is from *Clostridium acetobutylicum* or *Clostridium beijerinckii*. In some aspects, the one or more nucleic acid molecules encoding the *Clostridium acetobutylicum* thl thiolase comprises a nucleic acid sequence set forth in SEQ ID NO: 68. In some aspects, the one or more amino acid sequences encoding the *Clostridium acetobutylicum* thl thiolase comprises an amino acid sequence set forth in SEQ ID NO: 69. In some aspects, the one or more nucleic acid molecules encoding the *Clostridium beijerinckii* thl thiolase comprises a nucleic acid sequence set forth in SEQ ID NO: 66. In some aspects, the one or more amino acid sequences encoding the *Clostridium beijerinckii* thl thiolase comprises an amino acid sequence set forth in SEQ ID NO: 67. In some aspects, the acetate:acetoacetyl-CoA transferase is a AtoDA In some aspects, the acetoacetate decarboxylase is Adc. In some aspects, the decarboxylase is from *Clostridium acetobutylicum* or *Clostridium beijerinckii*. In some aspects, the one or more nucleic acid molecules encoding the *Clostridium acetobutylicum* Adc acetoacetate decarboxylase comprises a nucleic acid sequence set forth in SEQ ID NO: 74. In some aspects, the one or more amino acid sequences encoding the *Clostridium acetobutylicum* Adc acetoacetate decarboxylase comprises an amino acid sequence set forth in SEQ ID NO: 75. In some aspects, the one or more nucleic acid molecules encoding the *Clostridium beijerinckii* Adc acetoacetate decarboxylase comprises a nucleic acid sequence set forth in SEQ ID NO: 76. In some aspects, the one or more amino acid sequences encoding the *Clostridium beijerinckii* Adc acetoacetate decarboxylase comprises an amino acid sequence set forth in SEQ ID NO: 77.

Production of MEG and/or Acetone Specific to the Xylonate Pathway

In some aspects, the recombinant microorganism comprises (a) deletion or inactivation of aldA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism comprises a pathway for MEG production with one or more of (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde reductase that catalyzes the conversion of the glycoaldehyde to MEG; and (e) deletion or inactivation of one or more xylose isomerases and/or one or more xylulokinases from the genome of a parent microorganism; wherein the recombinant microorganism comprises a pathway for acetone production with one or more of the following: (f) expression of at least one exogenous nucleic acid molecule encoding an acetoacetyl-CoA thiolase; (g) expression of at least one exogenous nucleic acid molecule encoding an acetate:acetoacetyl-CoA transferase; and (h) expression of at least one exogenous nucleic acid molecule encoding an acetoacetate decarboxylase that catalyzes the conversion of acetoacetate to acetone, wherein the recombinant microorganism expresses pathways for MEG and/or acetone production.

In some aspects, (f), (g) and (h) are in an operon controlled by the OXB11 promoter. In some aspects, the acetoacetyl-CoA thiolase is a Thl. In some aspects, the thiolase is from *Clostridium acetobutylicum*. In some aspects, the acetate:acetoacetyl-CoA transferase is a AtoDA. In some aspects, the one or more nucleic acid molecules encoding the acetate:acetoacetyl-CoA transferase AtoD subunit alpha comprises a nucleic acid sequence set forth in SEQ ID NO: 70. In some aspects, the one or more amino acid sequences encoding the acetate:acetoacetyl-CoA transferase AtoD subunit alpha comprises an amino acid sequence set forth in SEQ ID NO: 72. In some aspects, the one or more nucleic acid molecules encoding the acetate:acetoacetyl-CoA transferase AtoD subunit beta comprises a nucleic acid sequence set forth in SEQ ID NO: 71. In some aspects, the one or more amino acid sequences encoding the acetate:acetoacetyl-CoA transferase AtoD subunit beta comprises an amino acid sequence set forth in SEQ ID NO: 73. In some aspects, the acetoacetate decarboxylase is Adc. In some aspects, the decarboxylase is from *Clostridium acetobutylicum* or *Clostridium beijerinckii*. In some aspects, the one or more nucleic acid molecules encoding the *Clostridium acetobutylicum* Adc acetoacetate decarboxylase comprises a nucleic acid sequence set forth in SEQ ID NO: 74. In some aspects, the one or more amino acid sequences encoding the *Clostridium acetobutylicum* Adc acetoacetate decarboxylase comprises an amino acid sequence set forth in SEQ ID NO: 75. In some aspects, the one or more nucleic acid molecules encoding the *Clostridium beijerinckii* Adc acetoacetate decarboxylase comprises a nucleic acid sequence set forth in SEQ ID NO: 76. In some aspects, the one or more amino acid sequences encoding the *Clostridium beijerinckii* Adc acetoacetate decarboxylase comprises an amino acid sequence set forth in SEQ ID NO: 77.

Production of Isopropanol

In some aspects, a recombinant microorganism capable of producing isopropanol from any one or more feedstock capable of producing acetone. In some aspects, a recombinant microorganism having been engineered to produce acetone is further engineered to express at least one exogenous nucleic acid molecule encoding an alcohol dehydrogenase that catalyzes the conversion of acetone to isopropanol. In some aspects (f), (g), and (h) of the preceding acetone production disclosure is further modified with (i)—expression of at least one exogenous nucleic acid molecule encoding an alcohol dehydrogenase that catalyzes the conversion of acetone to isopropanol. In some aspects, the one or more nucleic acid molecules encoding the alcohol dehydrogenase comprises a nucleic acid sequence set forth in SEQ ID NO: 93. In some aspects, the one or more amino acid sequences encoding the alcohol dehydrogenase comprises an amino acid sequence set forth in SEQ ID NO: 94.

Production of Glycolic Acid

In some aspects, a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD (SEQ ID NO: 1 or SEQ ID NO: 2), araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid.

In some aspects, the one or more nucleic acid molecules encoding the AraF periplasmic binding protein subunit of AraFGH comprises a nucleic acid sequence set forth in SEQ ID NO: 20. In some aspects, the one or more amino acid sequences encoding the AraF periplasmic binding protein subunit of AraFGH comprises an amino acid sequence set forth in SEQ ID NO: 23. In some aspects, the one or more nucleic acid molecules encoding the AraG ATP-binding subunit of AraFGH comprises a nucleic acid sequence set forth in SEQ ID NO: 21. In some aspects, the one or more amino acid sequences encoding the AraG ATP-binding subunit of AraFGH comprises an amino acid sequence set forth in SEQ ID NO: 24. In some aspects, the one or more nucleic acid molecules encoding the AraH membrane subunit of AraFGH comprises a nucleic acid sequence set forth in SEQ ID NO: 22. In some aspects, the one or more amino acid sequences encoding the AraH membrane subunit of AraFGH comprises an amino acid sequence set forth in SEQ ID NO: 25.

In some aspects, the one or more nucleic acid molecules encoding the xylF periplasmic binding protein subunit of xylFGH comprises a nucleic acid sequence set forth in SEQ ID NO: 26. In some aspects, the one or more amino acid sequences encoding the xylF periplasmic binding protein subunit of xylFGH comprises an amino acid sequence set forth in SEQ ID NO: 29. In some aspects, the one or more nucleic acid molecules encoding the xylG ATP-binding subunit of xylFGH comprises a nucleic acid sequence set forth in SEQ ID NO: 27. In some aspects, the one or more amino acid sequences encoding the xylG ATP-binding subunit of xylFGH comprises an amino acid sequence set forth in SEQ ID NO: 30. In some aspects, the one or more nucleic acid molecules encoding the xylH membrane subunit of xylFGH comprises a nucleic acid sequence set forth in SEQ ID NO: 28. In some aspects, the one or more amino acid sequences encoding the xylH membrane subunit of xylFGH comprises an amino acid sequence set forth in SEQ ID NO: 31.

In some aspects, the microorganism further comprise the deletion or inactivation of glcDEF. In some aspects, the one or more nucleic acid molecules encoding the putative FAD-linked subunit GlcD comprises a nucleic acid sequence set forth in SEQ ID NO: 79. In some aspects, the one or more amino acid sequences encoding the putative FAD-linked subunit GlcD comprises an amino acid sequence set forth in SEQ ID NO: 82. In some aspects, the one or more nucleic acid molecules encoding the putative FAD-binding subunit GlcE comprises a nucleic acid sequence set forth in SEQ ID NO: 80. In some aspects, the one or more amino acid sequences encoding the putative FAD-binding subunit GlcE comprises an amino acid sequence set forth in SEQ ID NO: 83. In some aspects, the one or more nucleic acid molecules encoding the putative iron-sulfur subunit GlcF comprises a nucleic acid sequence set forth in SEQ ID NO: 81. In some aspects, the one or more amino acid sequences encoding the putative iron-sulfur subunit GlcF comprises an amino acid sequence set forth in SEQ ID NO: 84. In some aspects, the microorganism further comprises the deletion or inactivation of aldehyde reductase, dkgA. In some aspects, the one or more nucleic acid molecules encoding the dkgA comprises a nucleic acid sequence set forth in SEQ ID NO: 85. In some aspects, the one or more amino acid sequences encoding the dkgA comprises an amino acid sequence set forth in SEQ ID NO: 86. In some aspects, the microorganism further comprises the deletion or inactivation of aldehyde reductase yahK. In some aspects, the one or more nucleic acid molecules encoding the yahK comprises a nucleic acid sequence set forth in SEQ ID NO: 87. In some aspects, the one or more amino acid sequences encoding the yahK comprises an amino acid sequence set forth in SEQ ID NO: 88. In some aspects, the xylose symporter is controlled by a GAPDH promoter at the araFGH locus. In some aspects, the C5 sugar symporter is a xylose symporter XylE. In some aspects, the one or more nucleic acid molecules encoding the xylE comprises a nucleic acid sequence set forth in SEQ ID NO: 48. In some aspects, the one or more amino acid sequences encoding the xylE comprises an amino acid sequence set forth in SEQ ID NO: 49. In some aspects, the xylose symporter is endogenous to the microorganism. In some aspects, the C5 sugar symporter is an arabinose symporter AraE. In some aspects, the one or more nucleic acid molecules encoding the araE comprises a nucleic acid sequence set forth in SEQ ID NO: 46. In some aspects, the one or more amino acid sequences encoding the araE comprises an amino acid sequence set forth in SEQ ID NO: 47. In some aspects, the arabinose symporter is endogenous to the microorganism. In some aspects, the uptake of the xylose is not sensitive to catabolic repression by other monosaccharides. In some aspects, the microorganism comprises a functional phosphotransferase system. In some aspects, the microorganism comprises a native wild-type nucleic acid sequence encoding a cAMP receptor protein (CRP). In some aspects, the one or more nucleic acid molecules encoding the CRP comprises a nucleic acid sequence set forth in SEQ ID NO: 9. In some aspects, the one or more amino acid sequences encoding the CRP comprises an amino acid sequence set forth in SEQ ID NO: 10. In some aspects, the constitutive overexpression of the xylose symporter enables continuous import of xylose from the feedstock into the microorganism. In some aspects, the constitutive overexpression of the arabinose symporter enables continuous import of xylose from the feedstock into the microorganism. In some aspects, the continuous xylose import occurs independent of the presence of other sugars in the feedstock.

Production of Glycolic Acid with the Inclusion of the Xylulose Pathway

In some aspects, a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO yqhD, yahK, dkgA araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid, with one or more of the following: (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylulokinases from the genome of a parent microorganism.

In some aspects, (c) and (d) are in an operon controlled by the proD promoter. In some aspects, the one or more nucleic acid molecules encoding the proD promoter comprises a nucleic acid sequence set forth in SEQ ID NO: 53. In some aspects, the xylose isomerase is XylA. In some aspects, the one or more nucleic acid molecules encoding the xylA comprises a nucleic acid sequence set forth in SEQ ID NO: 5. In some aspects, the one or more amino acid sequences encoding the xylA comprises an amino acid sequence set forth in SEQ ID NO: 6. In some aspects, the xylose isomerase is endogenous to the microorganism. In some aspects, the xylose isomerase is heterologous to the microorganism. In some aspects, the ketohexokinase is Khk-C. In some aspects, the one or more nucleic acid molecules encoding the khk-C comprises a nucleic acid sequence set forth in SEQ ID NO: 11. In some aspects, the one or more amino acid sequences encoding the khk-C comprises an amino acid sequence set forth in SEQ ID NO: 12. In some aspects, the ketohexokinase is from *Homo sapiens*. In some aspects, the fructose-biphosphate aldolase is aldoB. In some aspects, the one or more nucleic acid molecules encoding the aldoB comprises a nucleic acid sequence set forth in SEQ ID NO: 50. In some aspects, the one or more amino acid sequences encoding the aldoB comprises an amino acid sequence set forth in SEQ ID NO: 51. In some aspects, the fructose-biphosphate aldolase is from *Homo sapiens*. In some aspects, the glycoaldehyde dehydrogenase is endogenous to the microorganism. In some aspects, the glycolaldehyde dehydrogenase is heterologous to the microorganism. In some aspects, the glycoaldehyde dehydrogenase is aldA In some aspects, the one or more nucleic acid molecules encoding the aldA comprises a nucleic acid sequence set forth in SEQ ID NO: 3. In some aspects, the one or more amino acid sequences encoding the aldA comprises an amino acid sequence set forth in SEQ ID NO: 4. In some aspects, the xylulokinase is XylB. In some aspects, the one or more nucleic acid molecules encoding the xylB comprises a nucleic acid sequence set forth in SEQ ID NO: 13. In some aspects, the one or more amino acid sequences encoding the xylB comprises an amino acid sequence set forth in SEQ ID NO: 14.

Production of Glycolic Acid with the Inclusion of the Xylonate Pathway

In some aspects, a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD, yahK, dkgA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid, with one or more of the following: (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylose isomerases and/or one or more xylulokinases from the genome of a parent microorganism.

In some aspects, (c) and (d) are controlled by the proD promoter. In some aspects, the xylose isomerase is XylA. In some aspects, the xylulokinase is XylB. In some aspects, the xylose dehydrogenase is from *Caulobacter crescentus*. *Burkholderia xenovorans*, or *Haloferax volcanii*. In some aspects, the xylose dehydrogenase is heterologous to the microorganism. In some aspects, the xylonolactonase is from *Caulobacter crescentus, Burkholderia xenovorans*, or *Haloferax volcanii*. In some aspects, the xylonolactonase is heterologous to the microorganism. In some aspects, the xylonolactonase is endogenous to the microorganism. In some aspects, the glycoaldehyde dehydrogenase is aldA. In some aspects, the glycoaldehyde dehydrogenase is endogenous to the microorganism.

Production of Glycolic Acid (Alternative Pathway) with the Inclusion of the Xylulose Pathway—

In some aspects, a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD, yahK, dkgA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid, with one or more of the following: (c) expression of one or more endogenous or exogenous nucleic acid sequences encoding a xylose isomerase and/or, a ketohexokinase and/or a fructose-biphosphate aldolase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylulokinases from the genome of a parent microorganism; and wherein the microorganism further expresses a pathway for the production of glycolic acid with one or more of the following: (f) expression of at least one endogenous or exogenous nucleic acid molecule encoding an isocitrate lyase; and/or (g) expression of at least one endogenous or exogenous nucleic acid molecule encoding a glyoxylate reductase. In some aspects, (f) and (g) are in an operon controlled by the OXB20 promoter. In some aspects, the one or more nucleic acid molecules encoding the OXB20 promoter comprises a nucleic acid sequence set forth in SEQ ID NO: 96. In some aspects the isocitrate lyase is AceA. In some aspects the glyoxylate reductase is YcdW. In some aspects, the one or more nucleic acid molecules encoding the ycdW comprises a nucleic acid sequence set forth in SEQ ID NO: 91. In some aspects, the one or more amino acid sequences encoding the ycdW comprises an amino acid sequence set forth in SEQ ID NO: 92.

Production of Glycolic Acid (Alternative Pathway) with the Inclusion of the Xylonate Pathway In some aspects, a recombinant microorganism capable of producing glycolic acid from a feedstock comprising xylose and glucose, wherein the recombinant microorganism simultaneously utilizes xylose and glucose, comprising one or more of the following: (a) deletion or inactivation of fucO, yqhD, yahK, dkgA, araFGH, and xylFGH from the genome of a parent microorganism; and (b) expression of at least one endogenous or exogenous nucleic acid molecule operatively linked to one or more constitutive promoters encoding a C5 sugar symporter; wherein the recombinant microorganism further expresses one or more pathways for the production of glycolic acid, with one or more of the following: (c) expression of one or more endogenous or exogenous nucleic acid sequences encoding a xylose dehydrogenase and/or a xylonolactonase and/or a xylose dehydratase operatively linked to one or more constitutive promoters; (d) expression of at least one endogenous or exogenous nucleic acid molecule encoding a glycoaldehyde dehydrogenase that catalyzes the conversion of the glycoaldehyde to glycolic acid; and (e) deletion or inactivation of one or more xylose isomerases and/or one or more xylulokinases from the genome of a parent microorganism; and wherein the microorganism further expresses a pathway for the production of glycolic acid with one or more of the following: (f) expression of at least one endogenous or exogenous nucleic acid molecule encoding an isocitrate lyase; and/or (g) expression of at least one endogenous or exogenous nucleic acid molecule encoding a glyoxylate reductase.

In some aspects, (f) and (g) are in an operon controlled by the OXB20 promoter. In some aspects the isocitrate lyase is AceA. In some aspects, the glyoxylate reductase is YcdW.

Recombinant Microbes Comprising the Sequences and Modifications Described Herein In some aspects, the disclosure is broadly drawn to recombinant microbes of any one of the preceding aspects, wherein the recombinant microorganism is derived from a parental microorganism selected from the group consisting of *Clostridium* sp., *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Clostridium acetobutylicum*, *Clostridium beijerinckii*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, *Escherichia coli*, *Saccharomyces cerevisiae*, *Pseudomonas putida*, *Bacillus* sp., *Corynebacterium* sp., *Yarrowia lipolytica*, *Scheffersomyces stipitis*, and *Terrisporobacter glycolicus*. In some aspects, the parental microorganism is *E. coli*.

In some aspects, enzymes, proteins, promoters, and nucleic acids of the disclosure are outlined in Table 1.

TABLE 1

Proteins and Nucleic Acids of the Disclosure

| Gene | Enzyme | Species | DNA or Protein | SEQ ID NO: |
| --- | --- | --- | --- | --- |
| yqhD | aldehyde reductase | Escherichia coli | DNA | 1 |
| yqhD | aldehyde reductase | Escherichia coli | PRT | 2 |
| aldA | aldehyde dehydrogenase | Escherichia coli | DNA | 3 |
| aldA | aldehyde dehydrogenase | Escherichia coli | PRT | 4 |
| XylA | D-xylose isomerase | Escherichia coli | DNA | 5 |
| XylA | D-xylose isomerase | Escherichia coli | PRT | 6 |
| XylR | DNA-binding transcriptional dual regulator involved in D-xylose degradation | Escherichia coli | DNA | 7 |
| XylR | DNA-binding transcriptional dual regulator involved in D-xylose degradation | Escherichia coli | PRT | 8 |
| CRP | cAMP receptor protein | Escherichia coli | DNA | 9 |
| CRP | cAMP receptor protein | Escherichia coli | PRT | 10 |
| khk-C | Ketohexokinase | Homo sapiens | DNA | 11 |
| khk-C | Ketohexokinase | Homo sapiens | PRT | 12 |
| XylB | xylulokinase | Escherichia coli | DNA | 13 |
| XylB | xylulokinase | Escherichia coli | PRT | 14 |
| xdh | xylose dehydrogenase | Caulobacter crescentus | DNA | 15 |
| xdh | xylose dehydrogenase | Caulobacter crescentus | PRT | 16 |
| DR64_8447 | xylose dehydrogenase | Burkholderia xenovorans | DNA | 97 |
| DR64_8447 | xylose dehydrogenase | Burkholderia xenovorans | PRT | 17 |
| HVO_B0028 | xylose dehydrogenase | Haloferax volcanii | DNA | 18 |
| HVO_B0028 | xylose dehydrogenase | Haloferax volcanii | PRT | 19 |
| AraF | periplasmic binding protein subunit from ABC-type L-arabinose transporter | Escherichia coli | DNA | 20 |

TABLE 1-continued

Proteins and Nucleic Acids of the Disclosure

| Gene | Enzyme | Species | DNA or Protein | SEQ ID NO: |
|---|---|---|---|---|
| AraF | periplasmic binding protein subunit from ABC-type L-arabinose transporter | Escherichia coli | PRT | 23 |
| AraG | ATP-binding subunit subunit from ABC-type L-arabinose transporter | Escherichia coli | DNA | 21 |
| AraG | ATP-binding subunit subunit from ABC-type L-arabinose transporter | Escherichia coli | PRT | 24 |
| AraH | membrane subunit subunit from ABC-type L-arabinose transporter | Escherichia coli | DNA | 22 |
| AraH | membrane subunit subunit from ABC-type L-arabinose transporter | Escherichia coli | PRT | 25 |
| xylF | periplasmic binding protein subunit from ABC-type L-xylose transporter | Escherichia coli | DNA | 26 |
| xylF | periplasmic binding protein subunit from ABC-type L-xylose transporter | Escherichia coli | PRT | 29 |
| xylG | ATP-binding subunit from ABC-type L-xylose transporter | Escherichia coli | DNA | 27 |
| xylG | ATP-binding subunit from ABC-type L-xylose transporter | Escherichia coli | PRT | 30 |
| xy1H | membrane subunit from ABC-type L-xylose transporter | Escherichia coli | DNA | 28 |
| xy1H | membrane subunit from ABC-type L-xylose transporter | Escherichia coli | PRT | 31 |
| AraC | DNA-binding transcriptional dual regulator involved in D-arabinose degradation | Escherichia coli | DNA | 32 |
| AraC | DNA-binding transcriptional dual regulator involved in D-arabinose degradation | Escherichia coli | PRT | 33 |
| RbsA | ATP-binding subunit from ribose ABC transporter | Escherichia coli | DNA | 34 |
| RbsA | ATP-binding subunit from ribose ABC transporter | Escherichia coli | PRT | 37 |
| RbsB | periplasmic binding protein from ribose ABC transporter | Escherichia coli | DNA | 35 |
| RbsB | periplasmic binding protein from ribose ABC transporter | Escherichia coli | PRT | 38 |
| RbsC | membrane subunit from ribose ABC transporter | Escherichia coli | DNA | 36 |
| RbsC | membrane subunit from ribose ABC transporter | Escherichia coli | PRT | 39 |
| AlsA | ATP-binding subunit from D-allose ABC transporter | Escherichia coli | DNA | 40 |
| AlsA | ATP-binding subunit from D-allose ABC transporter | Escherichia coli | PRT | 43 |
| AlsB | periplasmic binding protein from D-allose ABC transporter | Escherichia coli | DNA | 41 |
| AlsB | periplasmic binding protein from D-allose ABC transporter | Escherichia coli | PRT | 44 |

TABLE 1-continued

Proteins and Nucleic Acids of the Disclosure

| Gene | Enzyme | Species | DNA or Protein | SEQ ID NO: |
|---|---|---|---|---|
| AlsC | membrane subunit from D-allose ABC transporter | Escherichia coli | DNA | 42 |
| AlsC | membrane subunit from D-allose ABC transporter | Escherichia coli | PRT | 45 |
| araE | arabinose symporter | Escherichia coli | DNA | 46 |
| araE | arabinose symporter | Escherichia coli | PRT | 47 |
| xylE | xylose symporter | Escherichia coli | DNA | 48 |
| xylE | xylose symporter | Escherichia coli | PRT | 49 |
| aldoB | fructose-biphosphate aldolase | Homo sapiens | DNA | 50 |
| aldoB | fructose-biphosphate aldolase | Homo sapiens | PRT | 51 |
| fucO | glycoaldehyde reductase | Escherichia coli | DNA | 52 |
| fucO | glycoaldehyde reductase | Escherichia coli | PRT | 98 |
| proD promoter | proD promoter | Constitutive synthetic bacterial promoter | DNA | 53 |
| xylC | xylonolactonase | Caulobacter crescentus | DNA | 54 |
| xylC | xylonolactonase | Caulobacter crescentus | PRT | 55 |
| DR64_8448 | xylonolactonase | Burkholderia xenovorans | DNA | 56 |
| DR64_8448 | xylonolactonase | Burkholderia xenovorans | PRT | 57 |
| HVO_B0030 | xylonolactonase | Haloferax volcanii | DNA | 58 |
| HVO_B0030 | xylonolactonase | Haloferax volcanii | PRT | 59 |
| xylD | xylonate dehydratase | Caulobacter crescentus | DNA | 60 |
| xylD | xylonate dehydratase | Caulobacter crescentus | PRT | 61 |
| DR64_8449 | xylonate dehydratase | Burkholderia xenovorans | DNA | 62 |
| DR64_8449 | xylonate dehydratase | Burkholderia xenovorans | PRT | 63 |
| HVO_B0038A | xylonate dehydratase | Haloferax volcanii | DNA | 64 |
| HVO_B0038A | xylonate dehydratase | Haloferax volcanii | PRT | 65 |
| Thl | acetoacetyl-CoA thiolase or acetoacetyl-CoA acetyltransferase | Clostridium beijerinckii | DNA | 66 |
| Thl | acetoacetyl-CoA thiolase or acetoacetyl-CoA acetyltransferase | Clostridium beijerinckii | PRT | 67 |
| Thl | acetoacetyl-CoA thiolase or acetoacetyl-CoA acetyltransferase | Clostridium acetobutylicum | DNA | 68 |
| Thl | acetoacetyl-CoA thiolase or acetoacetyl-CoA acetyltransferase | Clostridium acetobutylicum | PRT | 69 |
| AtoD | subunit α of acetoacetyl-CoA transferase | Escherichia coli | DNA | 70 |
| AtoD | subunit α of acetoacetyl-CoA transferase | Escherichia coli | PRT | 72 |
| AtoA | subunit β of acetoacetyl-CoA transferase | Escherichia coli | DNA | 71 |
| AtoA | subunit β of acetoacetyl-CoA transferase | Escherichia coli | PRT | 73 |
| Adc | acetoacetate decarboxylase | Clostridium acetobutylicum | DNA | 74 |
| Adc | acetoacetate decarboxylase | Clostridium acetobutylicum | PRT | 75 |
| Adc | acetoacetate decarboxylase | Clostridium beijerinckii | DNA | 76 |
| Adc | acetoacetate decarboxylase | Clostridium beijerinckii | PRT | 77 |
| OXB11 | OXB11 promoter | Constitutive synthetic bacterial promoter | DNA | 78 |
| GlcD | putative FAD-linked subunit of glycolate dehydrogenase | Escherichia coli | DNA | 79 |
| GlcD | putative FAD-linked subunit of glycolate dehydrogenase | Escherichia coli | PRT | 82 |
| GlcE | putative FAD-binding subunit of glycolate dehydrogenase | Escherichia coli | DNA | 80 |
| GlcE | putative FAD-binding subunit of glycolate dehydrogenase | Escherichia coli | PRT | 83 |
| GlcF | iron-sulfur subunit of glycolate dehydrogenase | Escherichia coli | DNA | 81 |
| GlcF | iron-sulfur subunit of glycolate dehydrogenase | Escherichia coli | PRT | 84 |
| dkgA | aldehyde reductase | Escherichia coli | DNA | 85 |
| dkgA | aldehyde reductase | Escherichia coli | PRT | 86 |

TABLE 1-continued

Proteins and Nucleic Acids of the Disclosure

| Gene | Enzyme | Species | DNA or Protein | SEQ ID NO: |
|---|---|---|---|---|
| yahK | aldehyde reductase | Escherichia coli | DNA | 87 |
| yahK | aldehyde reductase | Escherichia coli | PRT | 88 |
| AceA | isocitrate lyase | Escherichia coli | DNA | 89 |
| AceA | isocitrate lyase | Escherichia coli | PRT | 90 |
| YcdW (ghrA) | glyoxylate reductase | Escherichia coli | DNA | 91 |
| YcdW (ghrA) | glyoxylate reductase | Escherichia coli | PRT | 92 |
| adh | alcohol dehydrogenase | Clostridium beijerinckii | DNA | 93 |
| adh | alcohol dehydrogenase | Clostridium beijerinckii | PRT | 94 |
| GAPDH promoter | gapA promoter | Escherichia coli | DNA | 95 |
| OXB20 | OXB20 promoter | Constitutive synthetic bacterial promoter | DNA | 96 |

Methods of Detecting Genetic Modification

The present disclosure teaches primers, probes, and assays that are useful for detecting the microbes taught herein. In some aspects, the disclosure provides for methods of detecting the WT parental strains. In other aspects, the disclosure provides for methods of detecting the engineered or modified microbes derived from parent strains or WT strains. In some aspects, the present disclosure provides methods of identifying genetic alterations in a microbe.

In some aspects, the genomic engineering methods of the present disclosure lead to the creation of non-natural nucleotide "junction" sequences in the modified microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some aspects, the probes of the disclosure bind to the non-naturally occurring nucleotide junction sequences. In some aspects, traditional PCR is utilized. In other aspects, real-time PCR is utilized. In some aspects, quantitative PCR (qPCR) is utilized. In some aspects, the PCR methods are used to identify heterologous sequences that have been inserted into the genomic DNA or extra-genomic DNA of the microbes.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some aspects, only the non-naturally occurring nucleotide junction will be amplified via the taught primers, and consequently can be detected via either a non-specific dye, or via the utilization of a specific hybridization probe. In other aspects, the primers of the disclosure are chosen such that the primers flank either side of a junction sequence, such that if an amplification reaction occurs, then said junction sequence is present.

Aspects of the disclosure involve non-naturally occurring nucleotide junction sequence molecules per se, along with other nucleotide molecules that are capable of binding to said non-naturally occurring nucleotide junction sequences under mild to stringent hybridization conditions. In some aspects, the nucleotide molecules that are capable of binding to said non-naturally occurring nucleotide junction sequences under mild to stringent hybridization conditions are termed "nucleotide probes."

In some aspects, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which may act as a calibration standard.

TaqMan probes are often utilized in qPCR assays that require an increased specificity for quantifying target nucleic acid sequences. TaqMan probes comprise an oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR allow the practitioner to eliminate the labor-intensive post-amplification step of gel electrophoresis preparation, which is generally required for observation of the amplified products of traditional PCR assays. The benefits of qPCR over conventional PCR are considerable, and include increased speed, ease of use, reproducibility, and quantitative ability.

Microbial Compositions

In some aspects, the microbes of the disclosure are combined into microbial compositions.

In some aspects, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim milk powder; sweet whey powder; maltodextrin; lactose; inulin; dextrose; and products of vegetable origin such as cereal meals, tree bark meal, wood meal, and nutshell meal.

In some aspects, the microbial compositions of the present disclosure are liquid. In further aspects, the liquid comprises a solvent that may include water or an alcohol or a saline or carbohydrate solution. In some aspects, the microbial compositions of the present disclosure include binders such as polymers, carboxymethylcellulose, starch, polyvinyl alcohol, and the like.

In some aspects, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In further aspect, microbial compositions comprise polymers of agar, agarose, gelrite, gellan gum, and the like. In some aspects, microbial compositions comprise plastic capsules, emulsions (e.g., water and oil), membranes, and artificial membranes. In some aspects, emulsions or linked polymer solutions may comprise microbial compositions of the present disclosure. See Harel and Bennett (U.S. Pat. No. 8,460,726 B2).

In some aspects, microbial compositions of the present disclosure occur in a solid form (e.g., dispersed lyophilized spores) or a liquid form (microbes interspersed in a storage medium). In some aspects, microbial compositions of the present disclosure are added in dry form to a liquid to form a suspension immediately prior to use. In some aspects, the microbial composition comprises vitrified microbes.

In some aspects, the microbial composition of the present disclosure possesses a water activity (aw) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some aspects, the microbial composition of the present disclosure possesses a water activity (aw) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

The water activity values are determined by the method of Saturated Aqueous Solutions (Multon, "Techniques d'Analyse E De Controle Dans Les Industries Agroalimentaires" APRIA (1981)) or by direct measurement using a viable Robotronic BT hygrometer or other hygrometer or hygroscope.

Feedstock

In some aspects, the disclosure is drawn to a method of producing and recovering/isolating one or more desirable chemicals. The recovery/collection/isolation can be by methods known in the art, such as distillation, membrane-based separation gas stripping, solvent extraction, and expanded bed adsorption.

In some aspects, the feedstock comprises a carbon source. In some aspects, the carbon source may be selected from sugars, glycerol, alcohols, organic acids, alkanes, fatty acids, lignocellulose, proteins, carbon dioxide, and carbon monoxide. In one aspect, the carbon source is a sugar. In one aspect, the sugar is glucose or oligomers of glucose thereof. In one aspect, the oligomers of glucose are selected from fructose, sucrose, starch, cellobiose, maltose, lactose and cellulose. In one aspect, the sugar is a five carbon sugar. In one aspect, the sugar is a six carbon sugar. In some aspects, the feedstock comprises one or more five carbon sugars and/or one or more six carbon sugars. In some aspects, the feedstock comprises one or more of xylose, glucose, arabinose, galactose, maltose, fructose, mannose, sucrose, and/or combinations thereof. In some aspects, the feedstock comprises one or more of xylose and/or glucose. In some aspects, the feedstock comprises one or more of arabinose, galactose, maltose, fructose, mannose, sucrose, and/or combinations thereof. In some aspect, the feedstock comprises xylose and glucose.

In some aspects, the microbes utilize one or more five carbon sugars (pentoses) and/or one or more six carbon sugars (hexoses). In some aspects, the microbes utilize one or more of xylose and/or glucose. In some aspects, the microbes utilize one or more of arabinose, galactose, maltose, fructose, mannose, sucrose, and/or combinations thereof. In some aspects, the microbes utilize one or more of xylose, glucose, arabinose, galactose, maltose, fructose, mannose, sucrose, and/or combinations thereof In some aspects, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some aspects, pentoses may be selected from D-xylose, D-ribose, D-arabinose, D-lyxose, D-xylulose, D-ribulose, and other pentoses known in the art. In some aspects, the hexoses and pentoses may be selected from the levorotary or dextrorotary enantiomer of any of the hexoses and pentoses disclosed herein.

In some aspects, total amount of C5 and/or C6 carbohydrates fed to a bioreactor/growth medium during the growth phase is at least 5 kg carbohydrate/m3, at least 10 kg carbohydrate/m3, at least 20 kg carbohydrate/m3, at least 30 kg carbohydrate/m3, at least 40 kg carbohydrate/m3, at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3 at least 500 kg carbohydrate/m3, at least 600 kg carbohydrate/m3, at least 700 kg carbohydrate/m3, up to 800 kg carbohydrate/m3. In some aspects, total amount of C5 and/or C6 carbohydrates fed to the bioreactor/growth medium during the growth phase ranges from about 10 kg carbohydrate/m3 up to 500 kg carbohydrate/m3.

In some aspects, time required for the growth phase varies between 1 to 200 hours. In further aspects, the time of the growth phase is between 5 to 50 hours. The time is dependent on carbohydrate feeds and/or feedstocks.

In some aspects, the total amount of C5 and/or C6 carbohydrates fed to the bioreactor/growth medium during the production phase is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some aspects, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase varies between 5 to 500 hours. In further aspects, the time for the production phase varies from 10 to 300 hours for batch and fed-batch operations. In other aspects, the time of the production phase is up to 300 hours with continuous fermentation.

In some aspects, the total amount of C5 and/or C6 carbohydrates fed to the bioreactor/growth medium for one-phase process is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some aspects, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase in the one-phase process varies between 5 to 500 hours. In further aspects, the time required for production phase in the one-phase process varies between 5 to 300 hours.

In some aspects, the one-phase or multi-phase production processes take about 5, about 10, about 25, about 50, about 75, about 100, about 125, about 150, about 175, about 200, about 225, about 250, about 275, about 300 about 325, about 350, about 375, about 400, about 425, about 450, about 475, or about 500 hours.

In some aspects, the one-phase or multi-phase production processes take 5, 10, 25, 50, 75, 100, 125, 150, 175, 200, 225, 250, 275, 300 325, 350, 375, 400, 425, 450, 475, or 500 hours.

Improvement of Traits

Methods of the present disclosure may be employed to introduce or improve one or more of a variety of desirable traits. Examples of traits that may be introduced or improved including: an increase in the rate and or velocity of MEG, glycolic acid, polyols, acetone, propene, isopropanol; increase in the simultaneous consumption of xylose and glucose; and a decrease in the inhibitory effects of one or more saccharides on the saccharide consumption and/or uptake.

In some aspects, a microbe resulting from the methods described herein exhibits a difference in the trait that is at least about 1% greater, for example at least about 1%, at least about 2%, at least about 3%, at least about 4%, at least about 5%, at least about 6%, at least about 7%, at least about 9%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 90%, or at least 100%, at least about 200%, at least about 300%, at least about 400% or greater than a reference under control conditions. In additional examples, a microbe resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference control grown under similar conditions.

In some aspects, the increase or decrease of any one or more of the traits of the present disclosure is an increase of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 9'7%, about 98%, about 99%, or about 100% relative to an unmodified microbe.

In some aspects, the increase or decrease of any one or more of the traits of the present disclosure is an increase of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative an unmodified microbe.

EXAMPLES

Example 1: Co-Production of Monoethylene Glycol (MEG) and Acetone Via D-Xylonate Pathway in a Strain Capable of Simultaneously Consuming Xylose and Glucose—Pathway a of FIG. 1

The E. coli K12 strain MG1655 was used as the host for the deletion of three genes that could divert the carbon flux from MEG+Acetone pathway: aldA, xylA, and glcDEF. The genes were successfully deleted and the deletion confirmed by PCR and sequencing. The next step was the integration of the MEG pathway. An operon expressed under control of the proD promoter containing a xdh gene (xylose dehydrogenase) and a fucO gene (glycoaldehyde reductase), encoding, respectively, for the first and last enzymes of the xylonate pathway, was integrated in the E. coli genome and an additional copy of the xdh gene was also placed under the control of the proD promoter and was integrated in a different loci. The integration of the xdh gene allows for the conversion of xylose into the intermediates D-xylonate and glycolaldehyde. The integration of the fucO gene reduces the glycolaldehyde to MEG, and is specific to MEG production. The second step was the integration of the acetone pathway. An operon expressed under control of OXB11 promoter containing a thlA gene (acetoacetyl-CoA thiolase); AtoDA genes (acetate:acetoacetyl-CoA transferase) and an adc gene (acetoacetate decarboxylase) was integrated in the E. coli genome, generating the base strain. The base strain was used as the host for the modifications to promote co-consumption of glucose and xylose. The first modification was the integration of an additional copy of xylE under control of a GAPDH promoter on the araFGH locus, thus deleting araFGH. The second modification was the deletion of the xylFGH operon. All of the integrations and deletions were confirmed by PCR and sequencing.

Colonies from the transformations were inoculated in 5 mL of mineral media containing either 12.85 g/L of xylose and 2.15 g/L of glucose (6:1 proportion) or 7.5 g/L of xylose and 7.5 g/L of glucose (1:1 proportion) for pre-culture. After 16 hours of cultivation 5% of the pre-culture was transferred to 100 mL of fresh media. The flasks were incubated at 37° C., 250 rpm. The initial OD of the cultivation was 0.1.

Figure 2:
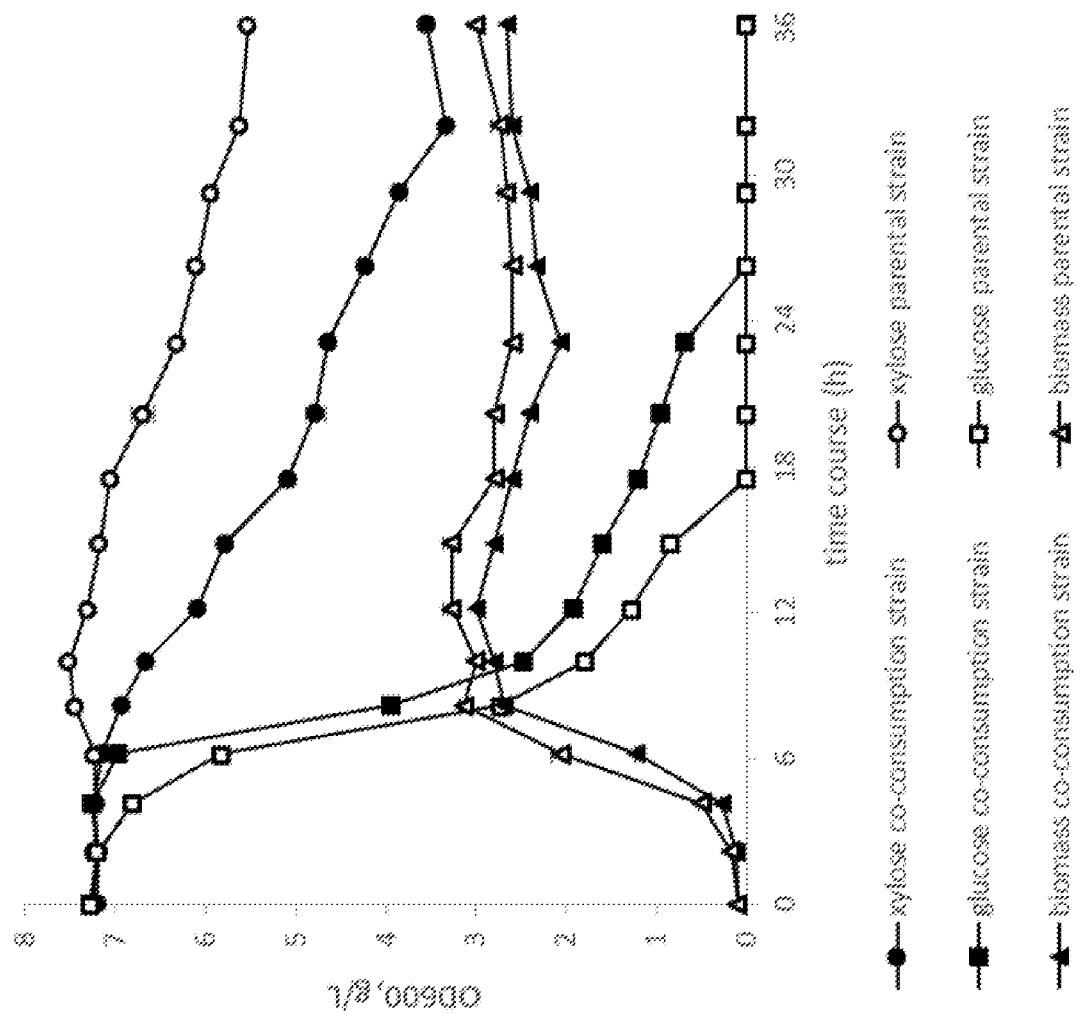
FIG. 2 is a graph depicting the detection of simultaneous utilization of glucose and xylose in a co-consumption strain, while in the parental strain the xylose began to be consumed only after glucose was depleted; in 1:1 proportion cultures.

For the 1:1 proportion cultures, after 8 hours of cultivation simultaneous utilization of glucose and xylose could be detected in the co-consumption strain while in the parental strain the xylose started to be consumed only after 18 h, after depletion of glucose (FIG. 2). In 36 h of cultivation, the co-consumption strain was able to consume 75% of initial mixture of sugars while the parental strain consumed only 62%.

Figure 3:
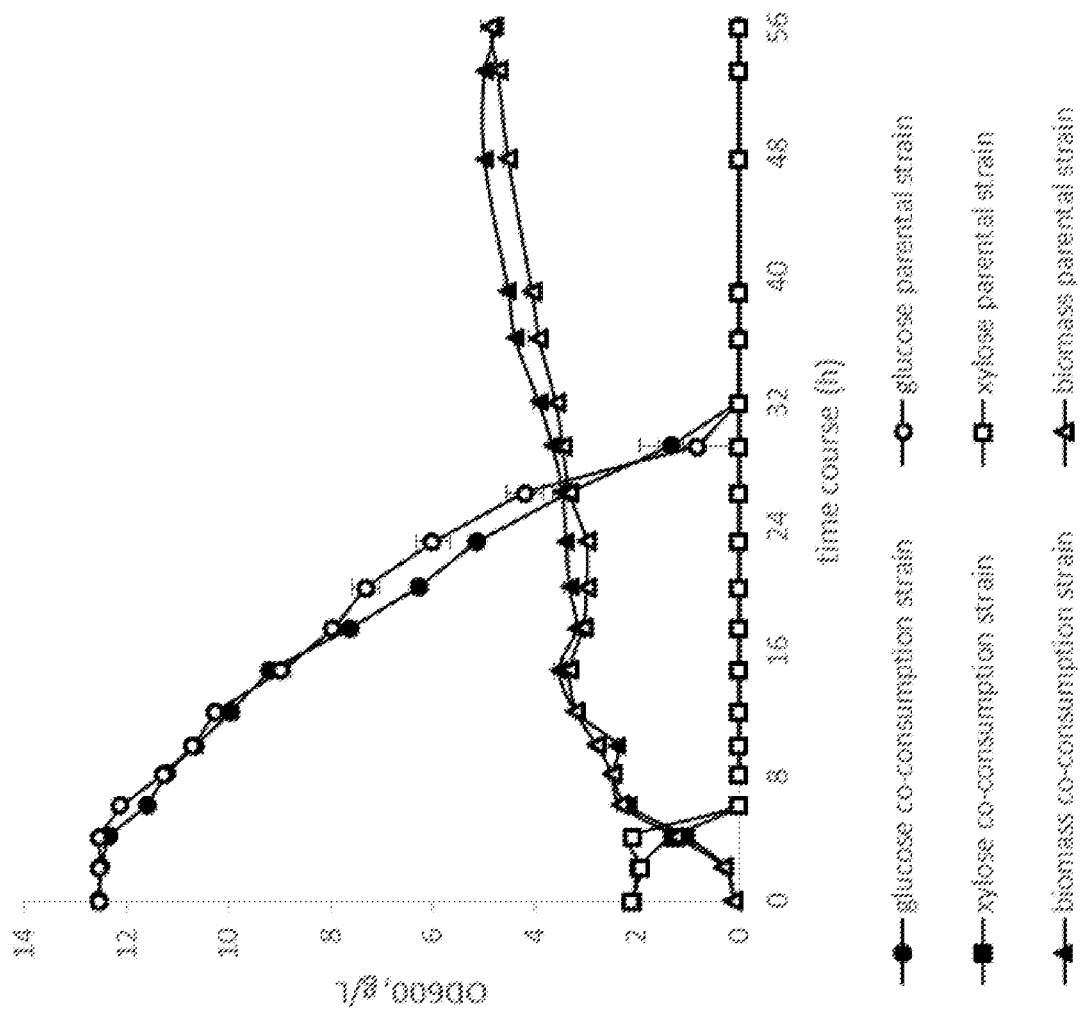
FIG. 3 is a graph depicting the co-consumption strain consuming 75% of the initial mixture of sugars while the parental strain consumed only 62% (36 h of cultivation). For 6:1 proportion cultures, both parental and co-consumption strains fully consumed the initial glucose and xylose, with similar profiles of xylose consumption and biomass production.
Figure 4:
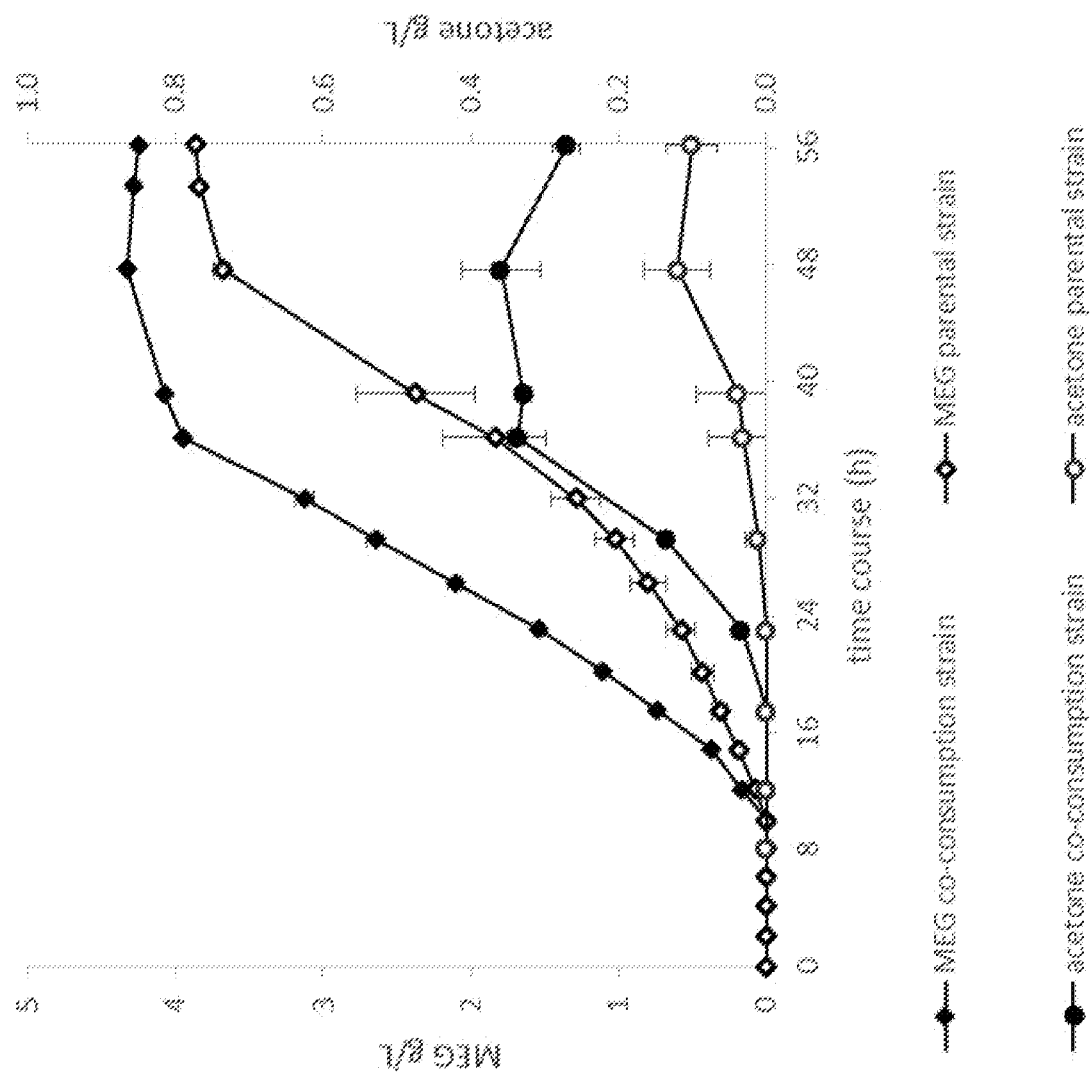
FIG. 4 is a graph depicting MEG usage in the strains. The total amount of MEG was increased by 12% and the amount of acetone was increased by 197%.

For the 6:1 proportion cultures, both parental and co-consumption strain were able to fully consume the initial glucose and xylose, with similar profiles of xylose consumption and biomass production (FIG. 3). In the co-consumption strain, the total amount of MEG was increased by 12% and the amount of acetone was increased by 197% (FIG. 4). The modifications in the xylose uptake provided an improvement in the velocity of co-production in relation with its parental strain.

Example 2: Co-Production of Monoethylene Glycol (MEG) and Acetone Via D-Xylulose Pathway in a Strain Capable of Simultaneously Consuming Xylose and Glucose—Pathway B of FIG. 1

The E. coli K12 strain MG1655 was used as host for the deletion of three genes that could divert the carbon flux from MEG+Acetone pathway: aldA, xylB, and glcDEF. The genes were successfully deleted and deletion confirmed by PCR and sequencing. The next step was the integration of the MEG pathway. An operon expressed under control of the proD promoter containing a khk-C gene (ketohexokinase), aldoB gene (fructose-1,6-bisphosphate aldolase) and a fucO gene (glycoaldehyde reductase) was integrated in E. coli genome and an additional copy of khk-C and aldoB genes also under control of proD promoter was integrated in a different loci. The integration of the khk-C and aldoB genes allows for the conversion of xylose into the intermediate glycolaldehyde. The integration of the fucO gene reduces the glycolaldehyde to MEG, and is specific to MEG production. The second step was the integration of the acetone pathway. An operon expressed under control of the OXB11 promoter containing a thlA gene (acetoacetyl-CoA thiolase); AtoDA genes (acetate:acetoacetyl-CoA transferase) and an adc gene (acetoacetate decarboxylase) was integrated in the E. coli genome, generating the base strain. The base strain was used as host for the modifications to promote co-consumption of glucose and xylose. The first modification was the integration of an additional copy of the xylE under control of a GAPDH promoter on the araFGH locus, thus deleting araFGH. The second modification was the deletion of the xylFGH operon and replacement of the xylA promoter by the OXB15 promoter. The expression of xylA under a constitutive promoter allows for the conversion of xylose into the intermediates D-xylonate and glycolaldehyde. All of the integrations and deletions were confirmed by PCR and sequencing.

Colonies from transformations were inoculated in 5 mL of mineral media containing either 12.85 g/L of xylose and 2.15 g/L of glucose (6:1 proportion) or 7.5 g/L of xylose and 7.5 g/L of glucose (1:1 proportion) for pre-culture. After 16 hours of cultivation 5% of the pre-culture was transferred to 100 mL of fresh media. The flasks were incubated at 37° C., 250 rpm. The initial OD of the cultivation was 0.1.

Figure 5:
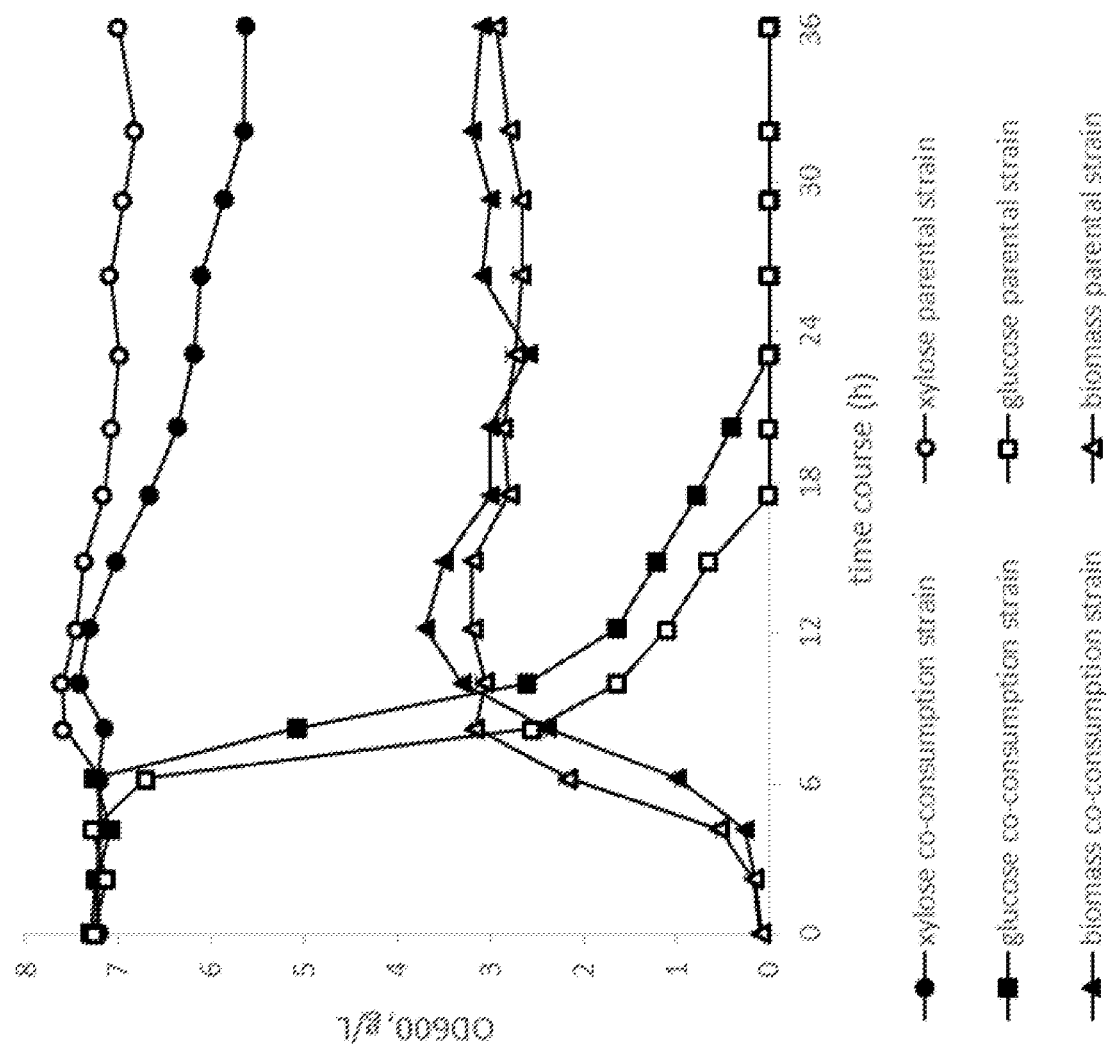
FIG. 5 is a graph depicting the detection of simultaneous utilization of glucose and xylose in a co-consumption strain, while in the parental strain the xylose started to decrease only after 18 h, after depletion of glucose; in 1:1 proportion cultures.

For the 1:1 proportion cultures, after 12 hours of cultivation, simultaneous utilization of glucose and xylose could be detected in the co-consumption strain while in the parental strain the xylose started to decrease only after 18 h, after depletion of glucose (FIG. 5). In 36 h of cultivation, the co-consumption strain was able to consume 61% of initial mixture of sugars while the parental strain consumed 52%.

Figure 6:
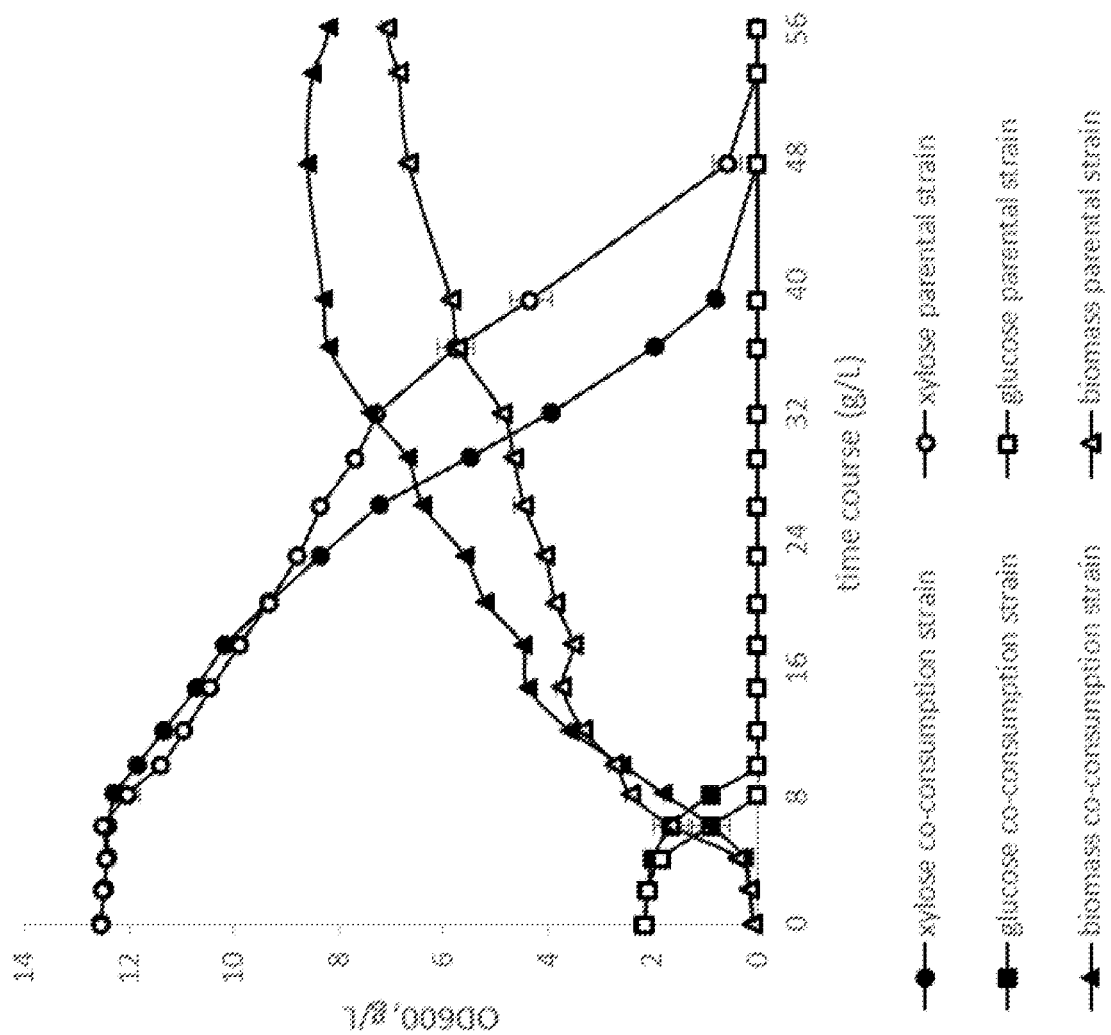
FIG. 6 is a graph depicting the co-consumption strain consuming 61% of the initial mixture of sugars while the parental strain consumed 52% of the sugars (36 h of cultivation. For the 6:1 proportion cultures, the co-consumption and parental strain fully consuming the initial glucose and xylose, with similar profiles of xylose consumption and biomass production.
Figure 7:
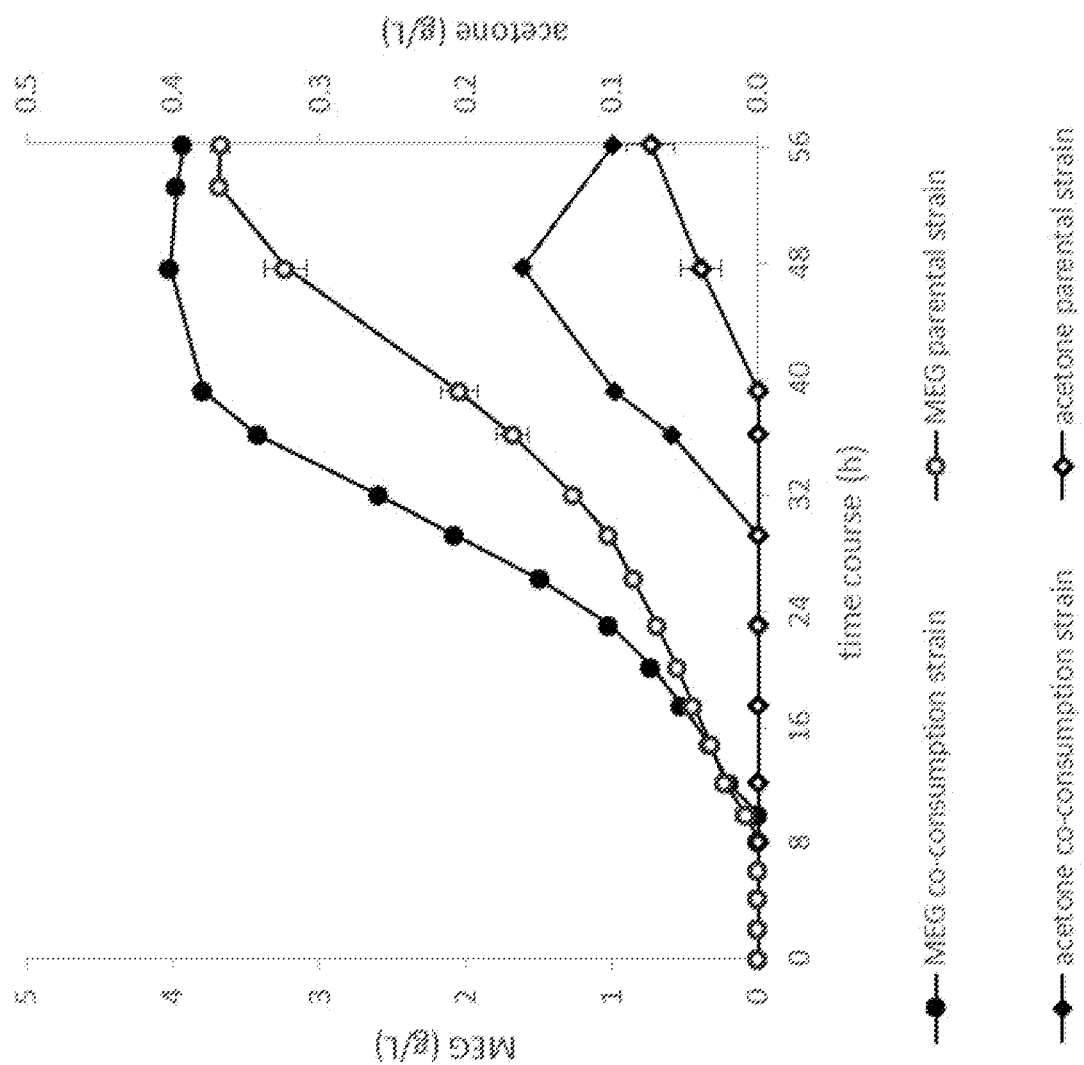
FIG. 7 is a graph depicting the total amount of MEG increased by 9% and the total amount of acetone was increased by 119%.

For the 6:1 proportion cultures, both the parental and the co-consumption strain was able to fully consume the initial glucose and xylose, with similar profiles of xylose consumption and biomass production (FIG. 6). In the co-consumption strain, the total amount of MEG was increased by 9% and the total amount of acetone was increased by 119% (FIG. 7). The modifications in the xylose uptake provided an improvement in the velocity of co-production in relation with its parental strain.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, the following references are hereby incorporated by reference:

Yang et al. (2018). One step fermentative production of aromatic polyesters from glucose by metabolically engineered *Escherichia coli* strains. *Nature Communications*. 9(1):79.

Fritzsche et al. (1990). An unusual bacterial polyester with a phenyl pendant group. *Die Makromolekulare Chemie: Macromolecular Chemistry and Physics*. 191(8): 1957-1965.

Garcia et al. (1999). Novel biodegradable aromatic plastics from a bacterial source genetic and biochemical studies on a route of the phenylacetyl-CoA catabolon. *Journal of Biological Chemistry*. 274(41):29228-29241.

Olivera et al. (2001). Genetically engineered *Pseudomonas*: a factory of new bioplastics with broad applications. *Environmental Microbiology*. 3 (10): 612-618.

What is claimed is:

1. A recombinant microorganism capable of producing a fermentation product from a feedstock comprising xylose and glucose, wherein the recombinant microorganism simultaneously utilizes the xylose and the glucose, and wherein the recombinant microorganism comprises:
   (a) a deletion or an inactivation of nucleic acid sequences that encode a xylose ABC transporter and an arabinose ABC transporter;
   (b) one or more endogenous or exogenous nucleic acid sequences that encodes a C5 sugar symporter operatively linked to one or more constitutive promoters, wherein the C5 sugar symporter comprises: (1) a xylose symporter and/or a (2) an arabinose symporter;
   (c) one or more endogenous or exogenous nucleic acid sequences that encodes (1) a xylose isomerase operatively linked to one or more constitutive promoters, and a deletion or an inactivation of one or more nucleic acid sequences that encodes a xylulokinase or (2) a xylose dehydrogenase operatively linked to one or more constitutive promoters and a deletion or an inactivation of one or more nucleic acid sequences that encodes a xylose isomerase and/or a xylulokinase;
   (d) a deletion or an inactivation of one or more nucleic acid sequences that encodes a glycolate dehydrogenase; and
   (e) a native functional phosphotransferase system (PTS) and a native cAMP receptor protein (CRP);
   wherein the recombinant microorganism is E. coli.

2. The recombinant microorganism of claim 1, wherein the fermentation product comprises monoethylene glycol (MEG), acetone, isopropanol, glycolate, and/or propylene.

3. The recombinant microorganism of claim 1, wherein two or more fermentation products are produced simultaneously.

4. The recombinant microorganism of claim 1, wherein the recombinant microorganism comprises one or more endogenous or exogenous nucleic acid sequences that encodes a xylose dehydrogenase and a glycoaldehyde reductase operatively linked to one or more constitutive promoters and a deletion or an inactivation of one or more nucleic acid sequences that encodes a xylose isomerase.

5. The recombinant microorganism of claim 1, wherein the fermentation product comprises monoethylene glycol (MEG) and/or acetone.

6. A recombinant microorganism capable of producing monoethylene glycol (MEG), isopropanol and/or acetone from a feedstock comprising xylose and glucose, wherein the recombinant microorganism simultaneously utilizes xylose and glucose, wherein the recombinant microorganism comprises:
   (a) a deletion or an inactivation of nucleic acid sequences that encode a glycoaldehyde dehydrogenase, a xylose ABC transporter, and an arabinose ABC transporter;
   (b) at least one endogenous or exogenous nucleic acid molecule operatively linked to one or more constitutive promoters encoding a C5 sugar symporter;
   (c) a deletion or an inactivation of a glycolate dehydrogenase and either a xylose isomerase or a xylulokinase; and
   (d) a native functional phosphotransferase system (PTS) and a native cAMP receptor protein (CRP),
   wherein the recombinant microorganism comprises enzymatic pathways for MEG, isopropanol, and/or acetone production; and
   wherein the recombinant microorganism is E. coli.

7. The recombinant microorganism of claim 6, wherein the glycoaldehyde dehydrogenase is aldA, the xylose ABC transporter is xylFGH, the arabinose ABC transporter is araFGH, the glycolate dehydrogenase is glcDEF, the xylose isomerase is xylA, and the xylulokinase is xylB.

8. The recombinant microorganism of claim 6, further comprising one or more endogenous or exogenous nucleic acid sequences that encode a constitutive promoter, an acetoacetyl-CoA thiolase, an acetate:acetoacetyl-CoA transferase, and/or an acetoacetate decarboxylase.

9. The recombinant microorganism of claim 8, wherein the nucleic acid sequence that encodes the constitutive promoter has at least 95% sequence identity to SEQ ID NO: 78, the nucleic acid sequence that encodes the acetoacetyl-CoA thiolase has at least 95% sequence identity to SEQ ID NOs: 66 or 68, the nucleic acid sequence that encodes the acetate:acetoacetyl-CoA transferase has at least 95% sequence identity to SEQ ID NOs: 70 or 71, the nucleic acid sequence that encodes the acetoacetate decarboxylase has at least 95% sequence identity to SEQ ID NOs: 74 or 76, the amino acid sequence of the acetoacetyl-CoA thiolase has at least 95% sequence identity to SEQ ID NOs: 67 or 69, the amino acid sequence of the acetate:acetoacetyl-CoA transferase has at least 95% sequence identity to SEQ ID NOs: 72 or 73, and/or the amino acid sequence of the acetoacetate decarboxylase has at least 95% sequence identity to SEQ ID NOs: 75 or 77.

10. The recombinant microorganism of claim 6, wherein the C5 sugar symporter is a xylose symporter.

11. The recombinant microorganism of claim 10, wherein the nucleic acid sequence that encodes the xylose symporter has at least 95% sequence identity to SEQ ID NO: 48 or the amino acid sequence of the xylose symporter has at least 95% sequence identity to SEQ ID NO: 49.

12. The recombinant microorganism of claim 6, further comprising one or more endogenous or exogenous nucleic acid sequences that encode a constitutive promoter, at least one xylose dehydrogenase and a glycoaldehyde reductase.

13. The recombinant microorganism of claim 12, wherein the nucleic acid sequence that encodes the constitutive promoter has at least 95% sequence identity to SEQ ID NO: 53, the nucleic acid sequence that encodes the xylose dehydrogenase has at least 95% sequence identity to SEQ ID NOs: 15, 18, or 97, the nucleic acid sequence that encodes the glycoaldehyde reductase has at least 95% sequence identity to SEQ ID NO: 52, the amino acid sequence of the xylose dehydrogenase has at least 95% sequence identity to SEQ ID NOs: 16, 17, or 19, and/or the amino acid sequence of the glycoaldehyde reductase has at least 95% sequence identity to SEQ ID NO: 98.

14. The recombinant microorganism of claim 6, further comprising one or more endogenous or exogenous nucleic acid sequences that encodes a constitutive promoter, at least one ketohexokinase, a fructose-1,6-bisphosphate aldolase, and a glycoaldehyde reductase.

15. The recombinant microorganism of claim 14, wherein the nucleic acid sequence that encodes the constitutive promoter has at least 95% sequence identity to SEQ ID NO: 53, the nucleic acid sequence that encodes the ketohexokinase has at least 95% identity to SEQ ID NO: 11, the nucleic acid sequence that encodes the fructose-1,6-bisphosphate aldolase has at least 95% sequence identity to SEQ ID NO: 50, the nucleic acid sequence that encodes the glycoaldehyde reductase has at least 95% sequence identity to SEQ ID NO: 52, the amino acid sequence of the ketohexokinase has at least 95% identity to SEQ ID NO: 12, the amino acid sequence of the fructose-1,6-bisphosphate aldolase has at least 95% sequence identity to SEQ ID NO: 51, and/or the amino acid sequence of the glycoaldehyde reductase has at least 95% sequence identity to SEQ ID NO: 98.

16. The recombinant microorganism of claim 6, wherein the recombinant microorganism comprises a deletion or an inactivation of a xylulokinase.

17. The recombinant microorganism of claim 6, wherein the recombinant microorganism comprises a deletion or an inactivation of a xylose isomerase.

18. The recombinant microorganism of claim 6, wherein the recombinant microorganism is capable of producing monoethylene glycol (MEG) and/or acetone and comprises enzymatic pathways for MEG and/or acetone production.

19. A recombinant microorganism capable of producing glycolic acid from a feedstock comprising xylose and glucose, wherein the recombinant microorganism simultaneously utilizes xylose and glucose, wherein the recombinant microorganism comprises:
(a) a deletion or an inactivation of nucleic acid sequences that encode one or more glycoaldehyde reductases, a xylose ABC transporter and an arabinose ABC transporter;
(b) at least one endogenous or exogenous nucleic acid molecule operatively linked to one or more constitutive promoters encoding a C5 sugar symporter;
(c) a deletion or an inactivation of a xylose isomerase and/or a xylulokinase; and
(d) a native functional phosphotransferase system (PTS) and a native cAMP receptor protein (CRP),
wherein the recombinant microorganism comprises enzymatic pathways for glycolic acid production and the recombinant microorganism is *E. coli*.

20. The recombinant microorganism of claim 19, wherein the glycoaldehyde reductases are fucO and yqhD, the xylose ABC transporter is xylFGH, the arabinose ABC transporter is araFGH, the C5 sugar symporter is xylE, the xylose isomerase is xylA, and the xylulokinase is xylB.

* * * * *